United States Patent
Long et al.

(10) Patent No.: US 10,098,691 B2
(45) Date of Patent: Oct. 16, 2018

(54) SURGICAL INSTRUMENT COMPRISING AN ELECTRODE

(71) Applicant: Ethicon Endo-Surgery, Inc., Cincinnati, OH (US)

(72) Inventors: Gary L. Long, Cincinnati, OH (US); David N. Plescia, Mentor, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 382 days.

(21) Appl. No.: 14/695,824

(22) Filed: Apr. 24, 2015

(65) Prior Publication Data
US 2015/0230858 A1     Aug. 20, 2015

Related U.S. Application Data

(62) Division of application No. 12/641,837, filed on Dec. 18, 2009, now Pat. No. 9,028,483.

(51) Int. Cl.
*A61B 18/14* (2006.01)
*A61B 18/00* (2006.01)

(52) U.S. Cl.
CPC ...... *A61B 18/1477* (2013.01); *A61B 18/1402* (2013.01); *A61B 2018/0022* (2013.01);
(Continued)

(58) Field of Classification Search
CPC ............ A61B 18/1492; A61B 18/1477; A61B 2018/00577; A61B 2018/1475; A61B 2018/143
See application file for complete search history.

(56) References Cited

U.S. PATENT DOCUMENTS

| 645,576 A | 3/1900 | Tesla |
| 649,621 A | 5/1900 | Tesla |

(Continued)

FOREIGN PATENT DOCUMENTS

| AU | 666310 B2 | 2/1996 |
| DE | 3008120 A1 | 9/1980 |

(Continued)

OTHER PUBLICATIONS

Michael S. Kavic, M.D., "Natural Orifice Translumenal Endoscopic Surgery: "NOTES"", JSLS, vol. 10, pp. 133-134 (2006).
(Continued)

*Primary Examiner* — Michael Peffley

(57) ABSTRACT

A surgical instrument configured to deliver electrical energy to the tissue of a patient is disclosed. The surgical instrument comprises a frame, a first electrode, a second electrode, and a guard movable between a first position and a second position. The surgical instrument further comprises a spring positioned intermediate the guard and the frame. The spring is configured to bias the guard into the first position. When the guard is in the first position, a distal end of the guard is positioned at least flush with distal ends of the first electrode and the second electrode, which prevents current from arcing between the first electrode and the second electrode. When the guard is in the second position, the distal end of the guard is in contact with the tissue, which prevents current from arcing between the first electrode and the second electrode without passing through the tissue.

14 Claims, 21 Drawing Sheets

(52) U.S. Cl.
CPC ............... *A61B 2018/00077* (2013.01); *A61B 2018/00107* (2013.01); *A61B 2018/00577* (2013.01); *A61B 2018/1465* (2013.01)

(56) References Cited

U.S. PATENT DOCUMENTS

| | | | |
|---|---|---|---|
| 787,412 A | 4/1905 | Tesla |
| 1,039,354 A | 9/1912 | Bonadio |
| 1,127,948 A | 2/1915 | Wappler |
| 1,482,653 A | 2/1924 | Lilly |
| 1,581,706 A | 4/1926 | White |
| 1,581,707 A | 4/1926 | White |
| 1,581,708 A | 4/1926 | White |
| 1,581,709 A | 4/1926 | White |
| 1,581,710 A | 4/1926 | White |
| 1,625,602 A | 4/1927 | Gould et al. |
| 1,916,722 A | 7/1933 | Ende |
| 2,028,635 A | 1/1936 | Wappler |
| 2,031,682 A | 2/1936 | Wappler et al. |
| 2,113,246 A | 4/1938 | Wappler |
| 2,137,710 A | 11/1938 | Anderson |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,451,077 A | 10/1948 | Emsig |
| 2,493,108 A | 1/1950 | Casey, Jr. |
| 2,504,152 A | 4/1950 | Riker et al. |
| 2,938,382 A | 5/1960 | De Graaf |
| 2,952,206 A | 9/1960 | Becksted |
| 3,044,461 A | 7/1962 | Murdock |
| 3,069,195 A | 12/1962 | Buck |
| 3,070,088 A | 12/1962 | Brahos |
| 3,170,471 A | 2/1965 | Schnitzer |
| 3,435,824 A | 4/1969 | Gamponia |
| 3,470,876 A | 10/1969 | Barchilon |
| 3,481,325 A | 12/1969 | Glassman |
| 3,595,239 A | 7/1971 | Petersen |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,946,740 A | 3/1976 | Bassett |
| 3,948,251 A | 4/1976 | Hosono |
| 3,961,632 A | 6/1976 | Moossun |
| 3,965,890 A | 6/1976 | Gauthier |
| 3,994,301 A | 11/1976 | Agris |
| 4,011,872 A | 3/1977 | Komiya |
| 4,012,812 A | 3/1977 | Black |
| 4,043,342 A * | 8/1977 | Morrison, Jr. ...... A61B 18/1402 606/48 |
| 4,071,028 A * | 1/1978 | Perkins ................. A61B 18/12 307/117 |
| 4,085,743 A | 4/1978 | Yoon |
| 4,164,225 A | 8/1979 | Johnson et al. |
| 4,170,997 A | 10/1979 | Pinnow et al. |
| 4,174,715 A | 11/1979 | Hasson |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,281,646 A | 8/1981 | Kinoshita |
| 4,285,344 A | 8/1981 | Marshall |
| 4,311,143 A | 1/1982 | Komiya |
| 4,329,980 A | 5/1982 | Terada |
| 4,393,872 A | 7/1983 | Reznik et al. |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,492,232 A | 1/1985 | Green |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,649,904 A | 3/1987 | Krauter et al. |
| 4,653,476 A | 3/1987 | Bonnet |
| 4,655,219 A | 4/1987 | Petruzzi |
| 4,657,016 A | 4/1987 | Garito et al. |
| 4,657,018 A | 4/1987 | Hakky |
| 4,669,470 A | 6/1987 | Brandfield |
| 4,671,477 A | 6/1987 | Cullen |
| 4,677,982 A | 7/1987 | Llinas et al. |
| 4,685,447 A | 8/1987 | Iversen et al. |
| 4,711,239 A * | 12/1987 | Sorochenko ............ A61B 18/14 219/234 |
| 4,711,240 A | 12/1987 | Goldwasser et al. |
| 4,712,545 A | 12/1987 | Honkanen |
| 4,721,116 A | 1/1988 | Schintgen et al. |
| 4,727,600 A | 2/1988 | Avakian |
| 4,733,662 A | 3/1988 | DeSatnick et al. |
| D295,894 S | 5/1988 | Sharkany et al. |
| 4,742,817 A | 5/1988 | Kawashima et al. |
| 4,753,223 A | 6/1988 | Bremer |
| 4,763,669 A | 8/1988 | Jaeger |
| 4,770,188 A | 9/1988 | Chikama |
| 4,790,624 A | 12/1988 | Van Hoye et al. |
| 4,791,707 A | 12/1988 | Tucker |
| 4,796,627 A | 1/1989 | Tucker |
| 4,807,593 A | 2/1989 | Ito |
| 4,815,450 A | 3/1989 | Patel |
| 4,819,620 A | 4/1989 | Okutsu |
| 4,823,794 A | 4/1989 | Pierce |
| 4,829,999 A | 5/1989 | Auth |
| 4,836,188 A | 6/1989 | Berry |
| 4,846,573 A | 7/1989 | Taylor et al. |
| 4,867,140 A | 9/1989 | Hovis et al. |
| 4,869,238 A | 9/1989 | Opie et al. |
| 4,869,459 A | 9/1989 | Bourne |
| 4,873,979 A | 10/1989 | Hanna |
| 4,880,015 A | 11/1989 | Nierman |
| 4,904,048 A | 2/1990 | Sogawa et al. |
| 4,911,148 A | 3/1990 | Sosnowski et al. |
| 4,926,860 A | 5/1990 | Stice et al. |
| 4,934,364 A | 6/1990 | Green |
| 4,938,214 A | 7/1990 | Specht et al. |
| 4,950,273 A | 8/1990 | Briggs |
| 4,950,285 A | 8/1990 | Wilk |
| 4,953,539 A | 9/1990 | Nakamura et al. |
| 4,960,133 A | 10/1990 | Hewson |
| 4,977,887 A | 12/1990 | Gouda |
| 4,979,496 A | 12/1990 | Komi |
| 4,979,950 A | 12/1990 | Transue et al. |
| 4,984,581 A | 1/1991 | Stice |
| 4,990,152 A | 2/1991 | Yoon |
| 4,991,565 A | 2/1991 | Takahashi et al. |
| 4,994,079 A | 2/1991 | Genese et al. |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,026,379 A | 6/1991 | Yoon |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,098,378 A | 3/1992 | Piontek et al. |
| 5,108,421 A | 4/1992 | Fowler |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,174,300 A | 12/1992 | Bales et al. |

(56) References Cited

U.S. PATENT DOCUMENTS

| | | |
|---|---|---|
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,192,300 A | 3/1993 | Fowler |
| 5,197,963 A | 3/1993 | Parins |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,245,460 A | 9/1993 | Allen et al. |
| 5,246,424 A | 9/1993 | Wilk |
| 5,257,999 A | 11/1993 | Slanetz, Jr. |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,275,614 A | 1/1994 | Haber et al. |
| 5,275,616 A | 1/1994 | Fowler |
| 5,284,128 A | 2/1994 | Hart |
| 5,284,162 A | 2/1994 | Wilk |
| 5,287,845 A | 2/1994 | Faul et al. |
| 5,287,852 A | 2/1994 | Arkinstall |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,297,687 A | 3/1994 | Freed |
| 5,301,061 A | 4/1994 | Nakada et al. |
| 5,312,023 A | 5/1994 | Green et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,318,589 A | 6/1994 | Lichtman |
| 5,320,636 A | 6/1994 | Slater |
| 5,324,261 A | 6/1994 | Amundson et al. |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,168 A | 8/1994 | Hemmer |
| 5,334,198 A | 8/1994 | Hart et al. |
| 5,336,192 A | 8/1994 | Palestrant |
| 5,336,222 A * | 8/1994 | Durgin, Jr. ......... A61B 18/1477 604/21 |
| 5,339,805 A | 8/1994 | Parker |
| 5,341,815 A | 8/1994 | Cofone et al. |
| 5,342,396 A | 8/1994 | Cook |
| 5,344,428 A | 9/1994 | Griffiths |
| 5,345,927 A | 9/1994 | Bonutti |
| 5,348,259 A | 9/1994 | Blanco et al. |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,381 A | 10/1994 | Ensminger et al. |
| 5,356,408 A | 10/1994 | Rydell |
| 5,360,428 A | 11/1994 | Hutchinson, Jr. |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,374,953 A | 12/1994 | Sasaki et al. |
| 5,376,077 A | 12/1994 | Gomringer |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,387,259 A | 2/1995 | Davidson |
| 5,391,174 A | 2/1995 | Weston |
| 5,392,789 A | 2/1995 | Slater et al. |
| 5,395,386 A | 3/1995 | Slater |
| 5,397,332 A | 3/1995 | Kammerer et al. |
| 5,401,248 A | 3/1995 | Bencini |
| 5,403,311 A | 4/1995 | Abele et al. |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,431,635 A | 7/1995 | Yoon |
| 5,433,721 A | 7/1995 | Hooven et al. |
| 5,433,735 A | 7/1995 | Zanakis et al. |
| 5,439,471 A | 8/1995 | Kerr |
| 5,439,478 A | 8/1995 | Palmer |
| 5,441,059 A | 8/1995 | Dannan |
| 5,441,494 A | 8/1995 | Ortiz |
| 5,441,498 A | 8/1995 | Perkins |
| 5,441,499 A | 8/1995 | Fritzsch |
| 5,443,463 A | 8/1995 | Stern et al. |
| 5,445,638 A | 8/1995 | Rydell et al. |
| 5,445,648 A | 8/1995 | Cook |
| 5,449,021 A | 9/1995 | Chikama |
| 5,454,827 A | 10/1995 | Aust et al. |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,472,441 A | 12/1995 | Edwards et al. |
| 5,478,347 A | 12/1995 | Aranyi |
| 5,478,352 A | 12/1995 | Fowler |
| 5,480,404 A | 1/1996 | Kammerer et al. |
| 5,482,029 A | 1/1996 | Sekiguchi et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schülken et al. |
| 5,499,992 A | 3/1996 | Meade et al. |
| 5,499,997 A | 3/1996 | Sharpe et al. |
| 5,500,012 A | 3/1996 | Brucker et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,518,501 A | 5/1996 | Oneda et al. |
| 5,522,829 A | 6/1996 | Michalos |
| 5,522,830 A | 6/1996 | Aranyi |
| 5,527,321 A | 6/1996 | Hinchliffe |

(56) References Cited

U.S. PATENT DOCUMENTS

| | | |
|---|---|---|
| 5,533,418 A | 7/1996 | Wu et al. |
| 5,536,234 A | 7/1996 | Newman |
| 5,536,248 A | 7/1996 | Weaver et al. |
| 5,538,509 A | 7/1996 | Dunlap et al. |
| 5,540,648 A | 7/1996 | Yoon |
| 5,549,637 A | 8/1996 | Crainich |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,571,090 A | 11/1996 | Sherts |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,590,660 A | 1/1997 | MacAulay et al. |
| 5,591,179 A | 1/1997 | Edelstein |
| 5,591,205 A | 1/1997 | Fowler |
| 5,593,420 A | 1/1997 | Eubanks, Jr. et al. |
| 5,595,562 A | 1/1997 | Grier |
| 5,597,378 A | 1/1997 | Jervis |
| 5,601,573 A | 2/1997 | Fogelberg et al. |
| 5,601,574 A | 2/1997 | Stefanchik et al. |
| 5,601,588 A | 2/1997 | Tonomura et al. |
| 5,601,602 A | 2/1997 | Fowler |
| 5,604,531 A | 2/1997 | Iddan et al. |
| 5,607,386 A | 3/1997 | Flam |
| 5,607,389 A | 3/1997 | Edwards et al. |
| 5,607,406 A | 3/1997 | Hernandez et al. |
| 5,607,450 A | 3/1997 | Zvenyatsky et al. |
| 5,609,601 A | 3/1997 | Kolesa et al. |
| 5,613,975 A | 3/1997 | Christy |
| 5,613,977 A | 3/1997 | Weber et al. |
| 5,614,943 A | 3/1997 | Nakamura et al. |
| 5,616,117 A | 4/1997 | Dinkler et al. |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,626,587 A | 5/1997 | Bishop et al. |
| 5,628,732 A | 5/1997 | Antoon, Jr. et al. |
| 5,630,782 A | 5/1997 | Adair |
| 5,630,795 A | 5/1997 | Kuramoto et al. |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,645,519 A | 7/1997 | Lee et al. |
| 5,645,565 A | 7/1997 | Rudd et al. |
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,657,755 A | 8/1997 | Desai |
| 5,662,621 A | 9/1997 | Lafontaine |
| 5,662,663 A | 9/1997 | Shallman |
| 5,667,527 A | 9/1997 | Cook |
| 5,669,875 A | 9/1997 | van Eerdenburg |
| 5,681,276 A | 10/1997 | Lundquist |
| 5,681,279 A | 10/1997 | Roper et al. |
| 5,681,324 A | 10/1997 | Kammerer et al. |
| 5,681,330 A | 10/1997 | Hughett et al. |
| 5,685,820 A | 11/1997 | Riek et al. |
| 5,690,606 A | 11/1997 | Slotman |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,711,921 A | 1/1998 | Langford |
| 5,716,326 A | 2/1998 | Dannan |
| 5,716,375 A | 2/1998 | Fowler |
| 5,725,542 A | 3/1998 | Yoon |
| 5,728,094 A | 3/1998 | Edwards |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,741,429 A | 4/1998 | Donadio, III et al. |
| 5,743,456 A | 4/1998 | Jones et al. |
| 5,746,759 A | 5/1998 | Meade et al. |
| 5,749,826 A | 5/1998 | Faulkner |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,759,150 A | 6/1998 | Konou et al. |
| 5,759,151 A | 6/1998 | Sturges |
| 5,762,604 A | 6/1998 | Kieturakis |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,776,188 A | 7/1998 | Shepherd et al. |
| 5,779,701 A | 7/1998 | McBrayer et al. |
| 5,779,716 A | 7/1998 | Cano et al. |
| 5,779,720 A | 7/1998 | Walder-Utz et al. |
| 5,779,727 A | 7/1998 | Orejola |
| 5,782,859 A | 7/1998 | Nicholas et al. |
| 5,782,861 A | 7/1998 | Cragg et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,797,959 A | 8/1998 | Castro et al. |
| 5,797,960 A | 8/1998 | Stevens et al. |
| 5,800,449 A | 9/1998 | Wales |
| 5,800,451 A | 9/1998 | Buess et al. |
| 5,803,903 A | 9/1998 | Athas et al. |
| 5,807,395 A | 9/1998 | Mulier et al. |
| 5,808,665 A | 9/1998 | Green |
| 5,810,805 A | 9/1998 | Sutcu et al. |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,026 A | 9/1998 | Yoon |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,818,527 A | 10/1998 | Yamaguchi et al. |
| 5,819,736 A | 10/1998 | Avny et al. |
| 5,823,947 A | 10/1998 | Yoon et al. |
| 5,824,071 A | 10/1998 | Nelson et al. |
| 5,827,190 A | 10/1998 | Palcic et al. |
| 5,827,276 A | 10/1998 | LeVeen et al. |
| 5,827,281 A | 10/1998 | Levin |
| 5,827,299 A | 10/1998 | Thomason et al. |
| 5,827,323 A | 10/1998 | Klieman et al. |
| 5,830,221 A | 11/1998 | Stein et al. |
| 5,830,231 A | 11/1998 | Geiges, Jr. |
| 5,833,603 A | 11/1998 | Kovacs et al. |
| 5,833,700 A | 11/1998 | Fogelberg et al. |
| 5,833,703 A | 11/1998 | Manushakian |
| 5,833,715 A | 11/1998 | Vachon et al. |
| 5,836,960 A | 11/1998 | Kolesa et al. |

(56) References Cited

U.S. PATENT DOCUMENTS

| | | |
|---|---|---|
| 5,843,017 A | 12/1998 | Yoon |
| 5,843,121 A | 12/1998 | Yoon |
| 5,849,022 A | 12/1998 | Sakashita et al. |
| 5,853,374 A | 12/1998 | Hart et al. |
| 5,855,569 A | 1/1999 | Komi |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,873,849 A | 2/1999 | Bernard |
| 5,876,411 A | 3/1999 | Kontos |
| 5,882,331 A | 3/1999 | Sasaki |
| 5,882,344 A | 3/1999 | Stouder, Jr. |
| 5,893,846 A | 4/1999 | Bales et al. |
| 5,893,874 A | 4/1999 | Bourque et al. |
| 5,893,875 A | 4/1999 | O'Connor et al. |
| 5,897,487 A | 4/1999 | Ouchi |
| 5,899,919 A | 5/1999 | Eubanks, Jr. et al. |
| 5,902,238 A | 5/1999 | Golden et al. |
| 5,902,254 A | 5/1999 | Magram |
| 5,904,702 A | 5/1999 | Ek et al. |
| 5,906,625 A | 5/1999 | Bito et al. |
| 5,908,420 A | 6/1999 | Parins et al. |
| 5,908,429 A | 6/1999 | Yoon |
| 5,911,737 A | 6/1999 | Lee et al. |
| 5,916,146 A | 6/1999 | Allotta et al. |
| 5,916,147 A | 6/1999 | Boury |
| 5,921,892 A | 7/1999 | Easton |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A | 7/1999 | Kontos |
| 5,936,536 A | 8/1999 | Morris |
| 5,938,661 A | 8/1999 | Hahnen |
| 5,941,815 A | 8/1999 | Chang |
| 5,944,718 A | 8/1999 | Austin et al. |
| 5,951,547 A | 9/1999 | Gough et al. |
| 5,951,549 A | 9/1999 | Richardson et al. |
| 5,954,720 A | 9/1999 | Wilson et al. |
| 5,954,731 A | 9/1999 | Yoon |
| 5,957,936 A | 9/1999 | Yoon et al. |
| 5,957,943 A | 9/1999 | Vaitekunas |
| 5,957,953 A | 9/1999 | DiPoto et al. |
| 5,964,782 A | 10/1999 | Lafontaine et al. |
| 5,970,581 A | 10/1999 | Chadwick et al. |
| 5,971,995 A | 10/1999 | Rousseau |
| 5,972,002 A | 10/1999 | Bark et al. |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,938 A | 11/1999 | Yoon |
| 5,984,939 A | 11/1999 | Yoon |
| 5,984,950 A | 11/1999 | Cragg et al. |
| 5,989,182 A | 11/1999 | Hori et al. |
| 5,993,447 A | 11/1999 | Blewett et al. |
| 5,993,474 A | 11/1999 | Ouchi |
| 5,995,875 A | 11/1999 | Blewett et al. |
| 5,997,555 A | 12/1999 | Kontos |
| 6,001,120 A | 12/1999 | Levin |
| 6,004,269 A | 12/1999 | Crowley et al. |
| 6,004,330 A | 12/1999 | Middleman et al. |
| 6,007,566 A | 12/1999 | Wenstrom, Jr. |
| 6,010,515 A | 1/2000 | Swain et al. |
| 6,012,494 A | 1/2000 | Balazs |
| 6,016,452 A | 1/2000 | Kasevich |
| 6,017,356 A | 1/2000 | Frederick et al. |
| 6,019,770 A | 2/2000 | Christoudias |
| 6,024,708 A | 2/2000 | Bales et al. |
| 6,024,747 A | 2/2000 | Kontos |
| 6,027,522 A | 2/2000 | Palmer |
| 6,030,365 A | 2/2000 | Laufer |
| 6,030,384 A | 2/2000 | Nezhat |
| 6,030,634 A | 2/2000 | Wu et al. |
| 6,033,399 A | 3/2000 | Gines |
| 6,033,401 A | 3/2000 | Edwards et al. |
| 6,036,640 A | 3/2000 | Corace et al. |
| 6,036,685 A | 3/2000 | Mueller |
| 6,050,992 A | 4/2000 | Nichols |
| 6,053,927 A | 4/2000 | Hamas |
| 6,053,937 A | 4/2000 | Edwards et al. |
| 6,059,719 A | 5/2000 | Yamamoto et al. |
| 6,066,160 A | 5/2000 | Colvin et al. |
| 6,068,603 A | 5/2000 | Suzuki |
| 6,068,629 A | 5/2000 | Haissaguerre et al. |
| 6,071,233 A | 6/2000 | Ishikawa et al. |
| 6,074,408 A | 6/2000 | Freeman |
| 6,086,530 A | 7/2000 | Mack |
| 6,090,105 A | 7/2000 | Zepeda et al. |
| 6,090,108 A | 7/2000 | McBrayer et al. |
| 6,090,129 A | 7/2000 | Ouchi |
| 6,096,046 A | 8/2000 | Weiss |
| 6,102,909 A | 8/2000 | Chen et al. |
| 6,102,926 A | 8/2000 | Tartaglia et al. |
| 6,106,473 A | 8/2000 | Violante et al. |
| 6,106,521 A | 8/2000 | Blewett et al. |
| 6,109,852 A | 8/2000 | Shahinpoor et al. |
| 6,110,154 A | 8/2000 | Shimomura et al. |
| 6,110,183 A | 8/2000 | Cope |
| 6,113,593 A | 9/2000 | Tu et al. |
| 6,117,144 A | 9/2000 | Nobles et al. |
| 6,117,158 A | 9/2000 | Measamer et al. |
| 6,123,718 A | 9/2000 | Tu et al. |
| 6,131,790 A | 10/2000 | Piraka |
| 6,139,555 A | 10/2000 | Hart et al. |
| 6,141,037 A | 10/2000 | Upton et al. |
| 6,146,391 A | 11/2000 | Cigaina |
| 6,148,222 A | 11/2000 | Ramsey, III |
| 6,149,653 A | 11/2000 | Deslauriers |
| 6,149,662 A | 11/2000 | Pugliesi et al. |
| 6,152,871 A | 11/2000 | Foley et al. |
| 6,152,920 A | 11/2000 | Thompson et al. |
| 6,156,006 A | 12/2000 | Brosens et al. |
| 6,159,200 A | 12/2000 | Verdura et al. |
| 6,165,175 A | 12/2000 | Wampler et al. |
| 6,165,184 A | 12/2000 | Verdura et al. |
| 6,168,570 B1 | 1/2001 | Ferrera |
| 6,168,605 B1 | 1/2001 | Measamer et al. |
| 6,169,269 B1 | 1/2001 | Maynard |
| 6,170,130 B1 | 1/2001 | Hamilton et al. |
| 6,173,872 B1 | 1/2001 | Cohen |
| 6,179,776 B1 | 1/2001 | Adams et al. |
| 6,179,832 B1 | 1/2001 | Jones et al. |
| 6,179,837 B1 | 1/2001 | Hooven |
| 6,183,420 B1 | 2/2001 | Douk et al. |
| 6,190,353 B1 | 2/2001 | Makower et al. |
| 6,190,383 B1 | 2/2001 | Schmaltz et al. |
| 6,190,384 B1 | 2/2001 | Ouchi |
| 6,190,399 B1 | 2/2001 | Palmer et al. |
| 6,203,533 B1 | 3/2001 | Ouchi |
| 6,206,872 B1 | 3/2001 | Lafond et al. |
| 6,206,877 B1 | 3/2001 | Kese et al. |
| 6,206,904 B1 | 3/2001 | Ouchi |
| 6,210,409 B1 | 4/2001 | Ellman et al. |
| 6,214,007 B1 | 4/2001 | Anderson |
| 6,214,028 B1 | 4/2001 | Yoon et al. |
| 6,216,043 B1 | 4/2001 | Swanson et al. |
| 6,228,096 B1 | 5/2001 | Marchand |
| 6,231,506 B1 | 5/2001 | Hu et al. |
| 6,234,958 B1 | 5/2001 | Snoke et al. |
| 6,240,312 B1 | 5/2001 | Alfano et al. |
| 6,245,079 B1 | 6/2001 | Nobles et al. |
| 6,246,914 B1 | 6/2001 | de la Rama et al. |
| 6,258,064 B1 | 7/2001 | Smith et al. |
| 6,261,242 B1 | 7/2001 | Roberts et al. |
| 6,264,664 B1 | 7/2001 | Avellanet |
| 6,270,497 B1 | 8/2001 | Sekino et al. |
| 6,270,505 B1 | 8/2001 | Yoshida et al. |
| 6,277,136 B1 | 8/2001 | Bonutti |
| 6,283,963 B1 | 9/2001 | Regula |

(56) References Cited

U.S. PATENT DOCUMENTS

| | | | |
|---|---|---|---|
| 6,287,304 | B1 | 9/2001 | Eggers et al. |
| 6,293,909 | B1 | 9/2001 | Chu et al. |
| 6,293,952 | B1 | 9/2001 | Brosens et al. |
| 6,296,630 | B1 | 10/2001 | Altman et al. |
| 6,314,963 | B1 | 11/2001 | Vaska et al. |
| 6,322,578 | B1 | 11/2001 | Houle et al. |
| 6,325,534 | B1 | 12/2001 | Hawley et al. |
| 6,326,177 | B1 | 12/2001 | Schoenbach et al. |
| 6,328,730 | B1 | 12/2001 | Harkrider, Jr. |
| 6,350,267 | B1 | 2/2002 | Stefanchik |
| 6,350,278 | B1 | 2/2002 | Lenker et al. |
| 6,352,503 | B1 | 3/2002 | Matsui et al. |
| 6,352,541 | B1 | 3/2002 | Kienzle et al. |
| 6,352,543 | B1 | 3/2002 | Cole |
| 6,355,013 | B1 | 3/2002 | van Muiden |
| 6,355,035 | B1 | 3/2002 | Manushakian |
| 6,361,534 | B1 | 3/2002 | Chen et al. |
| 6,364,879 | B1 | 4/2002 | Chen et al. |
| 6,368,340 | B2 | 4/2002 | Malecki et al. |
| 6,371,956 | B1 | 4/2002 | Wilson et al. |
| 6,379,366 | B1 | 4/2002 | Fleischman et al. |
| 6,383,195 | B1 | 5/2002 | Richard |
| 6,383,197 | B1 | 5/2002 | Conlon et al. |
| 6,387,671 | B1 | 5/2002 | Rubinsky et al. |
| 6,391,029 | B1 | 5/2002 | Hooven et al. |
| 6,398,708 | B1 | 6/2002 | Hastings et al. |
| 6,402,735 | B1 | 6/2002 | Langevin |
| 6,402,746 | B1 | 6/2002 | Whayne et al. |
| 6,406,440 | B1 | 6/2002 | Stefanchik |
| 6,409,727 | B1 | 6/2002 | Bales et al. |
| 6,409,733 | B1 | 6/2002 | Conlon et al. |
| 6,419,639 | B2 | 7/2002 | Walther et al. |
| 6,419,641 | B1 | 7/2002 | Mark et al. |
| 6,427,089 | B1 | 7/2002 | Knowlton |
| 6,431,500 | B1 | 8/2002 | Jacobs et al. |
| 6,436,107 | B1 | 8/2002 | Wang et al. |
| 6,443,970 | B1 | 9/2002 | Schulze et al. |
| 6,443,988 | B2 | 9/2002 | Felt et al. |
| 6,447,444 | B1 | 9/2002 | Avni et al. |
| 6,447,511 | B1 | 9/2002 | Slater |
| 6,447,523 | B1 | 9/2002 | Middleman et al. |
| 6,454,783 | B1 | 9/2002 | Piskun |
| 6,454,785 | B2 | 9/2002 | De Hoyos Garza |
| 6,458,074 | B1 | 10/2002 | Matsui et al. |
| 6,458,076 | B1 | 10/2002 | Pruitt |
| 6,464,701 | B1 | 10/2002 | Hooven et al. |
| 6,464,702 | B2 | 10/2002 | Schulze et al. |
| 6,470,218 | B1 | 10/2002 | Behl |
| 6,475,104 | B1 | 11/2002 | Lutz et al. |
| 6,485,411 | B1 | 11/2002 | Konstorum et al. |
| 6,489,745 | B1 | 12/2002 | Koreis |
| 6,491,626 | B1 | 12/2002 | Stone et al. |
| 6,491,627 | B1 | 12/2002 | Komi |
| 6,491,691 | B1 | 12/2002 | Morley et al. |
| 6,493,590 | B1 | 12/2002 | Wessman et al. |
| 6,494,893 | B2 | 12/2002 | Dubrul et al. |
| 6,500,176 | B1 | 12/2002 | Truckai et al. |
| 6,503,192 | B1 | 1/2003 | Ouchi |
| 6,506,190 | B1 | 1/2003 | Walshe |
| 6,508,827 | B1 | 1/2003 | Manhes |
| 6,514,239 | B2 | 2/2003 | Shimmura et al. |
| 6,517,534 | B1 | 2/2003 | McGovern et al. |
| 6,520,954 | B2 | 2/2003 | Ouchi |
| 6,526,320 | B2 | 2/2003 | Mitchell |
| 6,527,782 | B2 | 3/2003 | Hogg et al. |
| 6,530,880 | B2 | 3/2003 | Pagliuca |
| 6,530,922 | B2 | 3/2003 | Cosman et al. |
| 6,535,764 | B2 | 3/2003 | Imran et al. |
| 6,537,200 | B2 | 3/2003 | Leysieffer et al. |
| 6,543,456 | B1 | 4/2003 | Freeman |
| 6,551,270 | B1 | 4/2003 | Bimbo et al. |
| 6,551,356 | B2 | 4/2003 | Rousseau |
| 6,554,766 | B2 | 4/2003 | Maeda et al. |
| 6,554,823 | B2 | 4/2003 | Palmer et al. |
| 6,554,829 | B2 | 4/2003 | Schulze et al. |
| 6,558,384 | B2 | 5/2003 | Mayenberger |
| 6,562,034 | B2 | 5/2003 | Edwards et al. |
| 6,562,035 | B1 | 5/2003 | Levin |
| 6,562,052 | B2 | 5/2003 | Nobles et al. |
| 6,569,120 | B1 | 5/2003 | Green et al. |
| 6,569,159 | B1 | 5/2003 | Edwards et al. |
| 6,572,629 | B2 | 6/2003 | Kalloo et al. |
| 6,572,635 | B1 | 6/2003 | Bonutti |
| 6,575,988 | B2 | 6/2003 | Rousseau |
| 6,579,311 | B1 | 6/2003 | Makower |
| 6,581,889 | B2 | 6/2003 | Carpenter et al. |
| 6,585,642 | B2 | 7/2003 | Christopher |
| 6,585,717 | B1 | 7/2003 | Wittenberger et al. |
| 6,587,750 | B2 | 7/2003 | Gerbi et al. |
| 6,592,559 | B1 | 7/2003 | Pakter et al. |
| 6,592,603 | B2 | 7/2003 | Lasner |
| 6,594,971 | B1 | 7/2003 | Addy et al. |
| 6,602,262 | B2 | 8/2003 | Griego et al. |
| 6,605,105 | B1 | 8/2003 | Cuschieri et al. |
| 6,610,072 | B1 | 8/2003 | Christy et al. |
| 6,610,074 | B2 | 8/2003 | Santilli |
| 6,613,038 | B2 | 9/2003 | Bonutti et al. |
| 6,613,068 | B2 | 9/2003 | Ouchi |
| 6,616,632 | B2 | 9/2003 | Sharp et al. |
| 6,620,193 | B1 | 9/2003 | Lau et al. |
| 6,623,448 | B2 | 9/2003 | Slater |
| 6,626,919 | B1 | 9/2003 | Swanstrom |
| 6,632,171 | B2 | 10/2003 | Iddan et al. |
| 6,632,229 | B1 | 10/2003 | Yamanouchi |
| 6,632,234 | B2 | 10/2003 | Kieturakis et al. |
| 6,638,275 | B1 | 10/2003 | McGaffigan et al. |
| 6,638,286 | B1 | 10/2003 | Burbank et al. |
| 6,645,225 | B1 | 11/2003 | Atkinson |
| 6,652,518 | B2 | 11/2003 | Wellman et al. |
| 6,652,521 | B2 | 11/2003 | Schulze |
| 6,652,545 | B2 | 11/2003 | Shipp et al. |
| 6,652,551 | B1 | 11/2003 | Heiss |
| 6,656,194 | B1 | 12/2003 | Gannoe et al. |
| 6,663,641 | B1 | 12/2003 | Kovac et al. |
| 6,663,655 | B2 | 12/2003 | Ginn et al. |
| 6,666,854 | B1 | 12/2003 | Lange |
| 6,672,338 | B1 | 1/2004 | Esashi et al. |
| 6,673,058 | B2 | 1/2004 | Snow |
| 6,673,070 | B2 | 1/2004 | Edwards et al. |
| 6,673,087 | B1 | 1/2004 | Chang et al. |
| 6,673,092 | B1 | 1/2004 | Bacher |
| 6,676,685 | B2 | 1/2004 | Pedros et al. |
| 6,679,882 | B1 | 1/2004 | Kornerup |
| 6,685,628 | B2 | 2/2004 | Vu |
| 6,685,724 | B1 | 2/2004 | Haluck |
| 6,692,445 | B2 | 2/2004 | Roberts et al. |
| 6,692,462 | B2 | 2/2004 | Mackenzie et al. |
| 6,692,493 | B2 | 2/2004 | McGovern et al. |
| 6,699,180 | B2 | 3/2004 | Kobayashi |
| 6,699,256 | B1 | 3/2004 | Logan et al. |
| 6,699,263 | B2 | 3/2004 | Cope |
| 6,706,018 | B2 | 3/2004 | Westlund et al. |
| 6,708,066 | B2 | 3/2004 | Herbst et al. |
| 6,709,188 | B2 | 3/2004 | Ushimaru |
| 6,709,445 | B2 | 3/2004 | Boebel et al. |
| 6,716,226 | B2 | 4/2004 | Sixto, Jr. et al. |
| 6,731,875 | B1 | 5/2004 | Kartalopoulos |
| 6,736,822 | B2 | 5/2004 | McClellan et al. |
| 6,740,030 | B2 | 5/2004 | Martone et al. |
| 6,740,082 | B2 | 5/2004 | Shadduck |
| 6,743,166 | B2 | 6/2004 | Berci et al. |
| 6,743,226 | B2 | 6/2004 | Cosman et al. |
| 6,743,239 | B1 | 6/2004 | Kuehn et al. |
| 6,743,240 | B2 | 6/2004 | Smith et al. |
| 6,749,560 | B1 | 6/2004 | Konstorum et al. |
| 6,749,609 | B1 | 6/2004 | Lunsford et al. |
| 6,752,768 | B2 | 6/2004 | Burdorff et al. |
| 6,752,811 | B2 | 6/2004 | Chu et al. |
| 6,752,822 | B2 | 6/2004 | Jespersen |
| 6,758,857 | B2 | 7/2004 | Cioanta et al. |
| 6,761,685 | B2 | 7/2004 | Adams et al. |
| 6,761,718 | B2 | 7/2004 | Madsen |
| 6,761,722 | B2 | 7/2004 | Cole et al. |
| 6,767,356 | B2 | 7/2004 | Kanner et al. |

(56) References Cited

U.S. PATENT DOCUMENTS

| | | |
|---|---|---|
| 6,773,434 B2 | 8/2004 | Ciarrocca |
| 6,776,165 B2 | 8/2004 | Jin |
| 6,776,787 B2 | 8/2004 | Phung et al. |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,382 B1 | 9/2004 | Hoffman |
| 6,786,864 B2 | 9/2004 | Matsuura et al. |
| 6,786,905 B2 | 9/2004 | Swanson et al. |
| 6,788,977 B2 | 9/2004 | Fenn et al. |
| 6,790,173 B2 | 9/2004 | Saadat et al. |
| 6,790,217 B2 | 9/2004 | Schulze et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,817,974 B2 | 11/2004 | Cooper et al. |
| 6,818,007 B1 | 11/2004 | Dampney et al. |
| 6,824,548 B2 | 11/2004 | Smith et al. |
| 6,830,545 B2 | 12/2004 | Bendall |
| 6,836,688 B2 | 12/2004 | Ingle et al. |
| 6,837,847 B2 | 1/2005 | Ewers et al. |
| 6,840,246 B2 | 1/2005 | Downing |
| 6,840,938 B1 | 1/2005 | Morley et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,866,628 B2 | 3/2005 | Goodman et al. |
| 6,869,394 B2 | 3/2005 | Ishibiki |
| 6,878,106 B1 | 4/2005 | Herrmann |
| 6,878,110 B2 | 4/2005 | Yang et al. |
| 6,881,213 B2 | 4/2005 | Ryan et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,890,295 B2 | 5/2005 | Michels et al. |
| 6,896,683 B1 | 5/2005 | Gadberry et al. |
| 6,896,692 B2 | 5/2005 | Ginn et al. |
| 6,899,710 B2 | 5/2005 | Hooven |
| 6,908,427 B2 | 6/2005 | Fleener et al. |
| 6,908,476 B2 | 6/2005 | Jud et al. |
| 6,913,613 B2 | 7/2005 | Schwarz et al. |
| 6,916,284 B2 | 7/2005 | Moriyama |
| 6,918,871 B2 | 7/2005 | Schulze |
| 6,918,906 B2 | 7/2005 | Long |
| 6,918,908 B2 | 7/2005 | Bonner et al. |
| 6,926,723 B1 | 8/2005 | Mulhauser et al. |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,932,834 B2 | 8/2005 | Lizardi et al. |
| 6,936,003 B2 | 8/2005 | Iddan |
| 6,939,290 B2 | 9/2005 | Iddan |
| 6,939,292 B2 | 9/2005 | Mizuno |
| 6,939,327 B2 | 9/2005 | Hall et al. |
| 6,939,347 B2 | 9/2005 | Thompson |
| 6,942,613 B2 | 9/2005 | Ewers et al. |
| 6,944,490 B1 | 9/2005 | Chow |
| 6,945,472 B2 | 9/2005 | Wuttke et al. |
| 6,945,979 B2 | 9/2005 | Kortenbach et al. |
| 6,949,096 B2 | 9/2005 | Davison et al. |
| 6,955,641 B2 | 10/2005 | Lubock |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,960,183 B2 | 11/2005 | Nicolette |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,980,858 B2 | 12/2005 | Fuimaono et al. |
| 6,984,203 B2 | 1/2006 | Tartaglia et al. |
| 6,984,205 B2 | 1/2006 | Gazdzinski |
| 6,986,738 B2 | 1/2006 | Glukhovsky et al. |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,602 B2 | 1/2006 | Nakazawa et al. |
| 6,991,627 B2 | 1/2006 | Madhani et al. |
| 6,991,631 B2 | 1/2006 | Woloszko et al. |
| 6,994,706 B2 | 2/2006 | Chornenky et al. |
| 6,994,708 B2 | 2/2006 | Manzo |
| 6,997,870 B2 | 2/2006 | Couvillon, Jr. |
| 6,997,931 B2 | 2/2006 | Sauer et al. |
| 7,000,818 B2 | 2/2006 | Shelton, IV et al. |
| 7,001,329 B2 | 2/2006 | Kobayashi et al. |
| 7,001,341 B2 | 2/2006 | Gellman et al. |
| 7,008,375 B2 | 3/2006 | Weisel |
| 7,008,419 B2 | 3/2006 | Shadduck |
| 7,009,634 B2 | 3/2006 | Iddan et al. |
| 7,010,340 B2 | 3/2006 | Scarantino et al. |
| 7,011,669 B2 | 3/2006 | Kimblad |
| 7,018,373 B2 | 3/2006 | Suzuki |
| 7,020,531 B1 | 3/2006 | Colliou et al. |
| 7,025,580 B2 | 4/2006 | Heagy et al. |
| 7,025,721 B2 | 4/2006 | Cohen et al. |
| 7,029,435 B2 | 4/2006 | Nakao |
| 7,029,438 B2 | 4/2006 | Morin et al. |
| 7,029,450 B2 | 4/2006 | Gellman |
| 7,032,600 B2 | 4/2006 | Fukuda et al. |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,454 B2 | 5/2006 | Taylor |
| 7,052,489 B2 | 5/2006 | Griego et al. |
| 7,056,330 B2 | 6/2006 | Gayton |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,559 B2 | 7/2006 | Adams et al. |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,010 B2 | 8/2006 | Ootawara et al. |
| 7,087,071 B2 | 8/2006 | Nicholas et al. |
| 7,088,923 B2 | 8/2006 | Haruyama |
| 7,090,673 B2 | 8/2006 | Dycus et al. |
| 7,090,683 B2 | 8/2006 | Brock et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,696 B2 | 9/2006 | Daniel et al. |
| 7,108,703 B2 | 9/2006 | Danitz et al. |
| 7,112,208 B2 | 9/2006 | Morris et al. |
| 7,115,092 B2 | 10/2006 | Park et al. |
| 7,115,124 B1 | 10/2006 | Xiao |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| 7,130,697 B2 | 10/2006 | Chornenky et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |

(56) References Cited

U.S. PATENT DOCUMENTS

| | | |
|---|---|---|
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,150,655 B2 | 12/2006 | Mastrototaro et al. |
| 7,150,750 B2 | 12/2006 | Damarati |
| 7,152,488 B2 | 12/2006 | Hedrich et al. |
| 7,153,321 B2 | 12/2006 | Andrews |
| 7,156,845 B2 | 1/2007 | Mulier et al. |
| 7,160,296 B2 | 1/2007 | Pearson et al. |
| 7,163,525 B2 | 1/2007 | Franer |
| 7,169,104 B2 | 1/2007 | Ueda et al. |
| 7,172,714 B2 | 2/2007 | Jacobson |
| 7,175,591 B2 | 2/2007 | Kaladelfos |
| 7,179,254 B2 | 2/2007 | Pendekanti et al. |
| 7,186,265 B2 | 3/2007 | Sharkawy et al. |
| 7,188,627 B2 | 3/2007 | Nelson et al. |
| 7,195,612 B2 | 3/2007 | Van Sloten et al. |
| 7,195,631 B2 | 3/2007 | Dumbauld |
| 7,204,820 B2 | 4/2007 | Akahoshi |
| 7,207,997 B2 | 4/2007 | Shipp et al. |
| 7,208,005 B2 | 4/2007 | Frecker et al. |
| 7,211,089 B2 | 5/2007 | Kear et al. |
| 7,211,092 B2 | 5/2007 | Hughett |
| 7,220,227 B2 | 5/2007 | Sasaki et al. |
| 7,223,271 B2 | 5/2007 | Muramatsu et al. |
| 7,223,272 B2 | 5/2007 | Francere et al. |
| 7,229,438 B2 | 6/2007 | Young |
| 7,232,414 B2 | 6/2007 | Gonzalez |
| 7,232,445 B2 | 6/2007 | Kortenbach et al. |
| 7,235,089 B1 | 6/2007 | McGuckin, Jr. |
| 7,241,290 B2 | 7/2007 | Doyle et al. |
| 7,241,295 B2 | 7/2007 | Maguire et al. |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |
| 7,261,725 B2 | 8/2007 | Binmoeller |
| 7,270,663 B2 | 9/2007 | Nakao |
| 7,288,075 B2 | 10/2007 | Parihar et al. |
| 7,291,127 B2 | 11/2007 | Eidenschink |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,311,107 B2 | 12/2007 | Harel et al. |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,335,220 B2 | 2/2008 | Khosravi et al. |
| 7,341,554 B2 | 3/2008 | Sekine et al. |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,390,324 B2 | 6/2008 | Whalen et al. |
| 7,393,322 B2 | 7/2008 | Wenchell |
| 7,402,162 B2 | 7/2008 | Ouchi |
| 7,404,791 B2 | 7/2008 | Linares et al. |
| 7,410,483 B2 | 8/2008 | Danitz et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,229 B2 | 10/2008 | Wolf |
| 7,435,257 B2 | 10/2008 | Lashinski et al. |
| 7,441,507 B2 | 10/2008 | Teraura et al. |
| 7,442,166 B2 | 10/2008 | Huang et al. |
| 7,452,327 B2 | 11/2008 | Durgin et al. |
| 7,455,208 B2 | 11/2008 | Wales et al. |
| 7,455,675 B2 | 11/2008 | Schur et al. |
| 7,468,066 B2 | 12/2008 | Vargas et al. |
| 7,476,237 B2 | 1/2009 | Taniguchi et al. |
| 7,479,104 B2 | 1/2009 | Lau et al. |
| 7,485,093 B2 | 2/2009 | Glukhovsky |
| 7,488,295 B2 | 2/2009 | Burbank et al. |
| 7,494,499 B2 | 2/2009 | Nagase et al. |
| 7,497,867 B2 | 3/2009 | Lasner et al. |
| 7,498,950 B1 | 3/2009 | Ertas et al. |
| 7,507,200 B2 | 3/2009 | Okada |
| 7,507,239 B2 | 3/2009 | Shadduck |
| 7,510,107 B2 | 3/2009 | Timm et al. |
| 7,511,733 B2 | 3/2009 | Takizawa et al. |
| 7,515,953 B2 | 4/2009 | Madar et al. |
| 7,520,876 B2 | 4/2009 | Ressemann et al. |
| 7,524,281 B2 | 4/2009 | Chu et al. |
| 7,524,302 B2 | 4/2009 | Tower |
| 7,534,228 B2 | 5/2009 | Williams |
| 7,540,872 B2 | 6/2009 | Schechter et al. |
| 7,542,807 B2 | 6/2009 | Bertolero et al. |
| 7,544,203 B2 | 6/2009 | Chin et al. |
| 7,548,040 B2 | 6/2009 | Lee et al. |
| 7,549,564 B2 | 6/2009 | Boudreaux |
| 7,549,991 B2 | 6/2009 | Lu et al. |
| 7,549,998 B2 | 6/2009 | Braun |
| 7,553,278 B2 | 6/2009 | Kucklick |
| 7,553,298 B2 | 6/2009 | Hunt et al. |
| 7,559,452 B2 | 7/2009 | Wales et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,907 B2 | 7/2009 | Fuimaono et al. |
| 7,561,916 B2 | 7/2009 | Hunt et al. |
| 7,565,201 B2 | 7/2009 | Blackmore et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,591,781 B2 | 9/2009 | Hirata |
| 7,597,229 B2 | 10/2009 | Boudreaux et al. |
| 7,604,150 B2 | 10/2009 | Boudreaux |
| 7,608,083 B2 | 10/2009 | Lee et al. |
| 7,611,479 B2 | 11/2009 | Cragg et al. |
| 7,615,002 B2 | 11/2009 | Rothweiler et al. |
| 7,615,005 B2 | 11/2009 | Stefanchik et al. |
| 7,618,398 B2 | 11/2009 | Holman et al. |
| 7,618,437 B2 | 11/2009 | Nakao |
| 7,621,936 B2 | 11/2009 | Cragg et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,648,519 B2 | 1/2010 | Lee et al. |
| 7,650,742 B2 | 1/2010 | Ushijima |
| 7,651,483 B2 | 1/2010 | Byrum et al. |
| 7,651,509 B2 | 1/2010 | Bojarski et al. |
| 7,653,438 B2 | 1/2010 | Deem et al. |
| 7,654,431 B2 | 2/2010 | Hueil et al. |
| 7,655,004 B2 | 2/2010 | Long |
| 7,662,089 B2 | 2/2010 | Okada et al. |
| 7,666,180 B2 | 2/2010 | Holsten et al. |
| 7,666,203 B2 | 2/2010 | Chanduszko et al. |
| 7,670,282 B2 | 3/2010 | Mathis |
| 7,670,336 B2 | 3/2010 | Young et al. |
| 7,674,259 B2 | 3/2010 | Shadduck |
| 7,678,043 B2 | 3/2010 | Gilad |
| 7,680,543 B2 | 3/2010 | Azure |
| 7,684,599 B2 | 3/2010 | Horn et al. |
| 7,684,851 B2 | 3/2010 | Miyake et al. |
| 7,686,826 B2 | 3/2010 | Lee et al. |
| 7,697,970 B2 | 4/2010 | Uchiyama et al. |
| 7,699,835 B2 | 4/2010 | Lee et al. |
| 7,699,864 B2 | 4/2010 | Kick et al. |
| 7,713,189 B2 | 5/2010 | Hanke |
| 7,713,270 B2 | 5/2010 | Suzuki |
| 7,721,742 B2 | 5/2010 | Kalloo et al. |
| 7,736,374 B2 | 6/2010 | Vaughan et al. |
| 7,744,615 B2 | 6/2010 | Couture |

(56) References Cited

U.S. PATENT DOCUMENTS

| | | |
|---|---|---|
| 7,749,161 B2 | 7/2010 | Beckman et al. |
| 7,751,866 B2 | 7/2010 | Aoki et al. |
| 7,753,901 B2 | 7/2010 | Piskun et al. |
| 7,753,933 B2 | 7/2010 | Ginn et al. |
| 7,758,577 B2 | 7/2010 | Nobis et al. |
| 7,762,949 B2 | 7/2010 | Nakao |
| 7,762,998 B2 | 7/2010 | Birk et al. |
| 7,763,012 B2 | 7/2010 | Petrick et al. |
| 7,765,010 B2 | 7/2010 | Chornenky et al. |
| 7,766,896 B2 | 8/2010 | Kornkven Volk et al. |
| 7,770,584 B2 | 8/2010 | Danek et al. |
| 7,771,416 B2 | 8/2010 | Spivey et al. |
| 7,771,437 B2 | 8/2010 | Hogg et al. |
| 7,776,035 B2 | 8/2010 | Rick et al. |
| 7,780,683 B2 | 8/2010 | Roue et al. |
| 7,780,691 B2 | 8/2010 | Stefanchik |
| 7,784,663 B2 | 8/2010 | Shelton, IV |
| 7,794,409 B2 | 9/2010 | Damarati |
| 7,794,447 B2 | 9/2010 | Dann et al. |
| 7,794,458 B2 | 9/2010 | McIntyre et al. |
| 7,794,475 B2 | 9/2010 | Hess et al. |
| 7,798,386 B2 | 9/2010 | Schall et al. |
| 7,815,565 B2 | 10/2010 | Stefanchik et al. |
| 7,815,566 B2 | 10/2010 | Stefanchik et al. |
| 7,815,659 B2 | 10/2010 | Conlon et al. |
| 7,815,662 B2 | 10/2010 | Spivey et al. |
| 7,819,836 B2 | 10/2010 | Levine et al. |
| 7,828,186 B2 | 11/2010 | Wales |
| 7,833,156 B2 | 11/2010 | Williams et al. |
| 7,833,238 B2 | 11/2010 | Nakao |
| 7,837,615 B2 | 11/2010 | Le et al. |
| 7,842,028 B2 | 11/2010 | Lee |
| 7,842,068 B2 | 11/2010 | Ginn |
| 7,846,171 B2 | 12/2010 | Kullas et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,862,553 B2 | 1/2011 | Ewaschuk |
| 7,867,216 B2 | 1/2011 | Wahr et al. |
| 7,871,371 B2 | 1/2011 | Komiya et al. |
| 7,879,004 B2 | 2/2011 | Seibel et al. |
| 7,883,458 B2 | 2/2011 | Hamel |
| 7,887,530 B2 | 2/2011 | Zemlok et al. |
| 7,887,558 B2 | 2/2011 | Lin et al. |
| 7,892,220 B2 | 2/2011 | Faller et al. |
| 7,896,804 B2 | 3/2011 | Uchimura et al. |
| 7,896,887 B2 | 3/2011 | Rimbaugh et al. |
| 7,905,828 B2 | 3/2011 | Brock et al. |
| 7,909,809 B2 | 3/2011 | Scopton et al. |
| 7,914,513 B2 | 3/2011 | Voorhees, Jr. |
| 7,918,785 B2 | 4/2011 | Okada et al. |
| 7,918,869 B2 | 4/2011 | Saadat et al. |
| 7,922,743 B2 | 4/2011 | Heinrich et al. |
| 7,927,271 B2 | 4/2011 | Dimitriou et al. |
| 7,931,624 B2 | 4/2011 | Smith et al. |
| 7,937,143 B2 | 5/2011 | Demarais et al. |
| 7,945,332 B2 | 5/2011 | Schechter |
| 7,947,000 B2 | 5/2011 | Vargas et al. |
| 7,953,326 B2 | 5/2011 | Farr et al. |
| 7,955,298 B2 | 6/2011 | Carroll et al. |
| 7,959,627 B2 | 6/2011 | Utley et al. |
| 7,959,629 B2 | 6/2011 | Young et al. |
| 7,963,975 B2 | 6/2011 | Criscuolo |
| 7,965,180 B2 | 6/2011 | Koyama |
| 7,967,808 B2 | 6/2011 | Fitzgerald et al. |
| 7,969,473 B2 | 6/2011 | Kotoda |
| 7,972,330 B2 | 7/2011 | Alejandro et al. |
| 7,976,458 B2 | 7/2011 | Stefanchik et al. |
| 7,976,552 B2 | 7/2011 | Suzuki |
| 7,985,239 B2 | 7/2011 | Suzuki |
| 7,988,618 B2 | 8/2011 | Mikkaichi et al. |
| 7,988,685 B2 | 8/2011 | Ziaie et al. |
| 8,007,495 B2 | 8/2011 | McDaniel et al. |
| 8,021,362 B2 | 9/2011 | Deem et al. |
| 8,029,504 B2 | 10/2011 | Long |
| 8,034,046 B2 | 10/2011 | Eidenschink |
| 8,037,591 B2 | 10/2011 | Spivey et al. |
| 8,048,067 B2 | 11/2011 | Davalos et al. |
| 8,048,108 B2 | 11/2011 | Sibbitt et al. |
| 8,052,699 B1 | 11/2011 | Sherwinter |
| 8,057,510 B2 | 11/2011 | Ginn et al. |
| 8,062,306 B2 | 11/2011 | Nobis et al. |
| 8,062,311 B2 | 11/2011 | Litscher et al. |
| 8,066,632 B2 | 11/2011 | Dario et al. |
| 8,066,702 B2 | 11/2011 | Ritman, III et al. |
| 8,070,759 B2 | 12/2011 | Stefanchik et al. |
| 8,070,804 B2 | 12/2011 | Hyde et al. |
| 8,075,572 B2 | 12/2011 | Stefanchik et al. |
| 8,075,587 B2 | 12/2011 | Ginn |
| 8,088,062 B2 | 1/2012 | Zwolinski |
| 8,096,459 B2 | 1/2012 | Ortiz et al. |
| 8,096,941 B2 | 1/2012 | Fowler et al. |
| 8,100,922 B2 | 1/2012 | Griffith |
| 8,109,872 B2 | 2/2012 | Kennedy, II et al. |
| 8,114,072 B2 | 2/2012 | Long et al. |
| 8,114,119 B2 | 2/2012 | Spivey et al. |
| 8,118,821 B2 | 2/2012 | Mouw |
| 8,118,834 B1 | 2/2012 | Goraltchouk et al. |
| 8,131,371 B2 | 3/2012 | Demarals et al. |
| 8,147,424 B2 | 4/2012 | Kassab et al. |
| 8,157,813 B2 | 4/2012 | Ko et al. |
| 8,157,834 B2 | 4/2012 | Conlon |
| 8,172,772 B2 | 5/2012 | Zwolinski et al. |
| 8,182,414 B2 | 5/2012 | Handa et al. |
| 8,187,166 B2 | 5/2012 | Kuth et al. |
| 8,200,334 B1 | 6/2012 | Min et al. |
| 8,206,295 B2 | 6/2012 | Kaul |
| 8,211,125 B2 | 7/2012 | Spivey |
| 8,216,224 B2 | 7/2012 | Morris et al. |
| 8,221,310 B2 | 7/2012 | Saadat et al. |
| 8,221,411 B2 | 7/2012 | Francischelli et al. |
| 8,241,204 B2 | 8/2012 | Spivey |
| 8,251,068 B2 | 8/2012 | Schnell |
| 8,252,057 B2 | 8/2012 | Fox |
| 8,262,563 B2 | 9/2012 | Bakos et al. |
| 8,262,655 B2 | 9/2012 | Ghabrial et al. |
| 8,262,680 B2 | 9/2012 | Swain et al. |
| 8,267,854 B2 | 9/2012 | Asada et al. |
| 8,303,581 B2 | 11/2012 | Arts et al. |
| 8,308,738 B2 | 11/2012 | Nobis et al. |
| 8,317,806 B2 | 11/2012 | Coe et al. |
| 8,317,814 B2 | 11/2012 | Karasawa et al. |
| 8,328,836 B2 | 12/2012 | Conlon et al. |
| 8,337,394 B2 | 12/2012 | Vakharia |
| 8,337,492 B2 | 12/2012 | Kunis et al. |
| 8,343,041 B2 | 1/2013 | Byers et al. |
| 8,353,487 B2 | 1/2013 | Trusty et al. |
| 8,357,170 B2 | 1/2013 | Stefanchik |
| 8,359,093 B2 | 1/2013 | Wariar |
| 8,361,066 B2 | 1/2013 | Long et al. |
| 8,361,112 B2 | 1/2013 | Carroll, II et al. |
| 8,377,057 B2 | 2/2013 | Rick et al. |
| 8,403,926 B2 | 3/2013 | Nobis et al. |
| 8,409,200 B2 | 4/2013 | Holcomb et al. |
| 8,425,505 B2 | 4/2013 | Long |
| 8,430,811 B2 | 4/2013 | Hess et al. |
| 8,449,452 B2 | 5/2013 | Iddan et al. |
| 8,449,538 B2 | 5/2013 | Long |
| 8,454,594 B2 | 6/2013 | Demarais et al. |
| 8,475,359 B2 | 7/2013 | Asada et al. |
| 8,480,657 B2 | 7/2013 | Bakos |
| 8,480,689 B2 | 7/2013 | Spivey et al. |
| 8,485,968 B2 | 7/2013 | Weimer et al. |
| 8,496,574 B2 | 7/2013 | Trusty et al. |
| 8,500,697 B2 | 8/2013 | Kurth et al. |
| 8,506,564 B2 | 8/2013 | Long et al. |
| 8,512,335 B2 | 8/2013 | Cheng et al. |
| 8,523,939 B1 | 9/2013 | Hausen |
| 8,529,563 B2 | 9/2013 | Long et al. |
| 8,545,396 B2 | 10/2013 | Cover et al. |
| 8,568,410 B2 | 10/2013 | Vakharia et al. |
| 8,579,897 B2 | 11/2013 | Vakharia et al. |
| 8,608,652 B2 | 12/2013 | Voegele et al. |
| 8,623,011 B2 | 1/2014 | Spivey |

(56) References Cited

U.S. PATENT DOCUMENTS

| | | |
|---|---|---|
| 8,636,648 B2 | 1/2014 | Gazdzinski |
| 8,636,730 B2 | 1/2014 | Keppel |
| 8,640,940 B2 | 2/2014 | Ohdaira |
| 8,652,150 B2 | 2/2014 | Swain et al. |
| 8,668,686 B2 | 3/2014 | Govari et al. |
| 8,679,003 B2 | 3/2014 | Spivey |
| 8,727,967 B2 | 5/2014 | Weitzner |
| 8,747,401 B2 | 6/2014 | Gonzalez et al. |
| 8,753,335 B2 | 6/2014 | Moshe et al. |
| 8,771,173 B2 | 7/2014 | Fonger et al. |
| 8,771,260 B2 | 7/2014 | Conlon et al. |
| 8,828,031 B2 | 9/2014 | Fox et al. |
| 8,880,185 B2 | 11/2014 | Hastings et al. |
| 8,888,792 B2 | 11/2014 | Harris et al. |
| 8,906,035 B2 | 12/2014 | Zwolinski et al. |
| 8,911,452 B2 | 12/2014 | Skakoon et al. |
| 8,939,897 B2 | 1/2015 | Nobis |
| 8,986,199 B2 | 3/2015 | Weisenburgh, II et al. |
| 9,005,198 B2 | 4/2015 | Long et al. |
| 9,011,431 B2 | 4/2015 | Long et al. |
| 9,028,483 B2 | 5/2015 | Long et al. |
| 9,049,987 B2 | 6/2015 | Conlon et al. |
| 9,078,662 B2 | 7/2015 | Bakos et al. |
| 9,220,526 B2 | 12/2015 | Conlon |
| 9,226,772 B2 | 1/2016 | Fox |
| 9,233,241 B2 | 1/2016 | Long |
| 9,254,169 B2 | 2/2016 | Long et al. |
| 9,271,796 B2 | 3/2016 | Buysse et al. |
| 9,277,957 B2 | 3/2016 | Long et al. |
| 9,314,620 B2 | 4/2016 | Long et al. |
| 9,375,268 B2 | 6/2016 | Long |
| 9,427,255 B2 | 8/2016 | Griffith et al. |
| 2001/0023333 A1 | 9/2001 | Wise et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0029055 A1 | 3/2002 | Bonutti |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0082551 A1 | 6/2002 | Yachia et al. |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0165592 A1 | 11/2002 | Glukhovsky et al. |
| 2002/0173805 A1 | 11/2002 | Matsuno et al. |
| 2002/0183591 A1 | 12/2002 | Matsuura et al. |
| 2003/0014090 A1 | 1/2003 | Abrahamson |
| 2003/0018373 A1 | 1/2003 | Eckhardt et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0078471 A1 | 4/2003 | Foley et al. |
| 2003/0083681 A1 | 5/2003 | Moutafis et al. |
| 2003/0114731 A1 | 6/2003 | Cadeddu et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130564 A1 | 7/2003 | Martone et al. |
| 2003/0130656 A1 | 7/2003 | Levin |
| 2003/0139646 A1 | 7/2003 | Sharrow et al. |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0187351 A1 | 10/2003 | Franck et al. |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0024414 A1 | 2/2004 | Downing |
| 2004/0034369 A1 | 2/2004 | Sauer et al. |
| 2004/0054322 A1 | 3/2004 | Vargas |
| 2004/0098007 A1 | 5/2004 | Heiss |
| 2004/0101456 A1 | 5/2004 | Kuroshima et al. |
| 2004/0104999 A1 | 6/2004 | Okada |
| 2004/0116948 A1 | 6/2004 | Sixto, Jr. et al. |
| 2004/0127940 A1 | 7/2004 | Ginn et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0161451 A1 | 8/2004 | Pierce et al. |
| 2004/0167545 A1 | 8/2004 | Sadler et al. |
| 2004/0176699 A1 | 9/2004 | Walker et al. |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0199159 A1 | 10/2004 | Lee et al. |
| 2004/0206859 A1 | 10/2004 | Chong et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0225323 A1 | 11/2004 | Nagase et al. |
| 2004/0230095 A1 | 11/2004 | Stefanchik et al. |
| 2004/0230096 A1 | 11/2004 | Stefanchik et al. |
| 2004/0230161 A1 | 11/2004 | Zeiner |
| 2004/0243108 A1 | 12/2004 | Suzuki |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2004/0254572 A1 | 12/2004 | McIntyre et al. |
| 2004/0260198 A1 | 12/2004 | Rothberg et al. |
| 2004/0260315 A1 | 12/2004 | Dell et al. |
| 2004/0260337 A1 | 12/2004 | Freed |
| 2005/0004515 A1 | 1/2005 | Hart et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0059963 A1 | 3/2005 | Phan et al. |
| 2005/0059964 A1 | 3/2005 | Fitz |
| 2005/0065397 A1 | 3/2005 | Saadat et al. |
| 2005/0065509 A1 | 3/2005 | Coldwell et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0070947 A1 | 3/2005 | Franer et al. |
| 2005/0080413 A1 | 4/2005 | Canady |
| 2005/0080435 A1 | 4/2005 | Smith et al. |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0096502 A1 | 5/2005 | Khalili |
| 2005/0101837 A1 | 5/2005 | Kalloo et al. |
| 2005/0101838 A1 | 5/2005 | Camillocci et al. |
| 2005/0101984 A1 | 5/2005 | Chanduszko et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0119613 A1 | 6/2005 | Moenning et al. |

(56) References Cited

U.S. PATENT DOCUMENTS

| | | |
|---|---|---|
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216036 A1 | 9/2005 | Nakao |
| 2005/0216050 A1 | 9/2005 | Sepetka et al. |
| 2005/0228224 A1 | 10/2005 | Okada et al. |
| 2005/0228406 A1 | 10/2005 | Bose |
| 2005/0234297 A1 | 10/2005 | Devierre et al. |
| 2005/0240249 A1 | 10/2005 | Tu et al. |
| 2005/0250983 A1 | 11/2005 | Tremaglio et al. |
| 2005/0250987 A1 | 11/2005 | Ewers et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0274935 A1 | 12/2005 | Nelson |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0015131 A1 | 1/2006 | Kierce et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0058776 A1 | 3/2006 | Bilsbury |
| 2006/0064083 A1 | 3/2006 | Khalaj et al. |
| 2006/0069396 A1 | 3/2006 | Meade et al. |
| 2006/0069424 A1 | 3/2006 | Acosta et al. |
| 2006/0069425 A1 | 3/2006 | Hillis et al. |
| 2006/0069429 A1 | 3/2006 | Spence et al. |
| 2006/0074413 A1 | 4/2006 | Behzadian |
| 2006/0079890 A1 | 4/2006 | Guerra |
| 2006/0089528 A1 | 4/2006 | Tartaglia et al. |
| 2006/0095031 A1 | 5/2006 | Ormsby |
| 2006/0095060 A1 | 5/2006 | Mayenberger et al. |
| 2006/0100687 A1 | 5/2006 | Fahey et al. |
| 2006/0106423 A1 | 5/2006 | Weisel et al. |
| 2006/0111209 A1 | 5/2006 | Hinman et al. |
| 2006/0111210 A1 | 5/2006 | Hinman et al. |
| 2006/0111703 A1 | 5/2006 | Kunis et al. |
| 2006/0111704 A1 | 5/2006 | Brenneman et al. |
| 2006/0129166 A1 | 6/2006 | Lavelle |
| 2006/0135962 A1 | 6/2006 | Kick et al. |
| 2006/0135971 A1 | 6/2006 | Swanstrom et al. |
| 2006/0135984 A1 | 6/2006 | Kramer et al. |
| 2006/0142644 A1 | 6/2006 | Mulac et al. |
| 2006/0142652 A1 | 6/2006 | Keenan |
| 2006/0142790 A1 | 6/2006 | Gertner |
| 2006/0142798 A1 | 6/2006 | Holman et al. |
| 2006/0149129 A1 | 7/2006 | Watts et al. |
| 2006/0149131 A1 | 7/2006 | Or |
| 2006/0149132 A1 | 7/2006 | Iddan |
| 2006/0149135 A1 | 7/2006 | Paz |
| 2006/0161190 A1 | 7/2006 | Gadberry et al. |
| 2006/0167416 A1 | 7/2006 | Mathis et al. |
| 2006/0167482 A1 | 7/2006 | Swain et al. |
| 2006/0178560 A1 | 8/2006 | Saadat et al. |
| 2006/0183975 A1 | 8/2006 | Saadat et al. |
| 2006/0184161 A1 | 8/2006 | Maahs et al. |
| 2006/0189844 A1 | 8/2006 | Tien |
| 2006/0189845 A1 | 8/2006 | Maahs et al. |
| 2006/0190027 A1 | 8/2006 | Downey |
| 2006/0195084 A1 | 8/2006 | Slater |
| 2006/0200005 A1 | 9/2006 | Bjork et al. |
| 2006/0200121 A1 | 9/2006 | Mowery |
| 2006/0200169 A1 | 9/2006 | Sniffin |
| 2006/0200170 A1 | 9/2006 | Aranyi |
| 2006/0200199 A1 | 9/2006 | Bonutti et al. |
| 2006/0217665 A1 | 9/2006 | Prosek |
| 2006/0217697 A1 | 9/2006 | Lau et al. |
| 2006/0217742 A1 | 9/2006 | Messerly et al. |
| 2006/0217743 A1 | 9/2006 | Messerly et al. |
| 2006/0229639 A1 | 10/2006 | Whitfield |
| 2006/0229640 A1 | 10/2006 | Whitfield |
| 2006/0237022 A1 | 10/2006 | Chen et al. |
| 2006/0237023 A1 | 10/2006 | Cox et al. |
| 2006/0241570 A1 | 10/2006 | Wilk |
| 2006/0247500 A1 | 11/2006 | Voegele et al. |
| 2006/0247576 A1 | 11/2006 | Poncet |
| 2006/0247663 A1 | 11/2006 | Schwartz et al. |
| 2006/0247673 A1 | 11/2006 | Voegele et al. |
| 2006/0253004 A1 | 11/2006 | Frisch et al. |
| 2006/0253039 A1 | 11/2006 | McKenna et al. |
| 2006/0258907 A1 | 11/2006 | Stefanchik et al. |
| 2006/0258908 A1 | 11/2006 | Stefanchik et al. |
| 2006/0258910 A1 | 11/2006 | Stefanchik et al. |
| 2006/0258954 A1 | 11/2006 | Timberlake et al. |
| 2006/0258955 A1 | 11/2006 | Hoffman et al. |
| 2006/0259010 A1 | 11/2006 | Stefanchik et al. |
| 2006/0259073 A1 | 11/2006 | Miyamoto et al. |
| 2006/0264752 A1 | 11/2006 | Rubinsky et al. |
| 2006/0264904 A1 | 11/2006 | Kerby et al. |
| 2006/0264930 A1 | 11/2006 | Nishimura |
| 2006/0270902 A1 | 11/2006 | Igarashi et al. |
| 2006/0271042 A1 | 11/2006 | Latterell et al. |
| 2006/0271102 A1 | 11/2006 | Bosshard et al. |
| 2006/0276835 A1 | 12/2006 | Uchida |
| 2006/0281970 A1 | 12/2006 | Stokes et al. |
| 2006/0282106 A1 | 12/2006 | Cole et al. |
| 2006/0285732 A1 | 12/2006 | Horn et al. |
| 2006/0287644 A1 | 12/2006 | Inganas et al. |
| 2006/0287666 A1 | 12/2006 | Saadat et al. |
| 2006/0293626 A1 | 12/2006 | Byrum et al. |
| 2007/0000550 A1 | 1/2007 | Osinski |
| 2007/0002135 A1 | 1/2007 | Glukhovsky |
| 2007/0005019 A1 | 1/2007 | Okishige |
| 2007/0010801 A1 | 1/2007 | Chen et al. |
| 2007/0015965 A1 | 1/2007 | Cox et al. |
| 2007/0027469 A1 | 2/2007 | Smith et al. |
| 2007/0032700 A1 | 2/2007 | Fowler et al. |
| 2007/0032701 A1 | 2/2007 | Fowler et al. |
| 2007/0043261 A1 | 2/2007 | Watanabe et al. |
| 2007/0049800 A1 | 3/2007 | Boulais |

(56) References Cited

U.S. PATENT DOCUMENTS

| | | |
|---|---|---|
| 2007/0049902 A1 | 3/2007 | Griffin et al. |
| 2007/0049968 A1 | 3/2007 | Sibbit et al. |
| 2007/0051375 A1 | 3/2007 | Milliman |
| 2007/0060880 A1 | 3/2007 | Gregorich et al. |
| 2007/0066869 A1 | 3/2007 | Hoffman |
| 2007/0067017 A1 | 3/2007 | Trapp |
| 2007/0073102 A1 | 3/2007 | Matsuno et al. |
| 2007/0073269 A1 | 3/2007 | Becker |
| 2007/0078439 A1 | 4/2007 | Grandt et al. |
| 2007/0079924 A1 | 4/2007 | Saadat et al. |
| 2007/0083192 A1 | 4/2007 | Welch et al. |
| 2007/0083195 A1 | 4/2007 | Werneth et al. |
| 2007/0088370 A1 | 4/2007 | Kahle et al. |
| 2007/0100375 A1 | 5/2007 | Mikkaichi et al. |
| 2007/0100376 A1 | 5/2007 | Mikkaichi et al. |
| 2007/0106113 A1 | 5/2007 | Ravo |
| 2007/0106118 A1 | 5/2007 | Moriyama |
| 2007/0106317 A1 | 5/2007 | Shelton, IV et al. |
| 2007/0112251 A1 | 5/2007 | Nakhuda |
| 2007/0112331 A1 | 5/2007 | Weber et al. |
| 2007/0112342 A1 | 5/2007 | Pearson et al. |
| 2007/0112383 A1 | 5/2007 | Conlon et al. |
| 2007/0112385 A1 | 5/2007 | Conlon |
| 2007/0112417 A1 | 5/2007 | Shanley et al. |
| 2007/0112425 A1 | 5/2007 | Schaller et al. |
| 2007/0118115 A1 | 5/2007 | Artale et al. |
| 2007/0123840 A1 | 5/2007 | Cox |
| 2007/0129605 A1 | 6/2007 | Schaaf |
| 2007/0129719 A1 | 6/2007 | Kendale et al. |
| 2007/0129760 A1 | 6/2007 | Demarais et al. |
| 2007/0135709 A1 | 6/2007 | Rioux et al. |
| 2007/0135803 A1 | 6/2007 | Belson |
| 2007/0142706 A1 | 6/2007 | Matsui et al. |
| 2007/0142710 A1 | 6/2007 | Yokoi et al. |
| 2007/0142779 A1 | 6/2007 | Duane et al. |
| 2007/0142780 A1 | 6/2007 | Van Lue |
| 2007/0154460 A1 | 7/2007 | Kraft et al. |
| 2007/0156028 A1 | 7/2007 | Van Lue et al. |
| 2007/0156116 A1 | 7/2007 | Gonzalez |
| 2007/0156127 A1 | 7/2007 | Rioux et al. |
| 2007/0161855 A1 | 7/2007 | Mikkaichi et al. |
| 2007/0162101 A1 | 7/2007 | Burgermeister et al. |
| 2007/0167901 A1 | 7/2007 | Herrig et al. |
| 2007/0173686 A1 | 7/2007 | Lin et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0179530 A1 | 8/2007 | Tieu et al. |
| 2007/0191904 A1 | 8/2007 | Libbus et al. |
| 2007/0197865 A1 | 8/2007 | Miyake et al. |
| 2007/0198057 A1 | 8/2007 | Gelbart et al. |
| 2007/0203398 A1 | 8/2007 | Bonadio et al. |
| 2007/0203487 A1 | 8/2007 | Sugita |
| 2007/0208336 A1 | 9/2007 | Kim et al. |
| 2007/0208364 A1 | 9/2007 | Smith et al. |
| 2007/0208407 A1 | 9/2007 | Gerdts et al. |
| 2007/0213754 A1 | 9/2007 | Mikkaichi et al. |
| 2007/0225552 A1 | 9/2007 | Segawa et al. |
| 2007/0225554 A1 | 9/2007 | Maseda et al. |
| 2007/0233040 A1 | 10/2007 | Macnamara et al. |
| 2007/0244356 A1 | 10/2007 | Carrillo, Jr. et al. |
| 2007/0244358 A1 | 10/2007 | Lee |
| 2007/0250038 A1 | 10/2007 | Boulais |
| 2007/0250057 A1 | 10/2007 | Nobis et al. |
| 2007/0255096 A1 | 11/2007 | Stefanchik et al. |
| 2007/0255100 A1 | 11/2007 | Barlow et al. |
| 2007/0255273 A1 | 11/2007 | Fernandez et al. |
| 2007/0255303 A1 | 11/2007 | Bakos et al. |
| 2007/0255306 A1 | 11/2007 | Conlon et al. |
| 2007/0260112 A1 | 11/2007 | Rahmani |
| 2007/0260117 A1 | 11/2007 | Zwolinski et al. |
| 2007/0260121 A1 | 11/2007 | Bakos et al. |
| 2007/0260242 A1 | 11/2007 | Dycus et al. |
| 2007/0260273 A1 | 11/2007 | Cropper et al. |
| 2007/0260302 A1 | 11/2007 | Igaki |
| 2007/0265494 A1 | 11/2007 | Leanna et al. |
| 2007/0270629 A1 | 11/2007 | Charles |
| 2007/0270889 A1 | 11/2007 | Conlon et al. |
| 2007/0270895 A1 | 11/2007 | Nobis et al. |
| 2007/0270907 A1 | 11/2007 | Stokes et al. |
| 2007/0282165 A1 | 12/2007 | Hopkins et al. |
| 2007/0282371 A1 | 12/2007 | Lee et al. |
| 2007/0293727 A1 | 12/2007 | Goldfarb et al. |
| 2007/0299387 A1 | 12/2007 | Williams et al. |
| 2008/0004650 A1 | 1/2008 | George |
| 2008/0015409 A1 | 1/2008 | Barlow et al. |
| 2008/0015413 A1 | 1/2008 | Barlow et al. |
| 2008/0015552 A1 | 1/2008 | Doyle et al. |
| 2008/0021416 A1 | 1/2008 | Arai et al. |
| 2008/0022927 A1 | 1/2008 | Zhang et al. |
| 2008/0027387 A1 | 1/2008 | Grabinsky |
| 2008/0033244 A1 | 2/2008 | Matsui et al. |
| 2008/0033451 A1 | 2/2008 | Rieber et al. |
| 2008/0051629 A1 | 2/2008 | Sugiyama et al. |
| 2008/0051735 A1 | 2/2008 | Measamer et al. |
| 2008/0058586 A1 | 3/2008 | Karpiel |
| 2008/0058854 A1 | 3/2008 | Kieturakis et al. |
| 2008/0065169 A1 | 3/2008 | Colliou et al. |
| 2008/0071264 A1 | 3/2008 | Azure |
| 2008/0086172 A1 | 4/2008 | Martin et al. |
| 2008/0091068 A1 | 4/2008 | Terliuc |
| 2008/0097159 A1 | 4/2008 | Ishiguro |
| 2008/0097472 A1 | 4/2008 | Agmon et al. |
| 2008/0097483 A1 | 4/2008 | Ortiz et al. |
| 2008/0103527 A1 | 5/2008 | Martin et al. |
| 2008/0114384 A1 | 5/2008 | Chang et al. |
| 2008/0119870 A1 | 5/2008 | Williams |
| 2008/0119891 A1 | 5/2008 | Miles et al. |
| 2008/0125765 A1 | 5/2008 | Berenshteyn et al. |
| 2008/0125774 A1 | 5/2008 | Palanker et al. |
| 2008/0125796 A1 | 5/2008 | Graham |
| 2008/0132892 A1 | 6/2008 | Lunsford et al. |
| 2008/0139882 A1 | 6/2008 | Fujimori |
| 2008/0140069 A1 | 6/2008 | Filloux et al. |
| 2008/0140071 A1 | 6/2008 | Vegesna |
| 2008/0147056 A1 | 6/2008 | van der Weide et al. |
| 2008/0150754 A1 | 6/2008 | Quendt |
| 2008/0171907 A1 | 7/2008 | Long et al. |
| 2008/0177135 A1 | 7/2008 | Muyari et al. |
| 2008/0188710 A1 | 8/2008 | Segawa et al. |
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200933 A1 | 8/2008 | Bakos et al. |
| 2008/0200934 A1 | 8/2008 | Fox |
| 2008/0208189 A1 | 8/2008 | Van Wyk et al. |
| 2008/0208213 A1 | 8/2008 | Benjamin et al. |
| 2008/0208280 A1 | 8/2008 | Lindenthaler et al. |
| 2008/0214890 A1 | 9/2008 | Motai et al. |
| 2008/0221587 A1 | 9/2008 | Schwartz |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0249567 A1 | 10/2008 | Kaplan |
| 2008/0255633 A1 | 10/2008 | Behl et al. |
| 2008/0262513 A1 | 10/2008 | Stahler et al. |
| 2008/0262524 A1 | 10/2008 | Bangera et al. |
| 2008/0262540 A1 | 10/2008 | Bangera et al. |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287801 A1 | 11/2008 | Magnin et al. |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0300571 A1 | 12/2008 | LePivert |
| 2008/0306493 A1 | 12/2008 | Shibata et al. |
| 2008/0309758 A1 | 12/2008 | Karasawa et al. |

(56) References Cited

U.S. PATENT DOCUMENTS

| | | |
|---|---|---|
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0005636 A1 | 1/2009 | Pang et al. |
| 2009/0030278 A1 | 1/2009 | Minakuchi |
| 2009/0054728 A1 | 2/2009 | Trusty |
| 2009/0062788 A1* | 3/2009 | Long ............ A61B 18/14 606/41 |
| 2009/0062795 A1 | 3/2009 | Vakharia et al. |
| 2009/0069634 A1 | 3/2009 | Larkin |
| 2009/0076499 A1 | 3/2009 | Azure |
| 2009/0078736 A1 | 3/2009 | Van Lue |
| 2009/0082627 A1 | 3/2009 | Karasawa et al. |
| 2009/0082776 A1 | 3/2009 | Cresina |
| 2009/0082779 A1 | 3/2009 | Nakao |
| 2009/0093690 A1 | 4/2009 | Yoshizawa |
| 2009/0112059 A1 | 4/2009 | Nobis |
| 2009/0112063 A1 | 4/2009 | Bakos et al. |
| 2009/0125042 A1 | 5/2009 | Mouw |
| 2009/0131751 A1 | 5/2009 | Spivey et al. |
| 2009/0143639 A1 | 6/2009 | Stark |
| 2009/0143649 A1 | 6/2009 | Rossi |
| 2009/0143794 A1 | 6/2009 | Conlon et al. |
| 2009/0143818 A1 | 6/2009 | Faller et al. |
| 2009/0149710 A1 | 6/2009 | Stefanchik et al. |
| 2009/0163770 A1 | 6/2009 | Torrie et al. |
| 2009/0177031 A1 | 7/2009 | Surti et al. |
| 2009/0177219 A1 | 7/2009 | Conlon |
| 2009/0182325 A1 | 7/2009 | Werneth et al. |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198212 A1 | 8/2009 | Timberlake et al. |
| 2009/0198231 A1 | 8/2009 | Esser et al. |
| 2009/0198253 A1 | 8/2009 | Omori |
| 2009/0209990 A1 | 8/2009 | Yates et al. |
| 2009/0210000 A1 | 8/2009 | Sullivan et al. |
| 2009/0216248 A1 | 8/2009 | Uenohara et al. |
| 2009/0221873 A1 | 9/2009 | McGrath |
| 2009/0227999 A1 | 9/2009 | Willis et al. |
| 2009/0228001 A1 | 9/2009 | Pacey |
| 2009/0248055 A1 | 10/2009 | Spivey et al. |
| 2009/0259105 A1 | 10/2009 | Miyano et al. |
| 2009/0269317 A1 | 10/2009 | Davalos |
| 2009/0281559 A1 | 11/2009 | Swain et al. |
| 2009/0287206 A1 | 11/2009 | Jun |
| 2009/0287236 A1 | 11/2009 | Bakos et al. |
| 2009/0292164 A1 | 11/2009 | Yamatani |
| 2009/0292167 A1 | 11/2009 | Kimoto |
| 2009/0306470 A1 | 12/2009 | Karasawa et al. |
| 2009/0322864 A1 | 12/2009 | Karasawa et al. |
| 2009/0326332 A1 | 12/2009 | Carter |
| 2010/0010294 A1 | 1/2010 | Conlon et al. |
| 2010/0010298 A1 | 1/2010 | Bakos et al. |
| 2010/0010303 A1 | 1/2010 | Bakos |
| 2010/0023032 A1 | 1/2010 | Granja Filho |
| 2010/0030211 A1 | 2/2010 | Davalos et al. |
| 2010/0036198 A1 | 2/2010 | Tacchino et al. |
| 2010/0042045 A1 | 2/2010 | Spivey |
| 2010/0048990 A1 | 2/2010 | Bakos |
| 2010/0049223 A1 | 2/2010 | Granja Filho |
| 2010/0056862 A1 | 3/2010 | Bakos |
| 2010/0056864 A1 | 3/2010 | Lee |
| 2010/0076451 A1 | 3/2010 | Zwolinski et al. |
| 2010/0076460 A1 | 3/2010 | Taylor et al. |
| 2010/0081875 A1 | 4/2010 | Fowler et al. |
| 2010/0091128 A1 | 4/2010 | Ogasawara et al. |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0152539 A1 | 6/2010 | Ghabrial et al. |
| 2010/0152725 A1 | 6/2010 | Pearson et al. |
| 2010/0152746 A1 | 6/2010 | Ceniccola et al. |
| 2010/0191050 A1 | 7/2010 | Zwolinski |
| 2010/0191267 A1 | 7/2010 | Fox |
| 2010/0198248 A1 | 8/2010 | Vakharia |
| 2010/0198254 A1 | 8/2010 | Schaeffer |
| 2010/0210906 A1 | 8/2010 | Wendlandt |
| 2010/0217367 A1 | 8/2010 | Belson |
| 2010/0249700 A1 | 9/2010 | Spivey |
| 2010/0256628 A1 | 10/2010 | Pearson et al. |
| 2010/0261994 A1 | 10/2010 | Davalos et al. |
| 2010/0268025 A1 | 10/2010 | Belson |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331758 A1 | 12/2010 | Davalos et al. |
| 2011/0077476 A1 | 3/2011 | Rofougaran |
| 2011/0087224 A1 | 4/2011 | Cadeddu et al. |
| 2011/0087266 A1 | 4/2011 | Conlon et al. |
| 2011/0087267 A1 | 4/2011 | Spivey et al. |
| 2011/0093009 A1 | 4/2011 | Fox |
| 2011/0098694 A1 | 4/2011 | Long |
| 2011/0098704 A1 | 4/2011 | Long et al. |
| 2011/0106221 A1 | 5/2011 | Neal, II et al. |
| 2011/0112434 A1 | 5/2011 | Ghabrial et al. |
| 2011/0112527 A1 | 5/2011 | Hamilton, Jr. et al. |
| 2011/0115891 A1 | 5/2011 | Trusty |
| 2011/0152610 A1 | 6/2011 | Trusty et al. |
| 2011/0152878 A1 | 6/2011 | Trusty et al. |
| 2011/0152888 A1 | 6/2011 | Ho et al. |
| 2011/0152923 A1 | 6/2011 | Fox |
| 2011/0160514 A1 | 6/2011 | Long et al. |
| 2011/0190764 A1 | 8/2011 | Long et al. |
| 2011/0193948 A1 | 8/2011 | Amling et al. |
| 2011/0224665 A1 | 9/2011 | Crosby et al. |
| 2011/0245619 A1 | 10/2011 | Holcomb |
| 2011/0282149 A1 | 11/2011 | Vargas et al. |
| 2011/0284014 A1 | 11/2011 | Cadeddu et al. |
| 2011/0285488 A1 | 11/2011 | Scott et al. |
| 2012/0004502 A1 | 1/2012 | Weitzner et al. |
| 2012/0029335 A1 | 2/2012 | Sudam et al. |
| 2012/0078266 A1 | 3/2012 | Tyson, Jr. |
| 2012/0088965 A1 | 4/2012 | Stokes et al. |
| 2012/0089089 A1 | 4/2012 | Swain et al. |
| 2012/0089093 A1 | 4/2012 | Trusty |
| 2012/0101331 A1 | 4/2012 | Gilad et al. |
| 2012/0101413 A1 | 4/2012 | Beetel et al. |
| 2012/0109122 A1 | 5/2012 | Arena et al. |
| 2012/0116155 A1 | 5/2012 | Trusty |
| 2012/0116266 A1 | 5/2012 | Houser et al. |
| 2012/0149981 A1 | 6/2012 | Khait et al. |
| 2012/0150172 A1 | 6/2012 | Ortiz et al. |
| 2012/0191075 A1 | 7/2012 | Trusty |
| 2012/0191076 A1 | 7/2012 | Voegele et al. |
| 2012/0239082 A1 | 9/2012 | Shelton, IV et al. |
| 2012/0289857 A1 | 11/2012 | Toth et al. |
| 2013/0030430 A1 | 1/2013 | Stewart et al. |
| 2013/0090666 A1 | 4/2013 | Hess et al. |
| 2013/0138091 A1 | 5/2013 | Coe et al. |
| 2013/0158348 A1 | 6/2013 | Nobis et al. |
| 2013/0172672 A1 | 7/2013 | Iddan et al. |
| 2013/0231530 A1 | 9/2013 | Lien et al. |
| 2013/0245356 A1 | 9/2013 | Fernandez et al. |
| 2013/0331646 A1 | 12/2013 | Pell et al. |
| 2013/0331649 A1 | 12/2013 | Khait et al. |
| 2014/0031813 A1 | 1/2014 | Tellio et al. |
| 2014/0039491 A1 | 2/2014 | Bakos et al. |
| 2014/0039492 A1 | 2/2014 | Long |
| 2014/0052216 A1 | 2/2014 | Long et al. |
| 2014/0121678 A1 | 5/2014 | Trusty et al. |
| 2014/0243597 A1 | 8/2014 | Weisenburgh, II et al. |
| 2014/0343360 A1 | 11/2014 | Shohat et al. |
| 2015/0032132 A1 | 1/2015 | Harris et al. |
| 2015/0230858 A1 | 8/2015 | Long et al. |
| 2015/0265335 A1 | 9/2015 | Bakos et al. |
| 2015/0265342 A1 | 9/2015 | Long et al. |
| 2015/0374444 A1 | 12/2015 | Conlon et al. |
| 2016/0074056 A1 | 3/2016 | Conlon |
| 2016/0100879 A1 | 4/2016 | Long |

(56) References Cited

U.S. PATENT DOCUMENTS

| | | |
|---|---|---|
| 2016/0128759 A1 | 5/2016 | Long et al. |
| 2016/0166311 A1 | 6/2016 | Long et al. |
| 2016/0296280 A1 | 10/2016 | Long |

FOREIGN PATENT DOCUMENTS

| | | |
|---|---|---|
| DE | 4323585 A1 | 1/1995 |
| DE | 19713797 A1 | 10/1997 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0499491 A2 | 8/1992 |
| EP | 0589454 A2 | 3/1994 |
| EP | 0464479 B1 | 3/1995 |
| EP | 0529675 B1 | 2/1996 |
| EP | 0773003 A1 | 5/1997 |
| EP | 0621009 B1 | 7/1997 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 0941128 B1 | 10/2004 |
| EP | 1411843 B1 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1582138 B1 | 9/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 0723462 B1 | 3/2009 |
| EP | 1769749 B1 | 11/2009 |
| EP | 2135545 A2 | 12/2009 |
| EP | 1493397 B1 | 9/2011 |
| EP | 2659847 A1 | 11/2013 |
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | 56-46674 | 4/1981 |
| JP | S 63309252 A | 12/1988 |
| JP | H 04-38960 A | 2/1992 |
| JP | H 06-269460 A | 9/1994 |
| JP | H 08-29699 A | 2/1996 |
| JP | H 9-75365 A | 3/1997 |
| JP | H 10-24049 A | 1/1998 |
| JP | 3007713 B2 | 2/2000 |
| JP | 2000-107197 A | 4/2000 |
| JP | 2000245683 A | 9/2000 |
| JP | 2001-526072 A | 12/2001 |
| JP | 2002-369791 A | 12/2002 |
| JP | 2003-088494 A | 3/2003 |
| JP | 2003-235852 A | 8/2003 |
| JP | 2004-033525 A | 2/2004 |
| JP | 2004-065745 A | 3/2004 |
| JP | 2005-121947 A | 5/2005 |
| JP | 2005-261514 A | 9/2005 |
| JP | 2005-296063 A | 10/2005 |
| JP | 2006-517843 A | 8/2006 |
| JP | 2006297005 A | 11/2006 |
| JP | 2006-343510 A | 12/2006 |
| JP | 2007-020806 A | 2/2007 |
| JP | 2007-125264 A | 5/2007 |
| JP | 2007-516792 A | 6/2007 |
| JP | 2010/503496 A | 2/2010 |
| JP | 2012-515018 A | 7/2012 |
| NL | 1021295 C2 | 2/2004 |
| SU | 194230 | 5/1967 |
| SU | 980703 | 12/1982 |
| WO | WO 84/01707 A1 | 5/1984 |
| WO | WO 86/07543 A1 | 12/1986 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 94/22383 A1 | 10/1994 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/00060 A1 | 1/1999 |
| WO | WO 99/09919 A1 | 3/1999 |
| WO | WO 99/17661 A1 | 4/1999 |
| WO | WO 99/30622 A2 | 6/1999 |
| WO | WO 00/22996 A1 | 4/2000 |
| WO | WO 00/35358 A1 | 6/2000 |
| WO | WO 00/68665 A1 | 11/2000 |
| WO | WO 01/10319 A1 | 2/2001 |
| WO | WO 01/26708 A1 | 4/2001 |
| WO | WO 01/41627 A2 | 6/2001 |
| WO | WO 01/58360 A2 | 8/2001 |
| WO | WO 02/11621 A2 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/081761 A2 | 10/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A2 | 5/2004 |
| WO | WO 2004/037149 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2005/122866 A1 | 12/2005 |
| WO | WO 2006/007399 A1 | 1/2006 |
| WO | WO 2006/012630 A2 | 2/2006 |
| WO | WO 2006/040109 A1 | 4/2006 |
| WO | WO 2006/041881 A2 | 4/2006 |

(56) References Cited

FOREIGN PATENT DOCUMENTS

| | | |
|---|---|---|
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/035537 A2 | 3/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2007/135577 A2 | 11/2007 |
| WO | WO 2007/143200 A2 | 12/2007 |
| WO | WO 2007/144004 A1 | 12/2007 |
| WO | WO 2008/005433 A1 | 1/2008 |
| WO | WO 2008/033356 A2 | 3/2008 |
| WO | WO 2008/034103 A2 | 3/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/080062 A2 | 7/2008 |
| WO | WO 2008/101075 A2 | 8/2008 |
| WO | WO 2008/101086 A2 | 8/2008 |
| WO | WO 2008/102154 A2 | 8/2008 |
| WO | WO 2008/108863 A2 | 9/2008 |
| WO | WO 2008/151237 A1 | 12/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/036457 A1 | 3/2009 |
| WO | WO 2009/121017 A1 | 10/2009 |
| WO | WO 2009/132190 A2 | 10/2009 |
| WO | WO 2010/027688 A1 | 3/2010 |
| WO | WO 2010/056716 A2 | 5/2010 |
| WO | WO 2010/080974 A1 | 7/2010 |
| WO | WO 2010/088481 A1 | 8/2010 |
| WO | WO 2012/031204 A2 | 3/2012 |
| WO | WO 2012/068505 A1 | 5/2012 |
| WO | WO 2012/071526 A2 | 5/2012 |
| WO | WO 2013/044378 A1 | 4/2013 |

OTHER PUBLICATIONS

Ethicon, Inc., "Wound Closure Manual: Chapter 3 (The Surgical Needle)," 15 pages, (1994).
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With The Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey NOTES Presentation to EES NOTES Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-74.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.
USGI® EndoSurgical Operating System—g-Prox® Tissue Grasper/Approximation Device; [online] URL: http://www.usgimedical.com/eos/components-gprox.htm—accessed May 30, 2008 (2 pages).
Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. (2007), pp. 255-259.
D.B. Nelson, MD et al., "Endoscopic Hemostatic Devices," Gastrointestinal Endoscopy, vol. 54, No. 6, 2001, pp. 833-840.

(56) References Cited

OTHER PUBLICATIONS

CRE™ Pulmonary Balloon Dilator; [online] URL: http://www.bostonscientific.com/Device.bsci?page=HCP_Overview&navRe1Id=1000.1003&method=D . . . , accessed Jul. 18, 2008 (4 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).
D. Wilhelm et al., "An Innovative, Safe and Sterile Sigmoid Access (ISSA) for NOTES," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation In Vivo," The Journal of Immunology, 164, pp. 4635-4640 (2000).
Weaver et al., "Theory of electroporation: A review," Bioelectrochemistry and Bioenergetics, 41, pp. 135-160 (1996).
Mulier et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).
"Ethicon Endo-Surgery Studies Presented At DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).
Castellvi et al., "Hybrid Transvaginal Notes Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).
OCTO Port Modular Laparoscopy System for Single Incision Access, Jan. 4, 2010; URL http://www.medgadget.com/archives/2010/01/octo_port_modular_laparo . . . ; accessed Jan. 5, 2010 (4 pages).
Hakko Retractors, obtained Aug. 25, 2009 (5 pages).
Zadno et al., "Linear Superelasticity in Cold-Worked NI-TI," Engineering Aspects of Shape Memory Alloys, pp. 414-419 (1990).
How Stuff Works "How Smart Structures Will Work," http://science.howstuffworks.com/engineering/structural/smart-structure1.htm; accessed online Nov. 1, 2011 (3 pages).
Instant Armor: Science Videos—Science News—ScienCentral; http://www.sciencentral.com/articles./view.php3?article_id=218392121; accessed online Nov. 1, 2011 (2 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Jolly et al., Properties and Applications of Commercial Magnetorheological Fluids. SPIE 5th Annual Int. Symposium on Smart Structures and Materials, 1998 (18 pages).
Rutala et al. "Guideline for Disinfection and Sterilization in Healthcare Facilities, 2008" (available at http://www.cdc.gov/hicpac/Disinfection_Sterilization/13_11sterilizingPractices.html).
Bewlay et al., "Spinning" in ASM Handbook, vol. 14B, Metalworking: Sheet Forming (2006).
Schoenbach et al. "Bacterial Decontamination of Liquids with Pulsed Electric Fields" IEEE Transactions on Dielectrics and Electrical Insulation. vol. 7 No. 5. Oct. 2000, pp. 637-645.
Davalos, et al., "Tissue Ablation with Irreversible Electroporation," Annals of Biomedical Engineering, 33.2 (2005): 223-231.
Maxim Integrated Application Note 3977: Class D Amplifiers: Fundamentals of Operation and Recent Developments, Jan. 31, 2007.

\* cited by examiner

SURGICAL INSTRUMENT COMPRISING AN ELECTRODE

CROSS REFERENCE TO RELATED APPLICATIONS

This application is a divisional application claiming priority under 35 U.S.C. § 121 to U.S. patent application Ser. No. 12/641,837, entitled SURGICAL INSTRUMENT COMPRISING AN ELECTRODE, filed Dec. 18, 2009, now U.S. Pat. No. 9,028,483, the entire disclosure of which is hereby incorporated by reference herein.

BACKGROUND i. Field of the Invention

The present invention generally relates to surgical devices and methods.

ii. Description of the Related Art

Traditional, or open, surgical techniques may require a surgeon to make large incisions in a patient's body in order to access a tissue treatment region, or surgical site. In some instances, these large incisions may prolong the recovery time of and/or increase the scarring to the patient. As a result, minimally invasive surgical techniques are becoming more preferred among surgeons and patients owing to the reduced size of the incisions required for various procedures. In some circumstances, minimally invasive surgical techniques may reduce the possibility that the patient will suffer undesirable post-surgical conditions, such as scarring and/or infections, for example. Further, such minimally invasive techniques can allow the patient to recover more rapidly as compared to traditional surgical procedures.

Endoscopy is one minimally invasive surgical technique which allows a surgeon to view and evaluate a surgical site by inserting at least one cannula, or trocar, into the patient's body through a natural opening in the body and/or through a relatively small incision. In use, an endoscope can be inserted into, or through, the trocar so that the surgeon can observe the surgical site. In various embodiments, the endoscope may include a flexible or rigid shaft, a camera and/or other suitable optical device, and a handle portion. In at least one embodiment, the optical device can be located on a first, or distal, end of the shaft and the handle portion can be located on a second, or proximal, end of the shaft. In various embodiments, the endoscope may also be configured to assist a surgeon in taking biopsies, retrieving foreign objects, and introducing surgical instruments into the surgical site.

Laparoscopic surgery is another minimally invasive surgical technique where procedures in the abdominal or pelvic cavities can be performed through small incisions in the patient's body. A key element of laparoscopic surgery is the use of a laparoscope which typically includes a telescopic lens system that can be connected to a video camera. In various embodiments, a laparoscope can further include a fiber optic system connected to a halogen or xenon light source, for example, in order to illuminate the surgical site. In various laparoscopic, and/or endoscopic, surgical procedures, a body cavity of a patient, such as the abdominal cavity, for example, can be insufflated with carbon dioxide gas, for example, in order to create a temporary working space for the surgeon. In such procedures, a cavity wall can be elevated above the organs within the cavity by the carbon dioxide gas. Carbon dioxide gas is usually used for insufflation because it can be easily absorbed and removed by the body.

In at least one minimally invasive surgical procedure, an endoscope and/or laparoscope can be inserted through a natural opening of a patient to allow a surgeon to access a surgical site. Such procedures are generally referred to as Nature Orifice Transluminal Endoscopic Surgery or (NOTES)™ and can be utilized to treat tissue while reducing the number of incisions, and external scars, to a patient's body. In various NOTES procedures, for example, an endoscope can include at least one working channel defined therein which can be used to allow the surgeon to insert a surgical instrument therethrough in order to access the surgical site.

The foregoing discussion is intended only to illustrate various aspects of the related art in the field of the invention at the time, and should not be taken as a disavowal of claim scope.

FIGURES

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

FIG. 1 illustrates one embodiment of an electrical ablation system.

FIGS. 2A-D illustrate one embodiment of the electrical ablation system in various phases of deployment.

Figure 9:
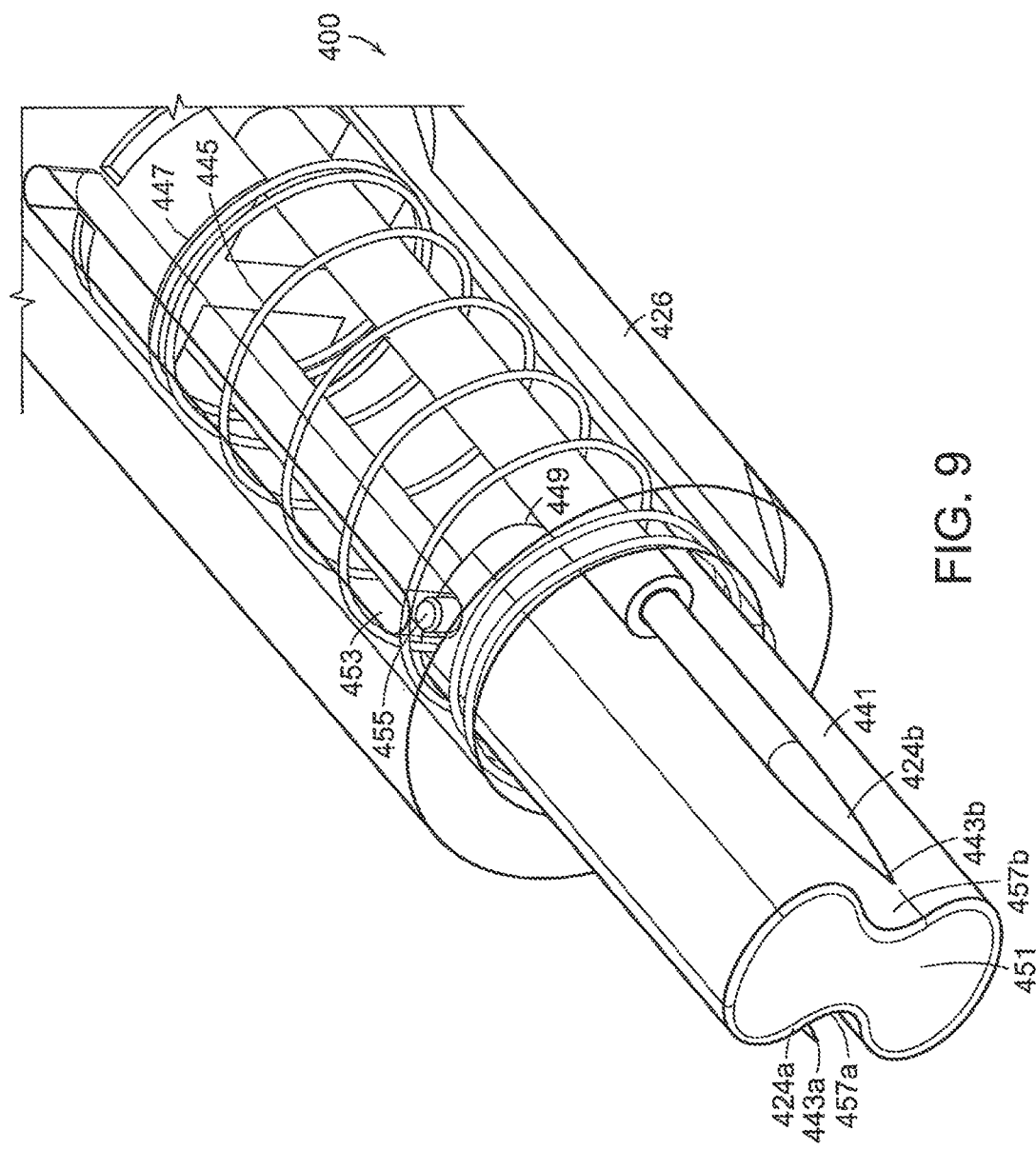

FIG. 9 is a perspective view of a distal end of an alternative embodiment of a surgical instrument illustrating a first electrode, a second electrode, and an insulative guard, wherein the insulative guard is movable between an extended positioned in which it is positioned intermediate the distal ends of the first electrode and the second electrode and a retracted position in which it is displaced proximally relative to the distal ends of the first and second electrodes.

Figure 10:
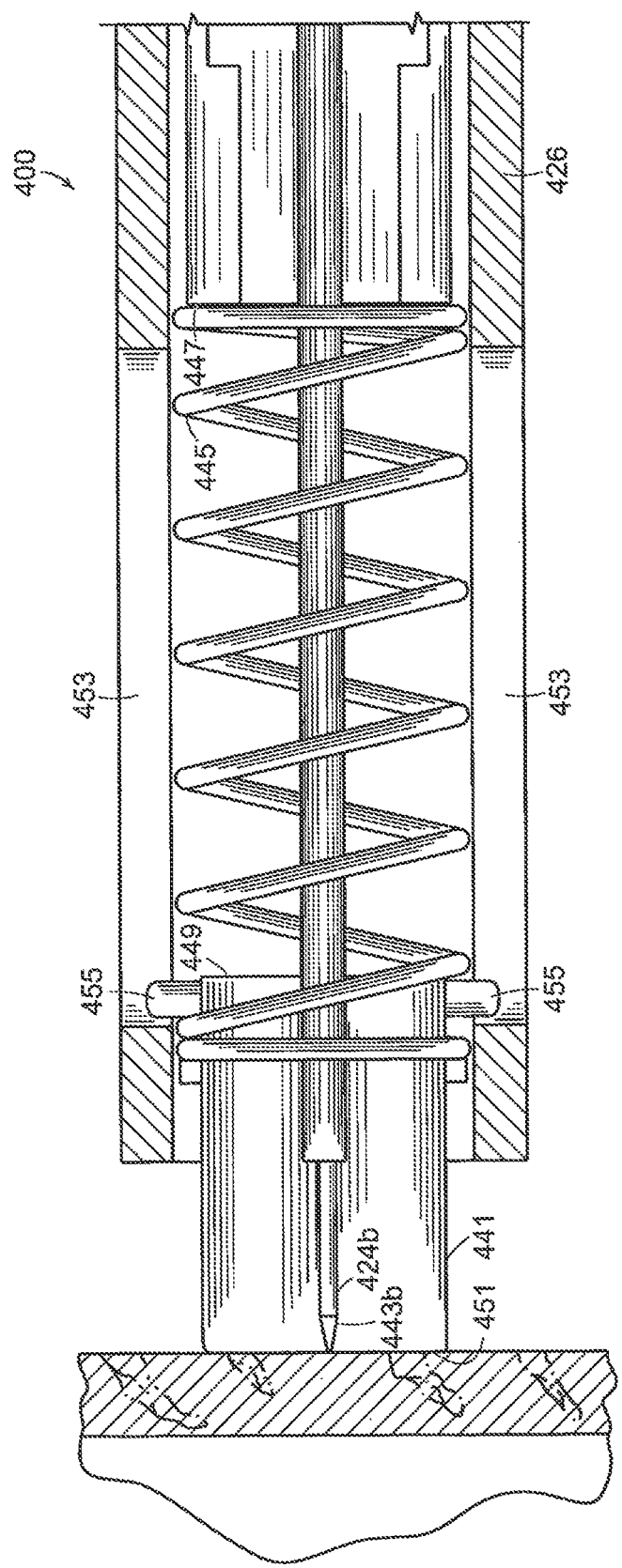

FIG. 10 is a cross-sectional view of the surgical instrument of FIG. 9 illustrating the distal ends of the first and second electrodes positioned against tissue and the insulative guard in its extended position.

Figure 11:
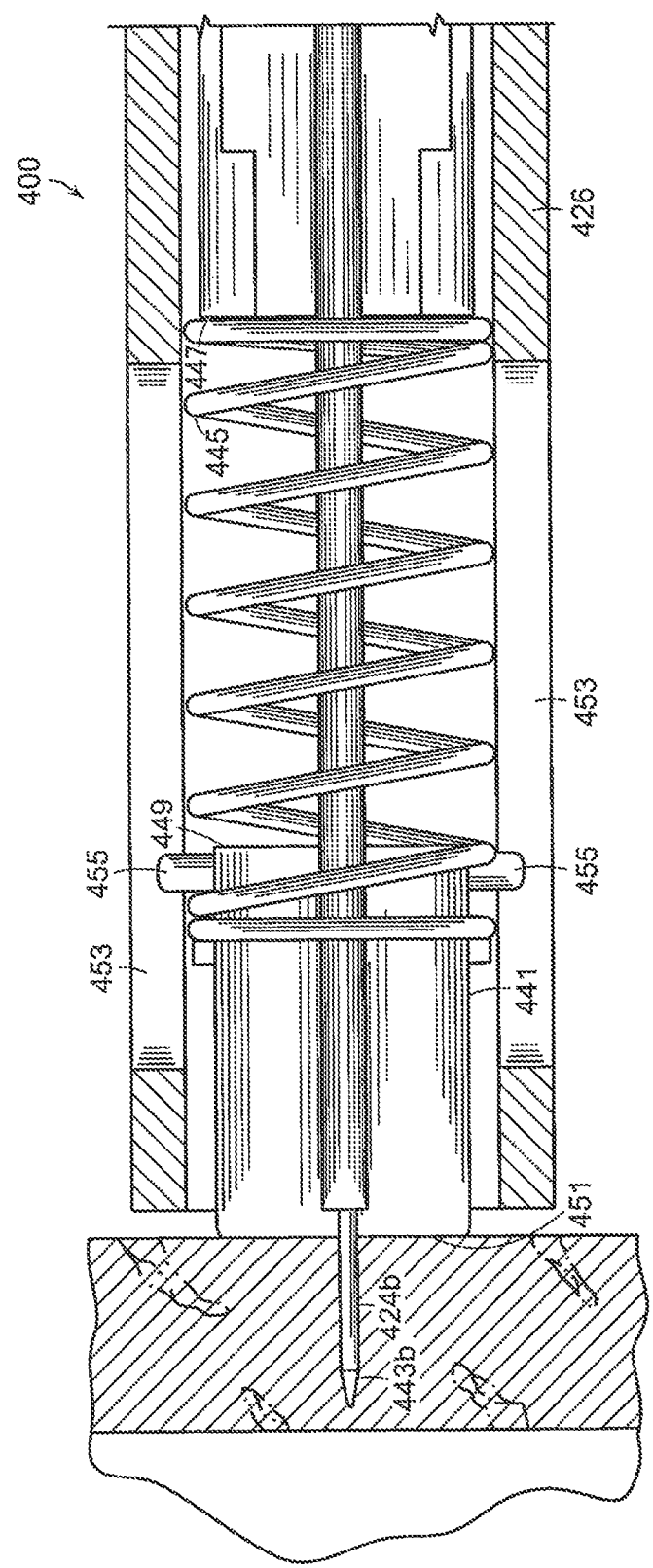

FIG. 11 is a cross-sectional view of the surgical instrument of FIG. 9 illustrating the distal ends of the first and second electrodes inserted into the tissue and the insulative guard in a retracted position.

Figure 12:
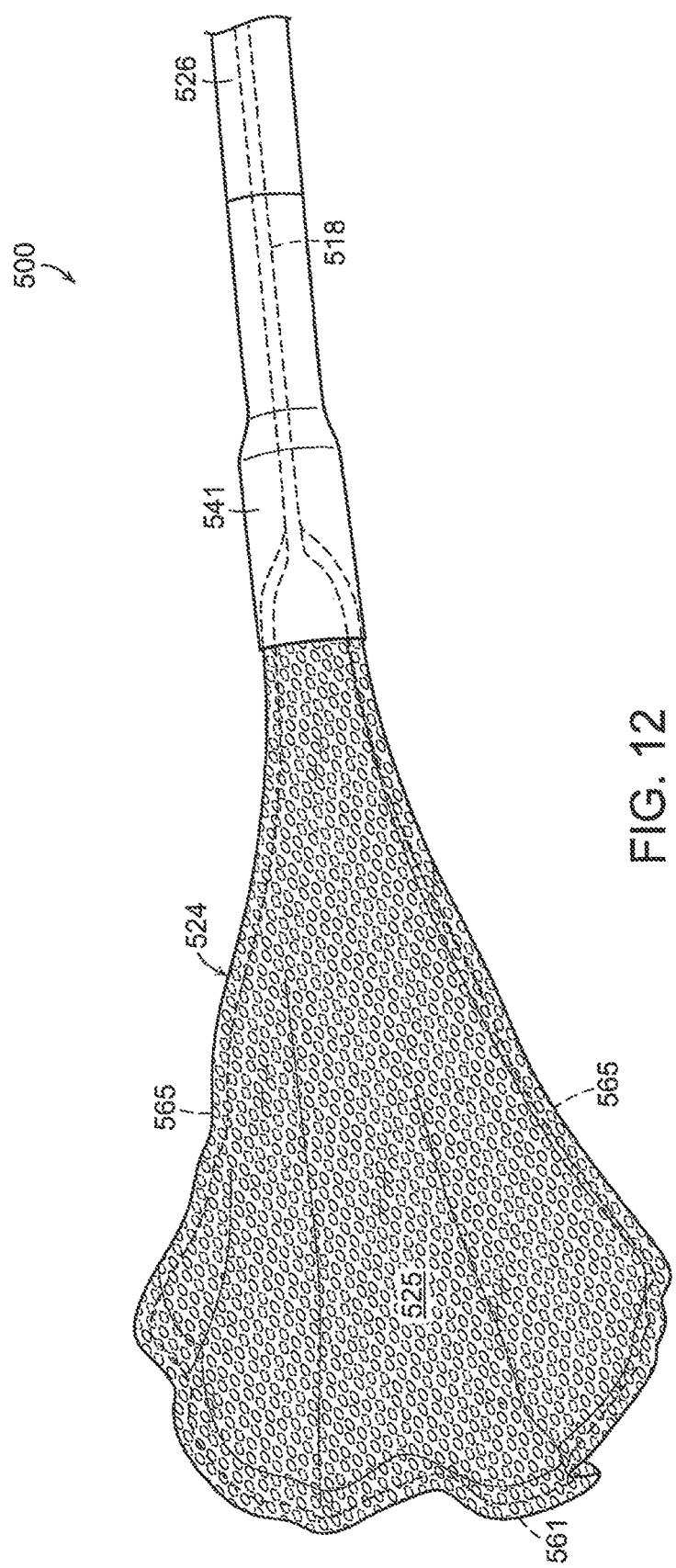

FIG. 12 is a perspective view of a distal end of an alternative embodiment of a surgical instrument comprising a flexible electrode.

Figure 13:
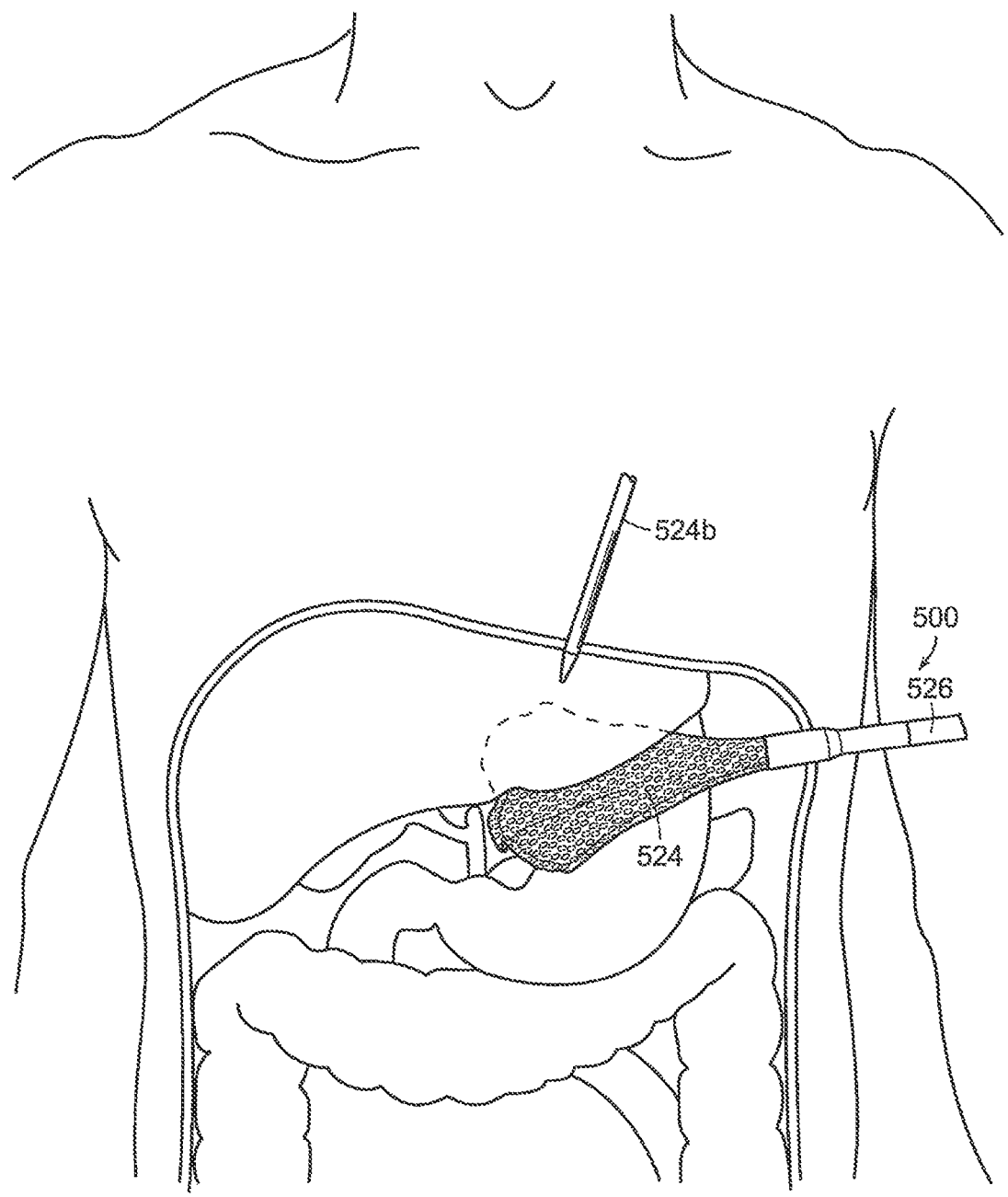

FIG. 13 illustrates the surgical instrument of FIG. 12 positioned against the liver of a patient at one location and an additional surgical instrument comprising an electrode positioned against the liver at another location.

Figure 14:
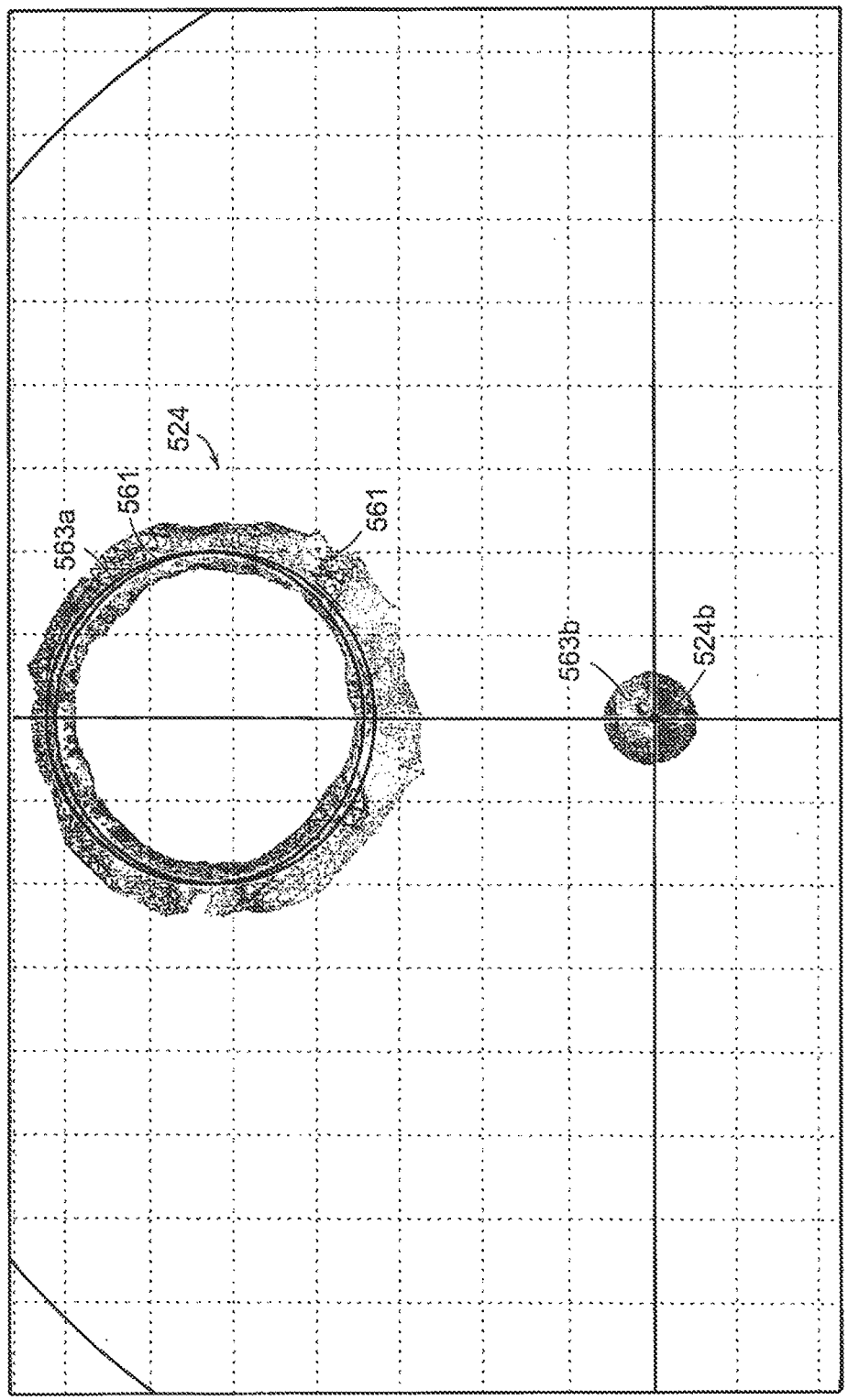

FIG. 14 illustrates the necrotic regions of liver tissue which can be created by the surgical instrument of FIG. 12 and the additional surgical instrument of FIG. 13.

Figure 15:
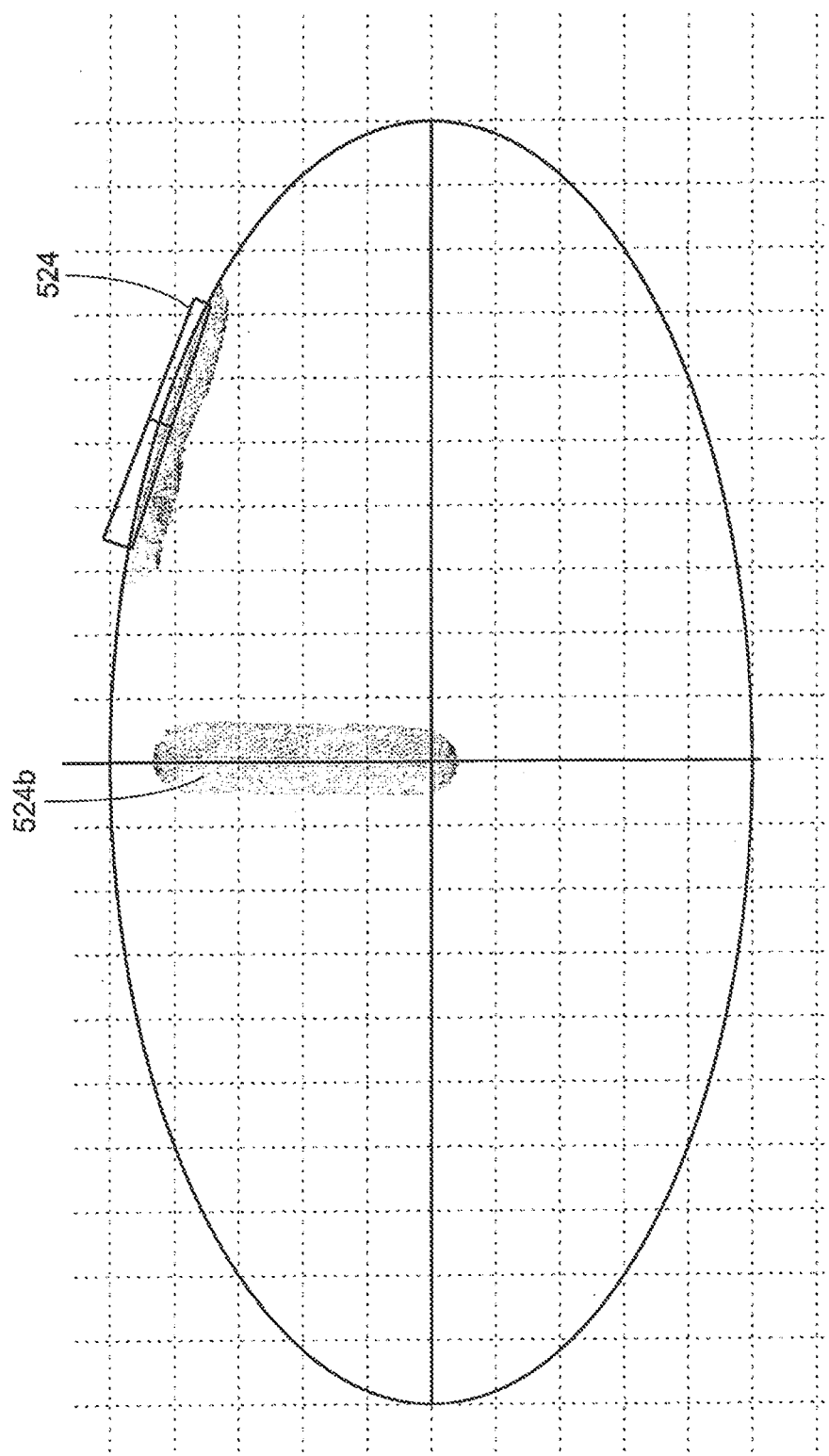

FIG. 15 is another illustration of the necrotic regions of liver tissue which can be created by the surgical instrument of FIG. 12 and the additional surgical instrument of FIG. 13.

Figure 16:
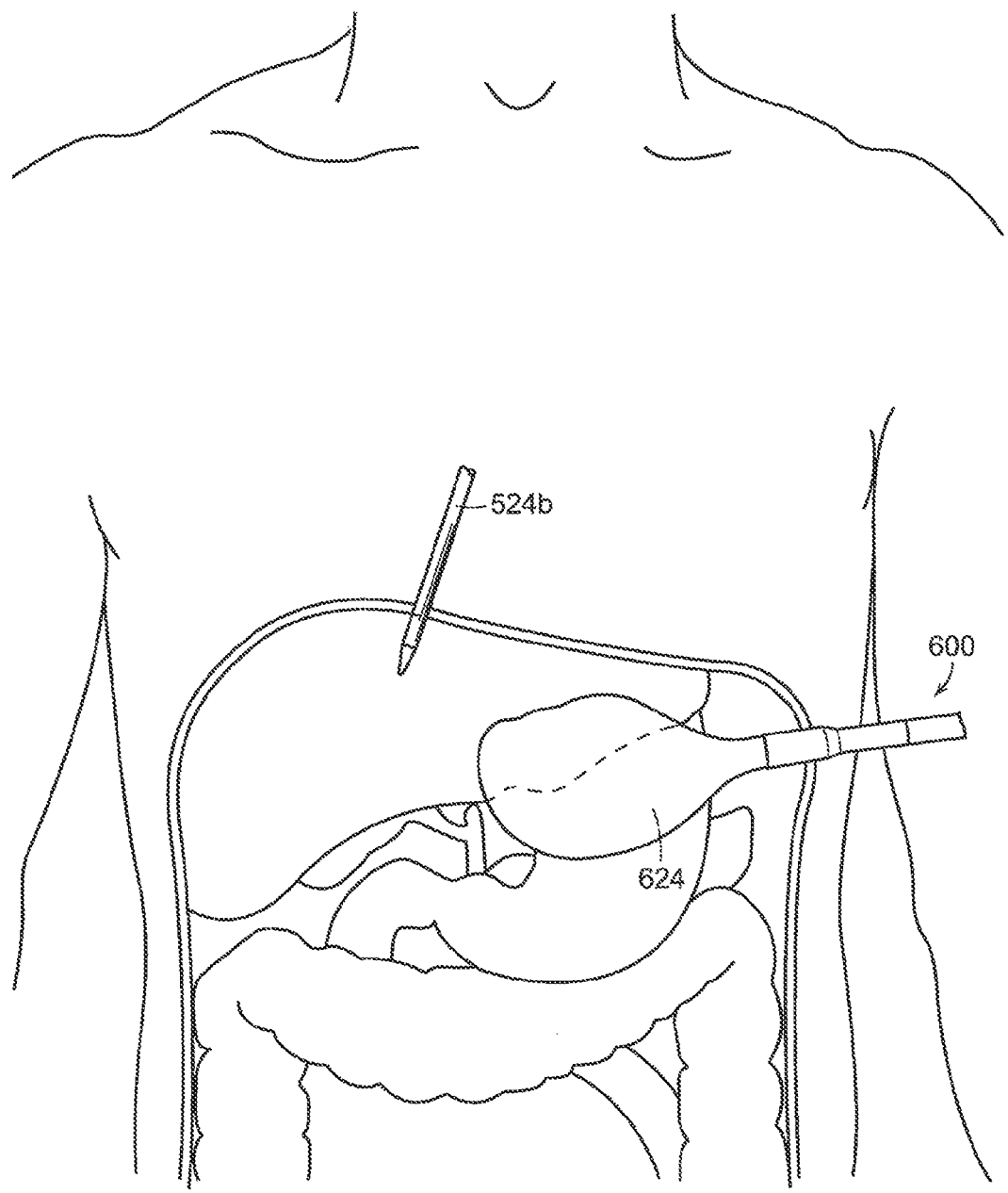

FIG. 16 illustrates an alternative embodiment of a surgical instrument comprising a flexible balloon positioned against the liver of a patient.

Figure 17:
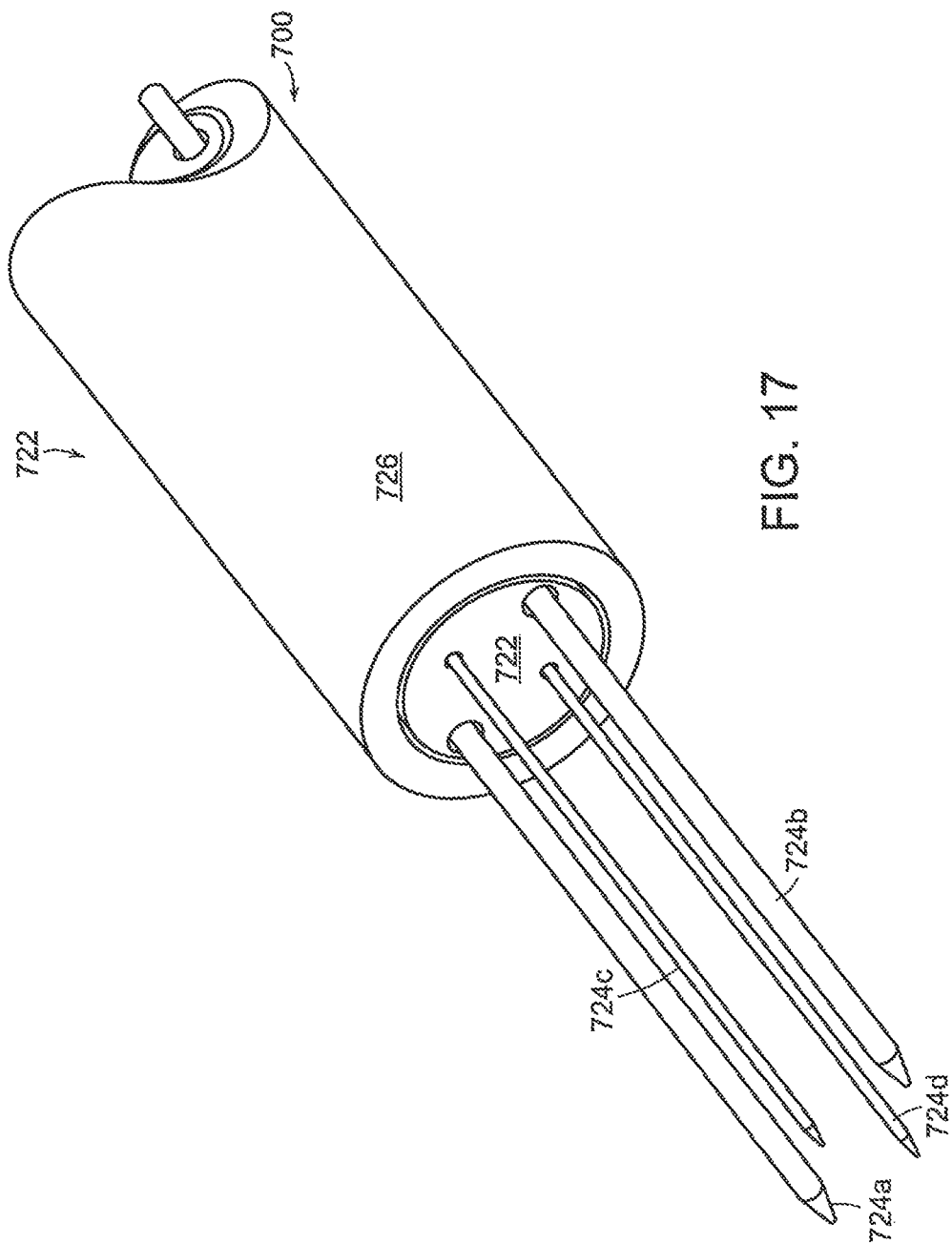

FIG. 17 is a perspective view of a distal end of a surgical instrument.

Figure 18:
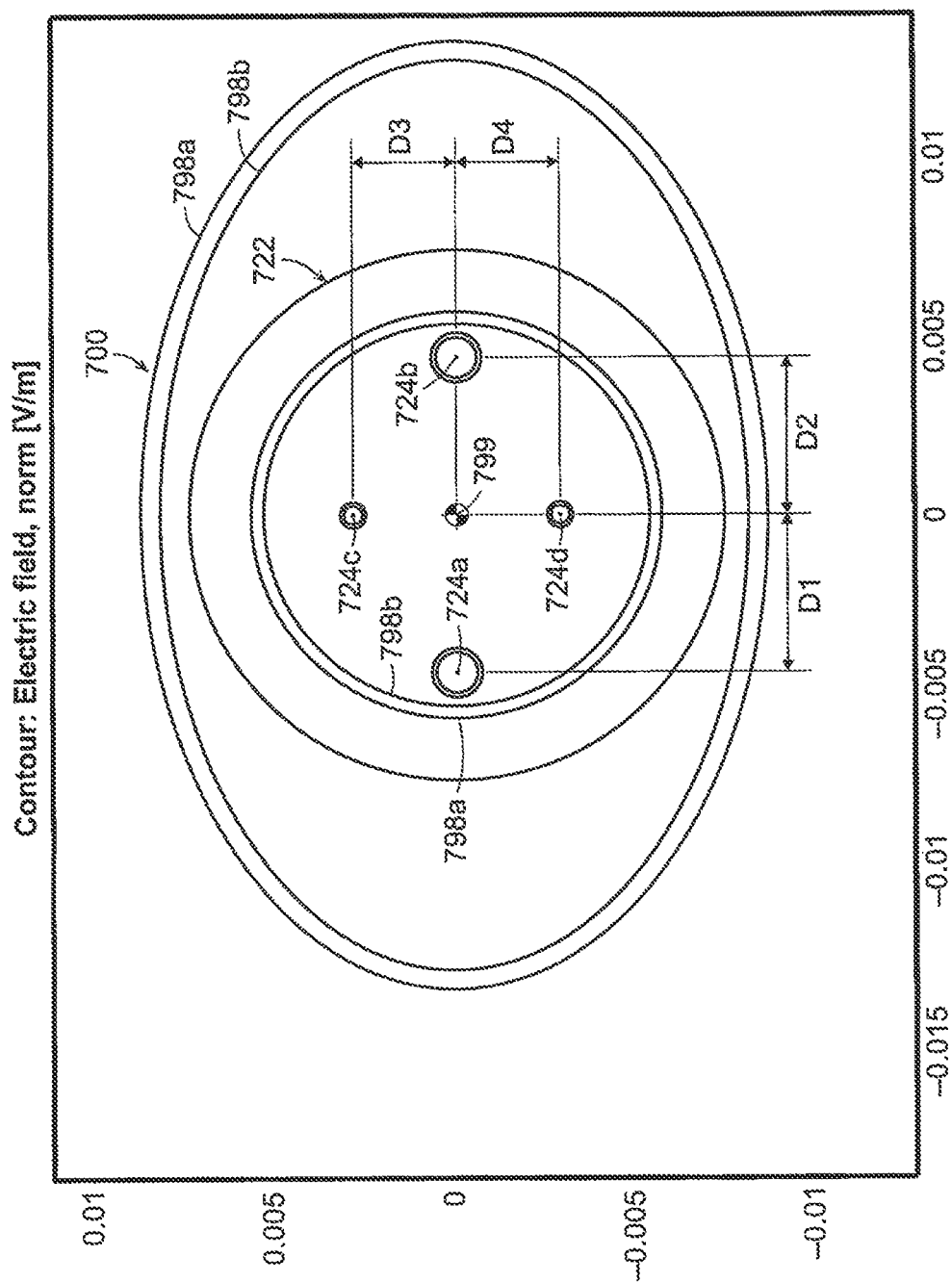

FIG. 18 is an end view of the surgical instrument of FIG. 17.

Figure 19:
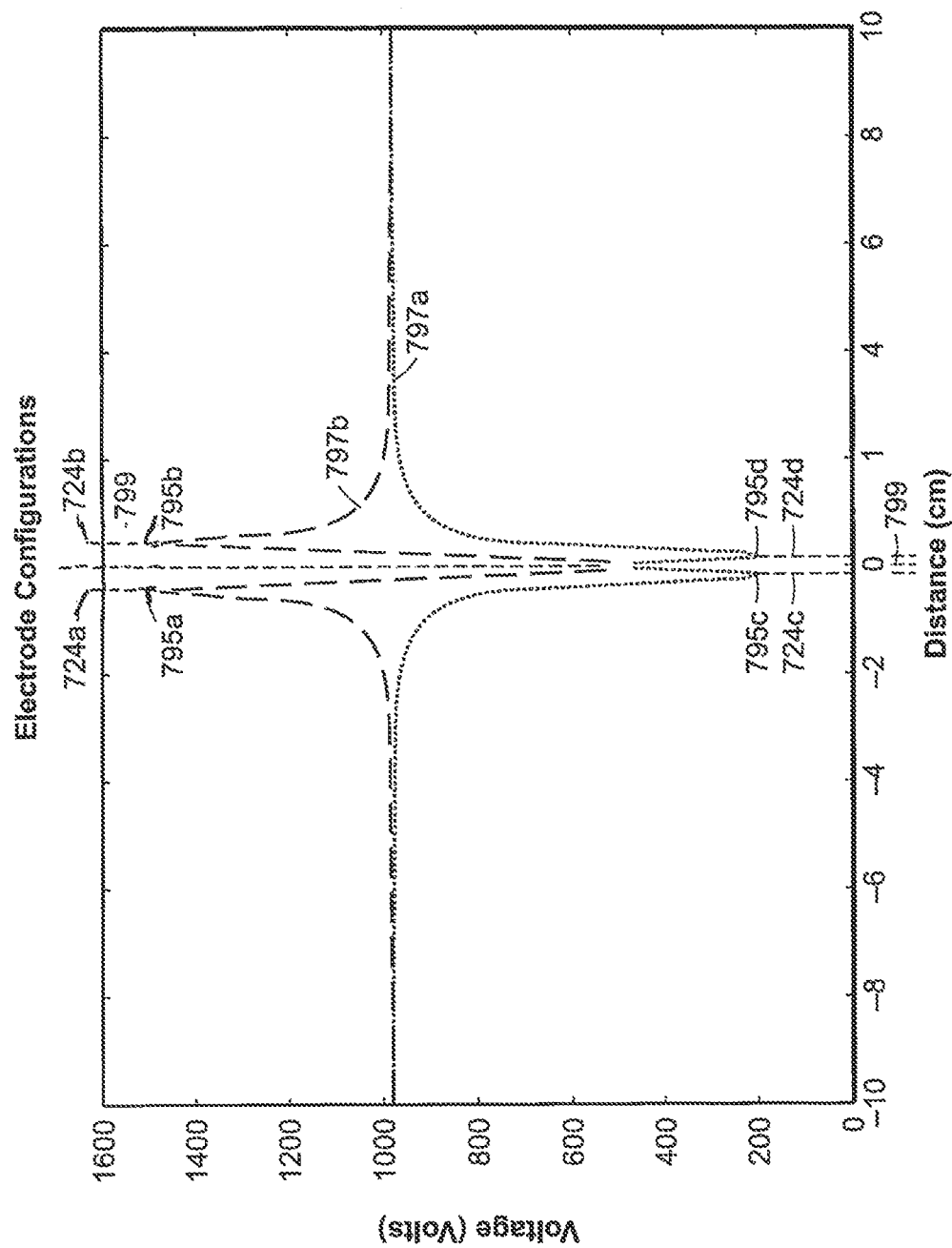

FIG. 19 is a graph of the voltage field that can be generated by the surgical instrument of FIG. 17.

Figure 20:
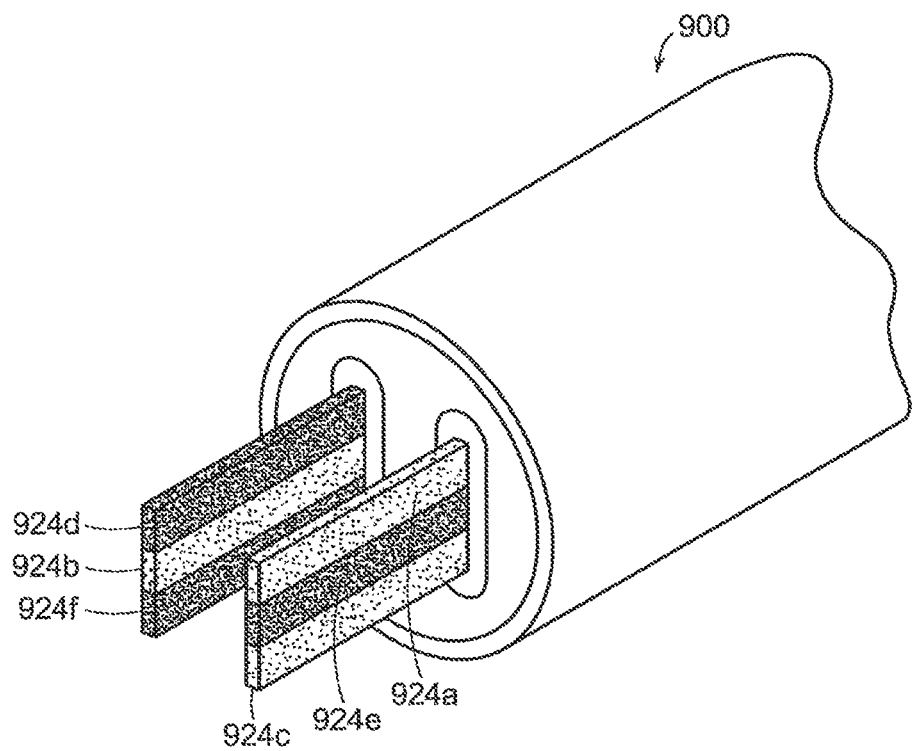

FIG. 20 is an elevational view of a distal end of a surgical instrument.

Figure 21:
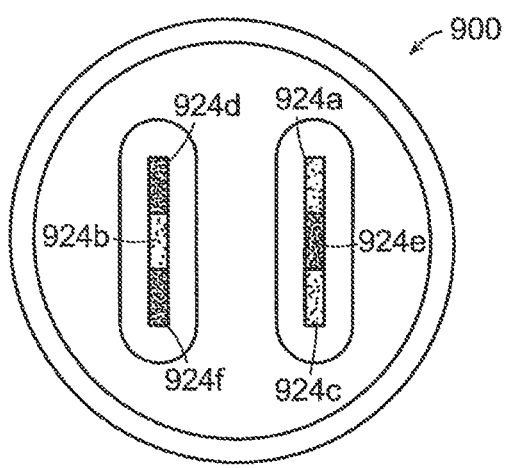

FIG. 21 is an end view of the surgical instrument of FIG. 20.

Corresponding reference characters indicate corresponding parts throughout the several views. The exemplifications set out herein illustrate various embodiments of the invention, in one form, and such exemplifications are not to be construed as limiting the scope of the invention in any manner.

DESCRIPTION

Various embodiments are directed to apparatuses, systems, and methods for the electrical ablation treatment of undesirable tissue such as diseased tissue, cancer, malignant and benign tumors, masses, lesions, and other abnormal tissue growths. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Electrical ablation devices in accordance with the described embodiments may comprise one or more electrodes configured to be positioned into or proximal to undesirable tissue in a tissue treatment region (e.g., target site, worksite) where there is evidence of abnormal tissue growth, for example. In general, the electrodes comprise an electrically conductive portion (e.g., medical grade stainless steel) and are configured to electrically couple to an energy source. Once the electrodes are positioned into or proximal to the undesirable tissue, an energizing potential is applied to the electrodes to create an electric field to which the undesirable tissue is exposed. The energizing potential (and the resulting electric field) may be characterized by multiple parameters such as frequency, amplitude, pulse width (duration of a pulse or pulse length), and/or polarity. Depending on the diagnostic or therapeutic treatment to be rendered, a particular electrode may be configured either as an anode (+) or a cathode (−) or may comprise a plurality of electrodes with at least one configured as an anode and at least one other configured as a cathode. Regardless of the initial polar configuration, the polarity of the electrodes may be reversed by reversing the polarity of the output of the energy source.

In various embodiments, a suitable energy source may comprise an electrical waveform generator, which may be configured to create an electric field that is suitable to create irreversible electroporation in undesirable tissue at various electric filed amplitudes and durations. The energy source may be configured to deliver irreversible electroporation pulses in the form of direct-current (DC) and/or alternating-current (AC) voltage potentials (e.g., time-varying voltage potentials) to the electrodes. The irreversible electroporation pulses may be characterized by various parameters such as frequency, amplitude, pulse length, and/or polarity. The undesirable tissue may be ablated by exposure to the electric potential difference across the electrodes.

In one embodiment, the energy source may comprise a wireless transmitter to deliver energy to the electrodes using wireless energy transfer techniques via one or more remotely positioned antennas. Those skilled in the art will appreciate that wireless energy transfer or wireless power transmission is the process of transmitting electrical energy from an energy source to an electrical load without interconnecting wires. An electrical transformer is the simplest instance of wireless energy transfer. The primary and secondary circuits of a transformer are not directly connected and the transfer of energy takes place by electromagnetic coupling through a process known as mutual induction.

Power also may be transferred wirelessly using RF energy. Wireless power transfer technology using RF energy is produced by Powercast, Inc. and can achieve an output of 6 volts for a little over one meter. Other low-power wireless power technology has been proposed such as described in U.S. Pat. No. 6,967,462, the entire disclosure of which is incorporated by reference herein.

The apparatuses, systems, and methods in accordance with certain described embodiments may be configured for minimally invasive ablation treatment of undesirable tissue through the use of irreversible electroporation to be able to ablate undesirable tissue in a controlled and focused manner without inducing thermally damaging effects to the surrounding healthy tissue. The apparatuses, systems, and methods in accordance with the described embodiments may be configured to ablate undesirable tissue through the use of electroporation or electropermeabilization. More specifically, in various embodiments, the apparatuses, systems, and methods in accordance with the described embodiments may be configured to ablate undesirable tissue through the use of irreversible electroporation. Electroporation increases the permeabilization of a cell membrane by exposing the cell to electric pulses. The external electric field (electric potential/per unit length) to which the cell membrane is exposed to significantly increases the electrical conductivity and permeability of the plasma in the cell membrane. The primary parameter affecting the transmembrane potential is the potential difference across the cell membrane. Irreversible electroporation is the application of an electric field of a specific magnitude and duration to a cell membrane such that the permeabilization of the cell membrane cannot be reversed, leading to cell death without inducing a significant amount of heat in the surrounding tissue. The destabilizing potential forms pores in the cell membrane when the potential across the cell membrane exceeds its critical membrane voltage causing the cell to die under a process known as apoptosis and/or necrosis. The application of irreversible electroporation pulses to cells is an effective way for ablating large volumes of undesirable tissue without deleterious thermal effects to the surrounding healthy tissue associated with thermal-inducing ablation treatments. This is because irreversible electroporation destroys cells without heat and thus does not destroy the cellular support structure or regional vasculature. A destabilizing irreversible electroporation pulse, suitable to cause cell death without inducing a significant amount of thermal damage to the surrounding healthy tissue, may have amplitude in the range of about several hundred to about several thousand volts and is generally applied across biological membranes over a distance of about several millimeters, for example, for a relatively long duration. Thus, the undesirable tissue may be ablated in-vivo through the delivery of destabilizing electric fields by quickly creating cell necrosis.

The apparatuses, systems, and methods for electrical ablation therapy in accordance with the described embodiments may be adapted for use in minimally invasive surgical procedures to access the tissue treatment region in various anatomic locations such as the brain, lungs, breast, liver, gall bladder, pancreas, prostate gland, and various internal body lumen defined by the esophagus, stomach, intestine, colon, arteries, veins, anus, vagina, cervix, fallopian tubes, and the peritoneal cavity, for example, without limitation. Minimally invasive electrical ablation devices may be introduced to the tissue treatment region using a trocar inserted though a small opening formed in the patient's body or through a natural body orifice such as the mouth, anus, or vagina using translumenal access techniques known as Natural Orifice Translumenal Endoscopic Surgery (NOTES)™. Once the electrical ablation devices (e.g., electrodes) are located into or proximal to the undesirable tissue in the treatment region, electric field potentials can be applied to the undesirable tissue by the energy source. The electrical ablation devices can comprise portions that may be inserted into the tissue treatment region percutaneously (e.g., where access to inner organs or other tissue is done via needle-puncture of the skin). Other portions of the electrical ablation devices may be introduced into the tissue treatment region endoscopically (e.g., laparoscopically and/or thoracoscopically) through trocars or working channels of the endoscope, through small incisions, or transcutaneously (e.g., where electric pulses are delivered to the tissue treatment region through the skin).

Figure 1:
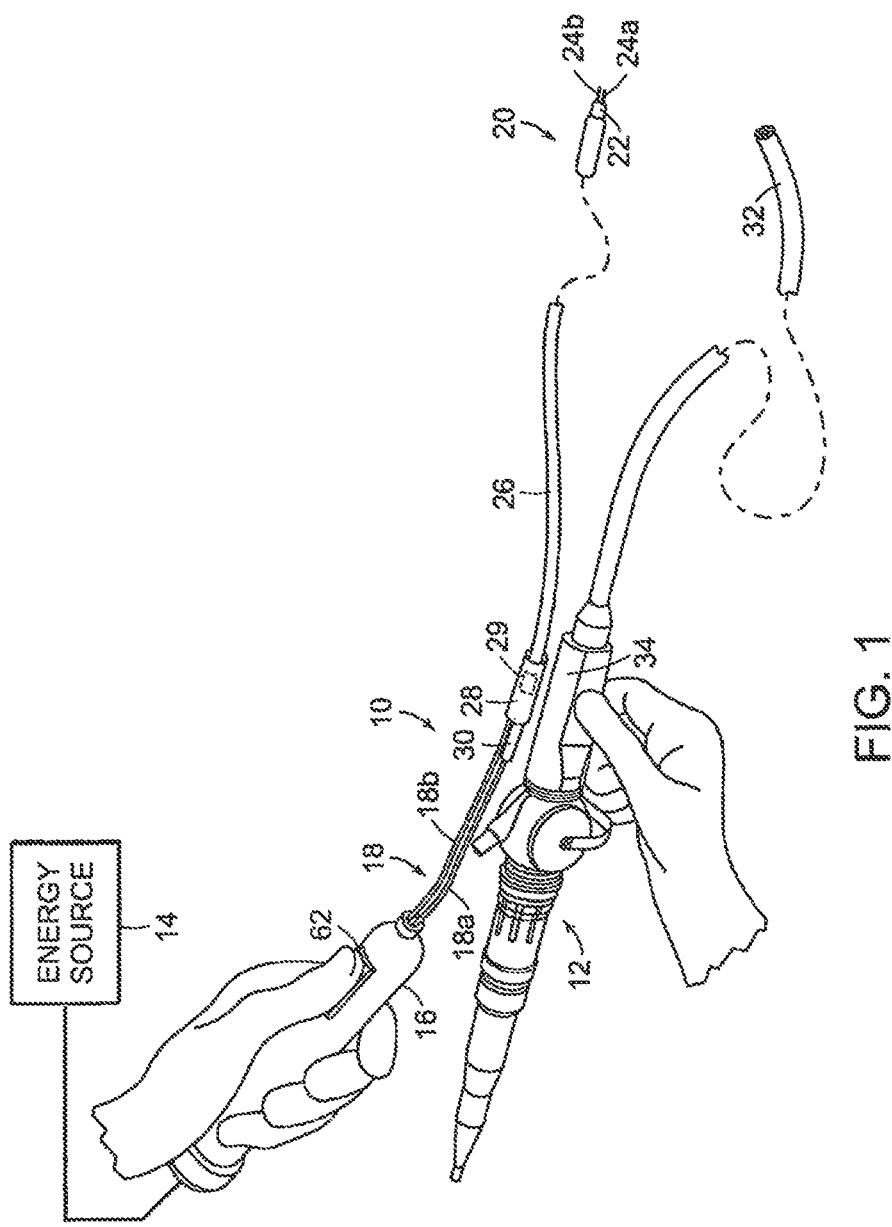

FIG. 1 illustrates one embodiment of an electrical ablation system 10. The electrical ablation system 10 may be employed to ablate undesirable tissue such as diseased tissues, cancers, tumors, masses, lesions, abnormal tissue growths inside a patient using electrical energy. The electrical ablation system 10 may be used in conjunction with endoscopic, laparoscopic, thoracoscopic, open surgical procedures via small incisions or keyholes, percutaneous techniques, transcutaneous techniques, and/or external non-invasive techniques, or any combinations thereof without limitation. The electrical ablation system 10 may be configured to be positioned within a natural body orifice of the patient such as the mouth, anus, or vagina and advanced through internal body lumen or cavities such as the esophagus, colon, cervix, urethra, for example, to reach the tissue treatment region. The electrical ablation system 10 also may be configured to be positioned and passed through a small incision or keyhole formed through the skin or abdominal wall of the patient to reach the tissue treatment region using a trocar. The tissue treatment region may be located in the brain, lungs, breast, liver, gall bladder, pancreas, prostate gland, various internal body lumen defined by the esophagus, stomach, intestine, colon, arteries, veins, anus, vagina, cervix, fallopian tubes, and the peritoneal cavity, for example, without limitation. The electrical ablation system 10 can be configured to treat a number of lesions and ostepathologies comprising metastatic lesions, tumors, fractures, infected sites, and/or inflamed sites. Once positioned into or proximate the tissue treatment region, the electrical ablation system 10 can be actuated (e.g., energized) to ablate the undesirable tissue. In one embodiment, the electrical ablation system 10 may be configured to treat diseased tissue in the gastrointestinal (GI) tract, esophagus, lung, or stomach that may be accessed orally. In another embodiment, the electrical ablation system 10 may be adapted to treat undesirable tissue in the liver or other organs that may be accessible using translumenal access techniques such as, without limitation, NOTES™ techniques, where the electrical ablation devices may be initially introduced through a natural orifice such as the mouth, anus, or vagina and then advanced to the tissue treatment site by puncturing the walls of internal body lumen such as the stomach, intestines, colon, cervix. In various embodiments, the electrical ablation system 10 may be adapted to treat undesirable tissue in the brain, liver, breast, gall bladder, pancreas, or prostate gland, using one or more electrodes positioned percutaneously, transcutaneously, translumenally, minimally invasively, and/or through open surgical techniques, or any combination thereof.

In one embodiment, the electrical ablation system 10 may be employed in conjunction with a flexible endoscope 12, as well as a rigid endoscope, laparoscope, or thoracoscope, such as the GIF-100 model available from Olympus Corporation. In one embodiment, the endoscope 12 may be introduced to the tissue treatment region trans-anally through the colon, trans-orally through the esophagus and stomach, trans-vaginally through the cervix, transcutaneously, or via an external incision or keyhole formed in the abdomen in conjunction with a trocar. The electrical ablation system 10 may be inserted and guided into or proximate the tissue treatment region using the endoscope 12.

In the embodiment illustrated in FIG. 1, the endoscope 12 comprises an endoscope handle 34 and an elongate relatively flexible shaft 32. The distal end of the flexible shaft 32 may comprise a light source and a viewing port. Optionally, the flexible shaft 32 may define one or more working channels for receiving various instruments, such as electrical ablation devices, for example, therethrough. Images within the field of view of the viewing port are received by an optical device, such as a camera comprising a charge coupled device (CCD) usually located within the endoscope 12, and are transmitted to a display monitor (not shown) outside the patient.

In one embodiment, the electrical ablation system 10 may comprise an electrical ablation device 20, a plurality of electrical conductors 18, a handpiece 16 comprising an activation switch 62, and an energy source 14, such as an electrical waveform generator, electrically coupled to the activation switch 62 and the electrical ablation device 20. The electrical ablation device 20 comprises a relatively flexible member or shaft 22 that may be introduced to the tissue treatment region using a variety of known techniques such as an open incision and a trocar, through one or more of the working channels of the endoscope 12, percutaneously, or transcutaneously, for example.

In one embodiment, one or more electrodes (e.g., needle electrodes, balloon electrodes), such as first and second electrodes 24a,b, extend out from the distal end of the electrical ablation device 20. In one embodiment, the first electrode 24a may be configured as the positive electrode and the second electrode 24b may be configured as the negative electrode. The first electrode 24a is electrically connected to a first electrical conductor 18a, or similar electrically conductive lead or wire, which is coupled to the positive terminal of the energy source 14 through the activation switch 62. The second electrode 24b is electrically connected to a second electrical conductor 18b, or similar electrically conductive lead or wire, which is coupled to the negative terminal of the energy source 14 through the activation switch 62. The electrical conductors 18a,b are electrically insulated from each other and surrounding structures, except for the electrical connections to the respective electrodes 24a,b. In various embodiments, the electrical ablation device 20 may be configured to be introduced into or proximate the tissue treatment region using the endoscope 12 (laparoscope or thoracoscope), open surgical procedures, or external and non-invasive medical procedures. The electrodes 24a,b may be referred to herein as endoscopic or laparoscopic electrodes, although variations thereof may be inserted transcutaneously or percutaneously. As previously discussed, either one or both electrodes 24a,b may be adapted and configured to slideably move in and out of a cannula, lumen, or channel defined within the flexible shaft 22.

Once the electrodes 24a,b are positioned at the desired location into or proximate the tissue treatment region, the electrodes 24a,b may be connected to or disconnected from the energy source 14 by actuating or de-actuating the switch 62 on the handpiece 16. The switch 62 may be operated manually or may be mounted on a foot switch (not shown), for example. The electrodes 24a,b deliver electric field pulses to the undesirable tissue. The electric field pulses may be characterized based on various parameters such as pulse shape, amplitude, frequency, and duration. The electric field pulses may be sufficient to induce irreversible electroporation in the undesirable tissue. The induced potential depends on a variety of conditions such as tissue type, cell size, and electrical pulse parameters. The primary electrical pulse parameter affecting the transmembrane potential for a specific tissue type is the amplitude of the electric field and pulse length that the tissue is exposed to.

In one embodiment, a protective sleeve or sheath 26 may be slideably disposed over the flexible shaft 22 and within a handle 28. In another embodiment, the sheath 26 may be slideably disposed within the flexible shaft 22 and the handle 28, without limitation. The sheath 26 is slideable and may be located over the electrodes 24a,b to protect the trocar and prevent accidental piercing when the electrical ablation device 20 is advanced therethrough. Either one or both of the electrodes 24a,b of the electrical ablation device 20 may be adapted and configured to slideably move in and out of a cannula, lumen, or channel formed within the flexible shaft 22. The second electrode 24b may be fixed in place. The second electrode 24b may provide a pivot about which the first electrode 24a can be moved in an arc to other points in the tissue treatment region to treat larger portions of the diseased tissue that cannot be treated by fixing the electrodes 24a,b in one location. In one embodiment, either one or both of the electrodes 24a,b may be adapted and configured to slideably move in and out of a working channel formed within a flexible shaft 32 of the flexible endoscope 12 or may be located independently of the flexible endoscope 12. Various features of the first and second electrodes 24a,b are described in more detail in FIGS. 2A-D.

In one embodiment, the first and second electrical conductors 18a,b may be provided through the handle 28. In the illustrated embodiment, the first electrode 24a can be slideably moved in and out of the distal end of the flexible shaft 22 using a slide member 30 to retract and/or advance the first electrode 24a. In various embodiments either or both electrodes 24a,b may be coupled to the slide member 30, or additional slide members, to advance and retract the electrodes 24a,b, e.g., position the electrodes 24a,b. In the illustrated embodiment, the first electrical conductor 18a coupled to the first electrode 24a is coupled to the slide member 30. In this manner, the first electrode 24a, which is slideably movable within the cannula, lumen, or channel defined by the flexible shaft 22, can advanced and retracted with the slide member 30.

In various other embodiments, transducers or sensors may be located in the handle 28 of the electrical ablation device 20 to sense the force with which the electrodes 24a,b penetrate the tissue in the tissue treatment zone. This feedback information may be useful to determine whether either one or both of the electrodes 24a,b have been properly inserted in the tissue treatment region. As is particularly well known, cancerous tumor tissue tends to be denser than healthy tissue and thus greater force is required to insert the electrodes 24a,b therein. The transducers or sensors 29 can provide feedback to the operator, surgeon, or clinician to physically sense when the electrodes 24a,b are placed within the cancerous tumor. The feedback information provided by the transducers or sensors 29 may be processed and displayed by circuits located either internally or externally to the energy source 14. The sensor 29 readings may be employed to determine whether the electrodes 24a,b have been properly located within the cancerous tumor thereby assuring that a suitable margin of error has been achieved in locating the electrodes 24a,b.

In one embodiment, the input to the energy source 14 may be connected to a commercial power supply by way of a plug (not shown). The output of the energy source 14 is coupled to the electrodes 24a,b, which may be energized using the activation switch 62 on the handpiece 16, or in one embodiment, an activation switch mounted on a foot activated pedal (not shown). The energy source 14 may be configured to produce electrical energy suitable for electrical ablation, as described in more detail below.

In one embodiment, the electrodes 24a,b are adapted and configured to electrically couple to the energy source 14 (e.g., generator, waveform generator). Once electrical energy is coupled to the electrodes 24a,b, an electric field is formed in the tissue from the voltage applied at the electrodes 24a,b. The energy source 14 may be configured to generate electric pulses at a predetermined frequency, amplitude, pulse length, and/or polarity that are suitable to induce irreversible electroporation to ablate substantial volumes of undesirable tissue in the treatment region. For example, the energy source 14 may be configured to deliver DC electric pulses having a predetermined frequency, amplitude, pulse length, and/or polarity suitable to induce irreversible electroporation to ablate substantial volumes of undesirable tissue in the treatment region. The DC pulses may be positive or negative relative to a particular reference polarity. The polarity of the DC pulses may be reversed or inverted from positive-to-negative or negative-to-positive a predetermined number of times to induce irreversible electroporation to ablate substantial volumes of undesirable tissue in the treatment region.

In one embodiment, a timing circuit may be coupled to the output of the energy source 14 to generate electric pulses. The timing circuit may comprise one or more suitable switching elements to produce the electric pulses. For example, the energy source 14 may produce a series of n electric pulses (where n is any positive integer) of sufficient amplitude and duration to induce irreversible electroporation suitable for tissue ablation when the n electric pulses are applied to the electrodes 24a,b. In one embodiment, the electric pulses may have a fixed or variable pulse length, amplitude, and/or frequency.

The electrical ablation device 20 may be operated either in bipolar or monopolar mode. In bipolar mode, the first electrode 24a is electrically connected to a first polarity and the second electrode 24b is electrically connected to the opposite polarity. For example, in monopolar mode, the first electrode 24a is coupled to a prescribed voltage and the second electrode 24b is set to ground. In the illustrated embodiment, the energy source 14 may be configured to operate in either the bipolar or monopolar modes with the electrical ablation system 10. In bipolar mode, the first electrode 24a is electrically connected to a prescribed voltage of one polarity and the second electrode 24b is electrically connected to a prescribed voltage of the opposite polarity. When more than two electrodes are used, the polarity of the electrodes may be alternated so that any two adjacent electrodes may have either the same or opposite polarities, for example.

In monopolar mode, it is not necessary that the patient be grounded with a grounding pad. Since a monopolar energy source 14 is typically constructed to operate upon sensing a ground pad connection to the patient, the negative electrode of the energy source 14 may be coupled to an impedance simulation circuit. In this manner, the impedance circuit simulates a connection to the ground pad and thus is able to activate the energy source 14. It will be appreciated that in monopolar mode, the impedance circuit can be electrically connected in series with either one of the electrodes 24a,b that would otherwise be attached to a grounding pad.

In one embodiment, the energy source 14 may be configured to produce RF waveforms at predetermined frequencies, amplitudes, pulse widths or durations, and/or polarities suitable for electrical ablation of cells in the tissue treatment region. One example of a suitable RF energy source is a commercially available conventional, bipolar/monopolar electrosurgical RF generator such as Model Number ICC 350, available from Erbe, GmbH.

In one embodiment, the energy source 14 may be configured to produce destabilizing electrical potentials (e.g., fields) suitable to induce irreversible electroporation. The destabilizing electrical potentials may be in the form of bipolar/monopolar DC electric pulses suitable for inducing irreversible electroporation to ablate tissue undesirable tissue with the electrical ablation device 20. A commercially available energy source suitable for generating irreversible electroporation electric field pulses in bipolar or monopolar mode is a pulsed DC generator such as Model Number ECM 830, available from BTX Molecular Delivery Systems Boston, Mass. In bipolar mode, the first electrode 24a may be electrically coupled to a first polarity and the second electrode 24b may be electrically coupled to a second (e.g., opposite) polarity of the energy source 14. Bipolar/monopolar DC electric pulses may be produced at a variety of frequencies, amplitudes, pulse lengths, and/or polarities. Unlike RF ablation systems, however, which require high power and energy levels delivered into the tissue to heat and thermally destroy the tissue, irreversible electroporation requires very little energy input into the tissue to kill the undesirable tissue without the detrimental thermal effects because with irreversible electroporation the cells are destroyed by electric field potentials rather than heat.

In one embodiment, the energy source 14 may be coupled to the first and second electrodes 24a,b by either a wired or a wireless connection. In a wired connection, the energy source 14 is coupled to the electrodes 24a,b by way of the electrical conductors 18a,b, as shown. In a wireless connection, the electrical conductors 18a,b may be replaced with a first antenna (not shown) coupled the energy source 14 and a second antenna (not shown) coupled to the electrodes 24a,b, wherein the second antenna is remotely located from the first antenna.

In one embodiment, the energy source may comprise a wireless transmitter to deliver energy to the electrodes using wireless energy transfer techniques via one or more remotely positioned antennas. As previously discussed, wireless energy transfer or wireless power transmission is the process of transmitting electrical energy from the energy source 14 to an electrical load, e.g., the abnormal cells in the tissue treatment region, without using the interconnecting electrical conductors 18a,b. An electrical transformer is the simplest instance of wireless energy transfer. The primary and secondary circuits of a transformer are not directly connected. The transfer of energy takes place by electromagnetic coupling through a process known as mutual induction. Wireless power transfer technology using RF energy is produced by Powercast, Inc. The Powercast system can achieve a maximum output of 6 volts for a little over one meter. Other low-power wireless power technology has been proposed such as described in U.S. Pat. No. 6,967,462.

In one embodiment, the energy source 14 may be configured to produce DC electric pulses at frequencies in the range of about 1 Hz to about 10000 Hz, amplitudes in the range of about ±100 to about ±3000 VDC, and pulse lengths (e.g., pulse width, pulse duration) in the range of about 1 μs to about 100 ms. The polarity of the electric potentials coupled to the electrodes 24a,b may be reversed during the electrical ablation therapy. For example, initially, the DC electric pulses may have a positive polarity and an amplitude in the range of about +100 to about +3000 VDC. Subsequently, the polarity of the DC electric pulses may be reversed such that the amplitude is in the range of about −100 to about −3000 VDC. In one embodiment, the undesirable cells in the tissue treatment region may be electrically ablated with DC pulses suitable to induce irreversible electroporation at frequencies of about 10 Hz to about 100 Hz, amplitudes in the range of about +700 to about +1500 VDC, and pulse lengths of about 10 μs to about 50 μs. In another embodiment, the abnormal cells in the tissue treatment region may be electrically ablated with an electrical waveform having an amplitude of about +500 VDC and pulse duration of about 20 ms delivered at a pulse period T or repetition rate, frequency f=1/T, of about 10 Hz. It has been determined that an electric field strength of 1,000V/cm is suitable for destroying living tissue by inducing irreversible electroporation.

Figure 2A:
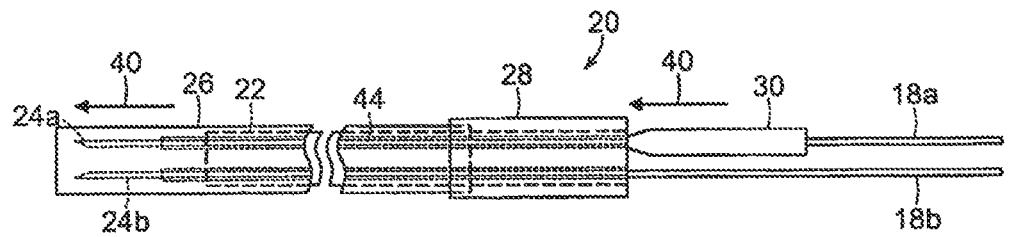
FIG. 2E illustrates one embodiment of the electrical ablation device comprising multiple needle electrodes.
Figure 2B:
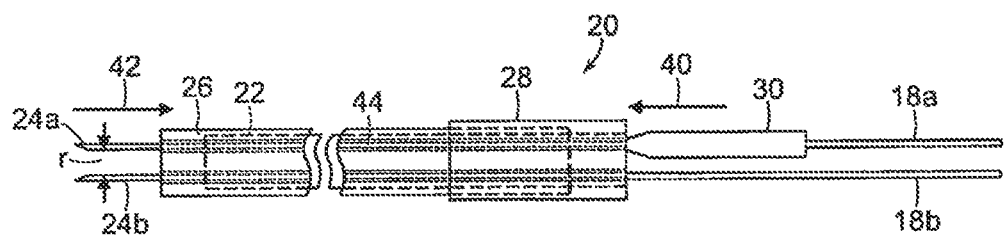
Figure 2C:
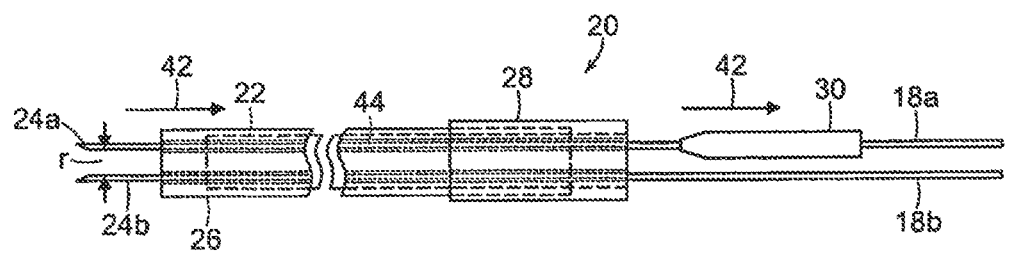
Figure 2D:
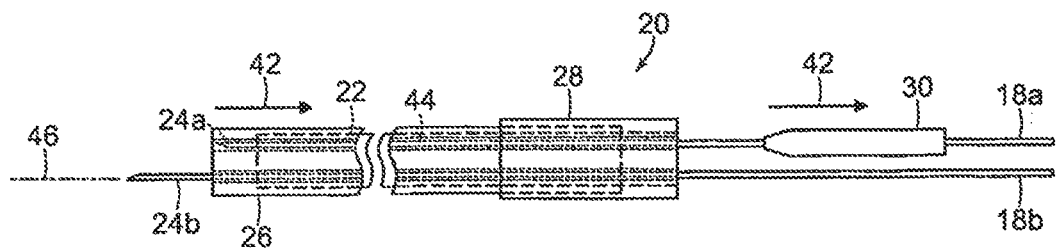
Figure 3:
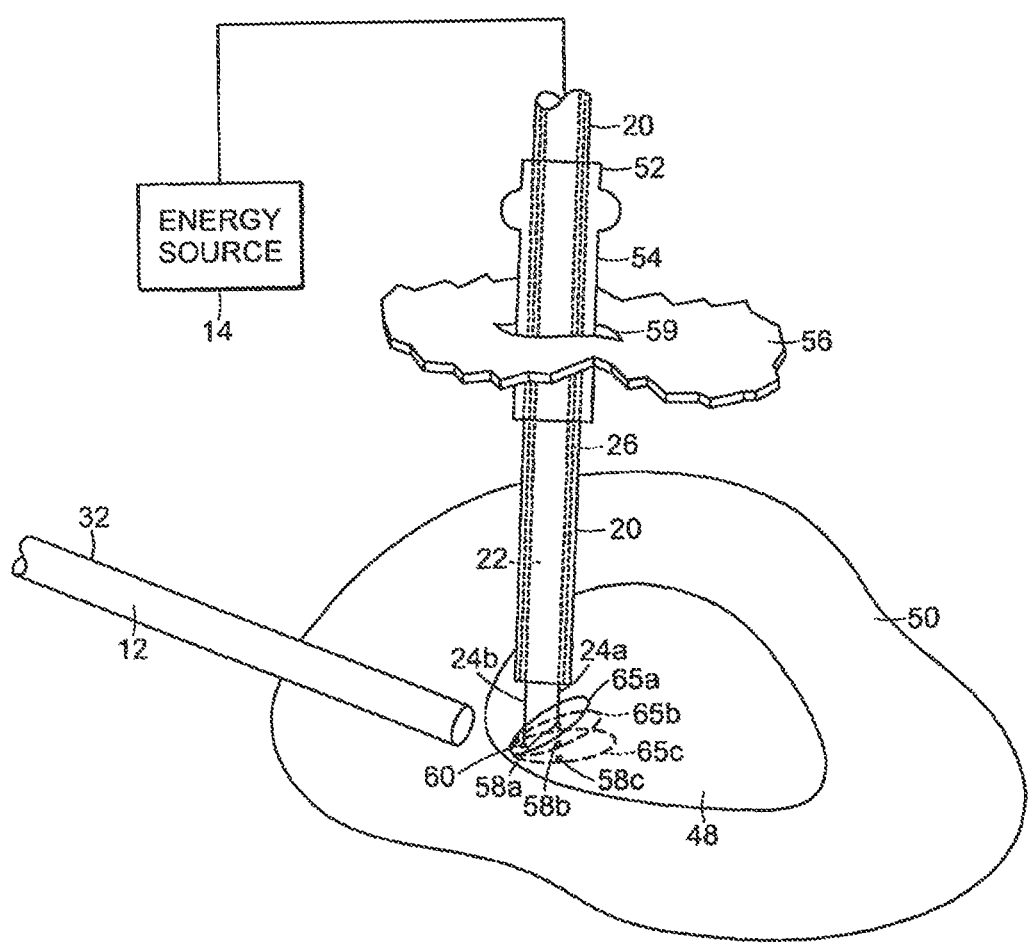
FIG. 3 illustrates one embodiment of the electrical ablation system shown in FIGS. 1 and 2A-D in use to treat undesirable tissue located on the surface of the liver.

FIGS. 2A-D illustrate one embodiment of the electrical ablation device 20 in various phases of deployment. In the embodiment illustrated in FIGS. 2A-D, the sheath 26 is disposed over the flexible shaft 22, however, those skilled in the art will appreciate that the sheath 26 may be disposed within the flexible shaft 22. The electrical ablation device 20 may be used in conjunction with the electrical ablation system 10 shown in FIG. 1. It will be appreciated that other devices and electrode configurations may be employed without limitation. FIG. 2A illustrates an initial phase of deployment wherein the sheath 26 is extended in the direction indicated by arrow 40 to cover the electrodes 24a,b. The electrodes 24a,b may have dimensions of about 0.5 mm, about 1 mm, or about 1.5 mm in diameter. It will be appreciated that the dimensions of the electrodes 24a,b may be anywhere from about 0.5 mm to about 1.5 mm in diameter. The electrical ablation device 20 may be introduced into the tissue treatment region through a trocar, as illustrated in FIG. 3, for example. FIG. 2B illustrates another phase of deployment wherein the sheath 26 is retracted within the handle 28 in the direction indicated by arrow 42. In this phase of deployment, the first and second electrodes 24a,b extend through the distal end of the flexible shaft 22 and are ready to be inserted into or proximate the tissue treatment region. The first electrode 24a may be retracted in direction 42 through a lumen 44 formed in the flexible shaft 22 by holding the handle 28 and pulling on the slide member 30. FIG. 2C illustrates a transition phase wherein the first electrode 24a is the process of being retracted in direction 42 by pulling on the slide member 30 handle, for example, in the same direction. FIG. 2D illustrates another phase of deployment wherein the first electrode 24a is in a fully retracted position. In this phase of deployment the electrical ablation device 20 can be pivotally rotated about an axis 46 defined by the second electrode 24b. The electrodes 24a,b are spaced apart by a distance "r." The distance "r" between the electrodes 24a,b may be 5.0 mm, about 7.5 mm, or about 10 mm. It will be appreciated that the distance "r" between the electrodes 24a,b may be anywhere from about 5.0 mm to about 10.0 mm. Thus, the electrical ablation device 20 may be rotated in an arc about the pivot formed by the second electrode 24b, the first electrode 24a may be placed in a new location in the tissue treatment region within the radius "r." Retracting the first electrode 24a and pivoting about the second electrode 24b enables the surgeon or clinician to target and treat a larger tissue treatment region essentially comprising a circular region having a radius "r," which is the distance between the electrodes 24a,b. Thus, the electrodes 24a,b may be located in a plurality of positions in and around the tissue treatment region in order to treat much larger regions of tissue. Increasing the electrode 24a,b diameter and spacing the electrodes 24a,b further apart enables the generation of an electric field over a much larger tissue regions and thus the ablation of larger volumes of undesirable tissue. In this manner, the operator can treat a larger tissue treatment region comprising cancerous lesions, polyps, or tumors, for example.

Although the electrical ablation electrodes according to the described embodiments have been described in terms of the particular needle type electrodes 24a,b as shown and described in FIGS. 1 and 2A-D, those skilled in the art will appreciate that other configurations of electrical ablation electrodes may be employed for the ablation of undesirable tissue, without limitation. In one embodiment, the electrical ablation device 20 may comprise two or more fixed electrodes that are non-retractable. In another embodiment, the electrical ablation device 20 may comprise two or more retractable electrodes, one embodiment of which is described below with reference to FIG. 2E. In another embodiment, the electrical ablation device 20 may comprise at least one slideable electrode disposed within at least one working channel of the flexible shaft 32 of the endoscope 12. In another embodiment, the electrical ablation device 20 may comprise at least one electrode may be configured to be inserted into the tissue treatment region transcutaneously or percutaneously. Still in various other embodiments, the electrical ablation device 20 may comprise at least one electrode configured to be introduced to the tissue treatment region transcutaneously or percutaneously and at least one other electrode may be configured to be introduced to the tissue treatment region through at least one working channel of the flexible shaft 32 of the endoscope 12. The embodiments, however, are not limited in this context.

Figure 2E:
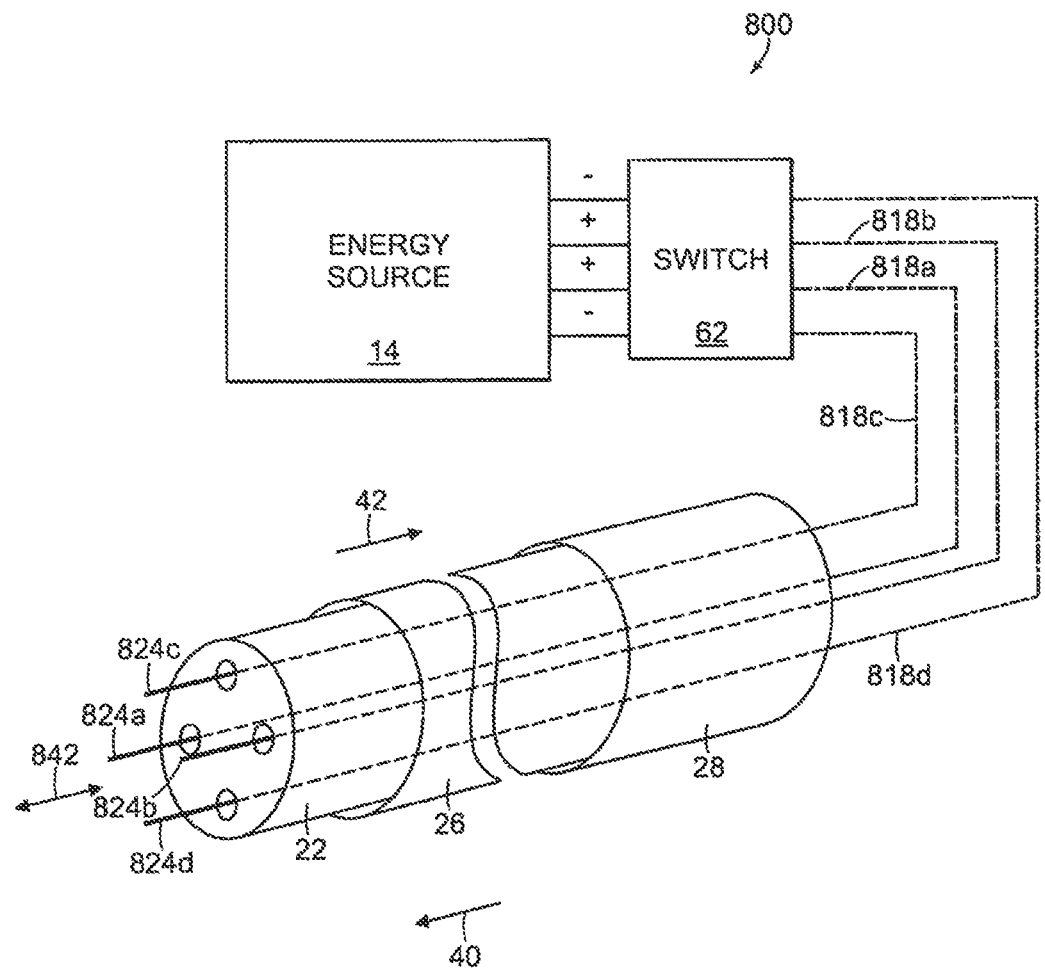

FIG. 2E illustrates one embodiment of an electrical ablation device 100 comprising multiple needle electrodes 124m, where m is any positive integer. In the illustrated embodiment, the electrical ablation device 100 comprises four electrodes 124a, 124b, 124c, 124d. It will be appreciated that in one embodiment, the electrical ablation device 800 also may comprise three needle electrodes 124a, 124b, 124c, without limitation. The electrical ablation device 100 may be used in conjunction with the electrical ablation system 10 shown in FIG. 1. It will be appreciated that other devices and electrode configurations may be employed without limitation. The electrodes 124a-m each may have dimensions of about 0.5 mm, about 1 mm, or about 1.5 mm in diameter. It will be appreciated that the dimensions of each of the electrodes 124a-m may be anywhere from about 0.5 mm to about 1.5 mm in diameter. The electrical ablation device 100 may be introduced into the tissue treatment region through a trocar, as subsequently described and illustrated with reference to FIG. 3, for example.

The electrical ablation device 100 comprises essentially the same components as the electrical ablation device 20 described with reference to FIGS. 2A-D. The electrical ablation device 100 comprises the relatively flexible member or shaft 22, the protective sheath 26, and one or more handles 28 to operate either the sheath 26, the electrodes 124a,b,c,d, or both. The electrodes 124a,b,c,d may be individually or simultaneously deployable and/or retractable in the direction indicated by arrow 142. The electrodes 124a, b,c,d extend out from the distal end of the electrical ablation device 100. In one embodiment, the first and second electrodes 124a, 124b may be configured as the positive electrode coupled to the anode of the energy source 14 via corresponding first and second electrical conductors 118a, 118b, and the third and fourth electrodes 124c, 124d may be configured as the negative electrode coupled to the cathode of the energy source 14 via corresponding third and fourth electrical conductors 118c, 118d, or similar electrically conductive leads or wires, through the activation switch 62. Once the electrodes 124a,b,c,d are positioned at the desired location into or proximate the tissue treatment region, the electrodes 124a,b,c,d may be connected/disconnected from the energy source 14 by actuating/de-actuating the switch 62.

As previously discussed with reference to FIGS. 2A-D, as shown in FIG. 2E in one embodiment, the protective sleeve or sheath 26 may be slideably disposed over the flexible shaft 22 and within the handle 28. In an initial phase of deployment, the sheath 26 is extended in direction 40 to cover the electrodes 124a,b,c,d to protect the trocar and prevent accidental piercing when the electrical ablation device 100 is advanced therethrough. Once the electrodes 124a,b,c,d are located into or proximate the tissue treatment region, the sheath 26 is retracted in direction 42 to expose the electrodes 124a,b,c,d. One or more of the electrodes 124a,b,c,d of the electrical ablation device 100 may be adapted and configured to slideably move in and out of a cannula, lumen, or channel formed within the flexible shaft 22. In one embodiment all of the electrodes 124a,b,c,d are configured to slideably move in and out channels formed within lumens formed within the flexible shaft 22, referred to for example as the lumen 44 in FIGS. 2A-D, to advance and retract the electrodes 124a,b,c,d as may be desired by the operator. Nevertheless, in other embodiments, it may be desired to fix all or certain ones of the one or more electrodes 124a,b,c,d in place.

The various embodiments of electrodes described in the present specification, e.g., the electrodes 24a,b, or 124a-m, may be configured for use with an electrical ablation device (not shown) comprising an elongated flexible shaft to house the needle electrodes 24a,b, or 124a-m, for example. The needle electrodes 24a,b, or 124a-m, are free to extend past a distal end of the electrical ablation device. The flexible shaft comprises multiple lumen formed therein to slideably receive the needle electrodes 24a,b, or 124a-m. A flexible sheath extends longitudinally from a handle portion to the distal end. The handle portion comprises multiple slide members received in respective slots defining respective walls. The slide members are coupled to the respective needle electrodes 24a,b, or 124a-m. The slide members are movable to advance and retract the electrode 24a,b, or 124a-m. The needle electrodes 24a,b, or 124a-m, may be independently movable by way of the respective slide members. The needle electrodes 24a,b, or 124a-m, may be deployed independently or simultaneously. An electrical ablation device (not shown) comprising an elongated flexible shaft to house multiple needle electrodes and a suitable handle is described with reference to FIGS. 4-10 in commonly owned U.S. patent application Ser. No. 11/897,676 titled "ELECTRICAL ABLATION SURGICAL INSTRUMENTS," filed Aug. 31, 2007, now U.S. Patent Application Publication No. 2009/0062788, the entire disclosure of which is incorporated herein by reference in its entirety.

It will be appreciated that the electrical ablation devices 20, 100 described with referenced to FIGS. 2A-E, may be introduced inside a patient endoscopically, transcutaneously, percutaneously, through an open incision, through a trocar (as shown in FIG. 3), through a natural orifice, or any combination thereof. In one embodiment, the outside diameter of the electrical ablation devices 20, 100 may be sized to fit within a working channel of an endoscope and in other embodiments the outside diameter of the electrical ablation devices 20, 100 may be sized to fit within a hollow outer sleeve, or trocar, for example.

FIG. 3 illustrates one embodiment of the electrical ablation system 10 shown in FIGS. 1 and 2A-D in use to treat undesirable tissue 48 located on the surface of the liver 50. The undesirable tissue 48 may be representative of a variety of diseased tissues, cancers, tumors, masses, lesions, abnormal tissue growths, for example. In use, the electrical ablation device 20 may be introduced into or proximate the tissue treatment region through a port 52 of a trocar 54. The trocar 54 is introduced into the patient via a small incision 59 formed in the skin 56. The endoscope 12 may be introduced into the patient trans-anally through the colon, trans-orally down the esophagus and through the stomach using translumenal techniques, or through a small incision or keyhole formed through the patient's abdominal wall (e.g., the peritoneal wall). The endoscope 12 may be employed to guide and locate the distal end of the electrical ablation device 20 into or proximate the undesirable tissue 48. Prior to introducing the flexible shaft 22 through the trocar 54, the sheath 26 is slid over the flexible shaft 22 in a direction toward the distal end thereof to cover the electrodes 24a,b (as shown in FIG. 2A) until the distal end of the electrical ablation device 20 reaches the undesirable tissue 48.

Once the electrical ablation device 20 has been suitably introduced into or proximate the undesirable tissue 48, the sheath 26 is retracted to expose the electrodes 24a,b (as shown in FIG. 2B) to treat the undesirable tissue 48. To ablate the undesirable tissue 48, the operator initially may locate the first electrode 24a at a first position 58a and the second electrode 24b at a second position 60 using endoscopic visualization and maintaining the undesirable tissue 48 within the field of view of the flexible endoscope 12. The first position 58a may be near a perimeter edge of the undesirable tissue 48. Once the electrodes 24a,b are located into or proximate the undesirable tissue 48, the electrodes 24a,b are energized with irreversible electroporation pulses to create a first necrotic zone 65a. For example, once the first and second electrodes 24a,b are located in the desired positions 60 and 58a, the undesirable tissue 48 may be exposed to an electric field generated by energizing the first and second electrodes 24a,b with the energy source 14. The electric field may have a magnitude, frequency, and pulse length suitable to induce irreversible electroporation in the undesirable tissue 48 within the first necrotic zone 65a. The size of the necrotic zone is substantially dependent on the size and separation of the electrodes 24a,b, as previously discussed. The treatment time is defined as the time that the electrodes 24a,b are activated or energized to generate the electric pulses suitable for inducing irreversible electroporation in the undesirable tissue 48.

This procedure may be repeated to destroy relatively larger portions of the undesirable tissue 48. The position 60 may be taken as a pivot point about which the first electrode 24a may be rotated in an arc of radius "r," the distance between the first and second electrodes 24a,b. Prior to rotating about the second electrode 24b, the first electrode 24a is retracted by pulling on the slide member 30 (FIGS. 1 and 2A-D) in a direction toward the proximal end and rotating the electrical ablation device 20 about the pivot point formed at position 60 by the second electrode 24*b*. Once the first electrode 24*a* is rotated to a second position 58*b*, it is advanced to engage the undesirable tissue 48 at point 58*b* by pushing on the slide member 30 in a direction towards the distal end. A second necrotic zone 65*b* is formed upon energizing the first and second electrodes 24*a,b*. A third necrotic zone 65*c* is formed by retracting the first electrode 24*a*, pivoting about pivot point 60 and rotating the first electrode 24*a* to a new location, advancing the first electrode 24*a* into the undesirable tissue 48 and energizing the first and second electrodes 24*a,b*. This process may be repeated as often as necessary to create any number of necrotic zones 65*p*, where p is any positive integer, within multiple circular areas of radius "r," for example, that is suitable to ablate the entire undesirable tissue 48 region. At anytime, the surgeon or clinician can reposition the first and second electrodes 24*a,b* and begin the process anew. In other embodiments, the electrical ablation device 100 comprising multiple needle electrodes 124*a-m* described with reference to FIG. 2E may be employed to treat the undesirable tissue 48. Those skilled in the art will appreciate that similar techniques may be employed to ablate any other undesirable tissues that may be accessible trans-anally through the colon, and/or orally through the esophagus and the stomach using translumenal access techniques. Therefore, the embodiments are not limited in this context.

In various embodiments, as outlined above, a surgical instrument can comprise a first electrode and a second electrode, wherein at least one the first and second electrodes can be operably coupled to a power source. In certain embodiments, as also outlined above, a first electrode can be operably coupled with a positive terminal of a voltage source and the second electrode can be operably coupled with a negative terminal of the voltage source, for example. In at least one embodiment, the first and second electrodes can comprise columnar, or point, electrodes which can be inserted into the tissue of a patient. In various circumstances, a voltage potential can be applied to the two electrodes such that a magnetic field can be created therebetween in order to treat the tissue positioned intermediate the electrodes. In some circumstances, the voltage potential may be sufficient to permit current to flow between the electrodes. Various devices are disclosed in commonly-owned co-pending U.S. patent application Ser. No. 12/352,375, entitled ELECTRICAL ABLATION DEVICES, which was filed on Jan. 12, 2009, the entire disclosure of which is incorporated by reference herein. While such devices may be suitable for their intended purposes, other devices disclosed herein can provide various advantages.

Figure 4:
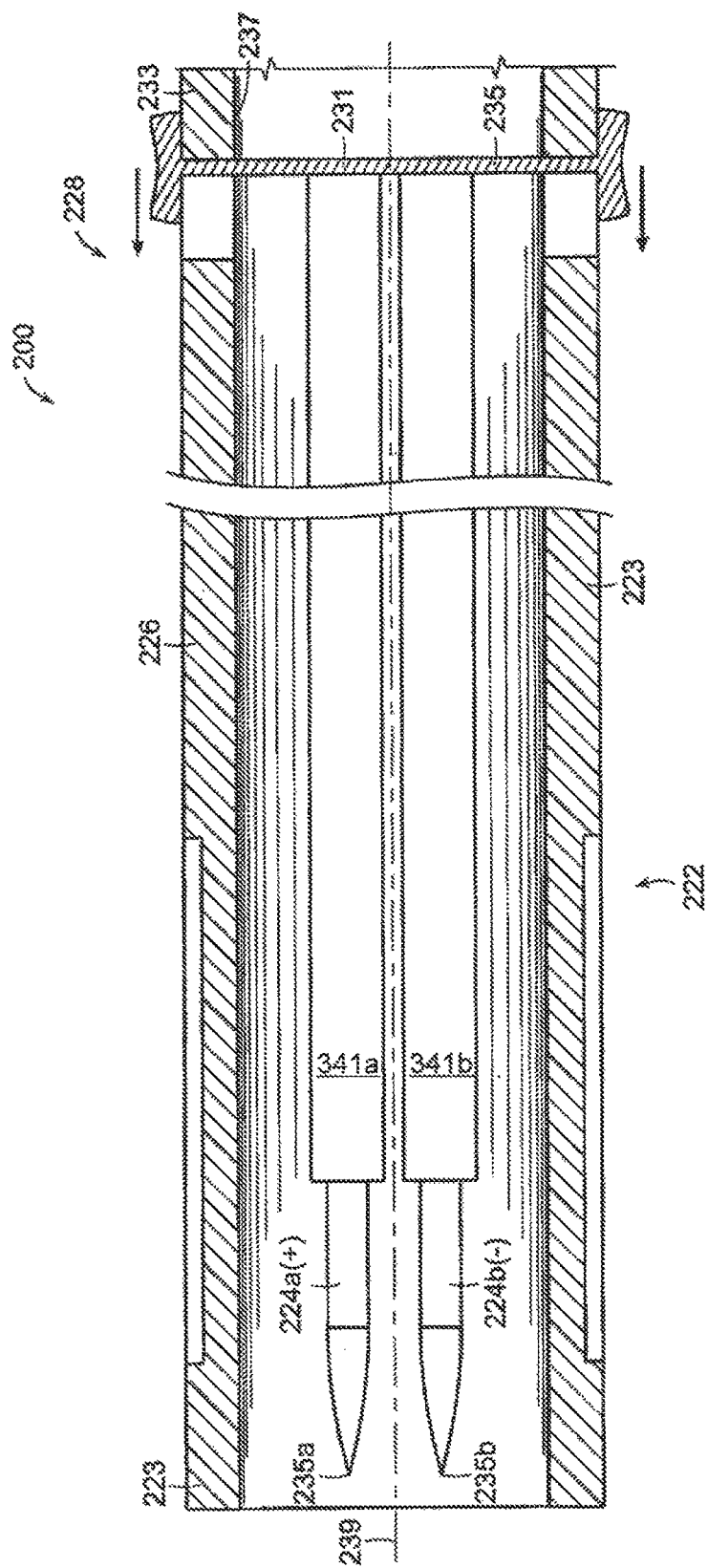
FIG. 4 is a cross-sectional view of a surgical instrument comprising a first electrode, a second electrode, and a retractable sheath movable relative to the first electrode and the second electrode.
Figure 5:
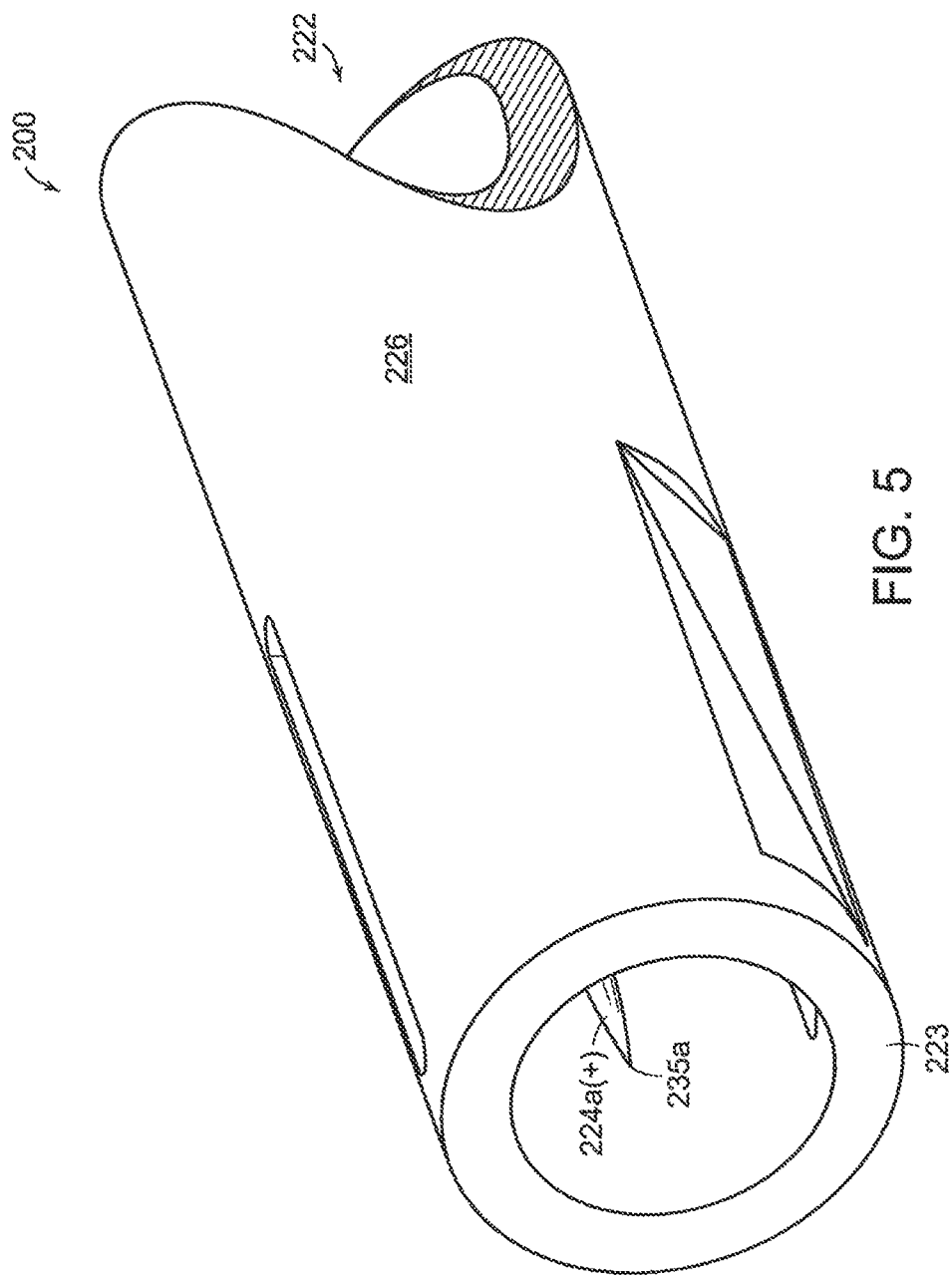
FIG. 5 is a perspective view of a distal end of the surgical instrument of FIG. 4 illustrating the sheath in an extended position.
Figure 6:
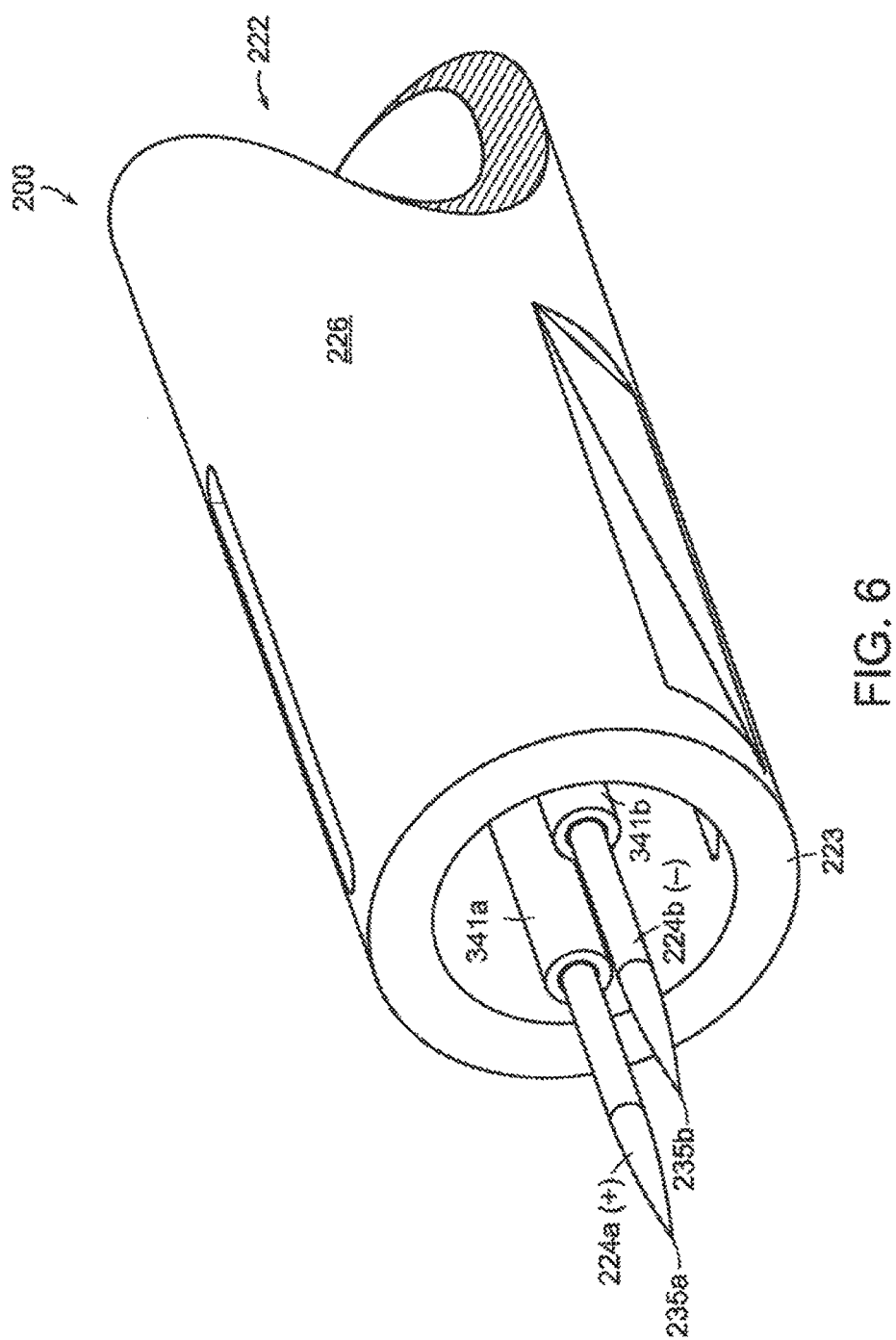
FIG. 6 is a perspective view of a distal end of the surgical instrument of FIG. 4 illustrating the sheath in a retracted position.

In various embodiments, referring now to FIGS. 4-6, a surgical instrument, such as surgical instrument 200, for example, can comprise a handle portion 228, a shaft portion 222, and one or more electrodes, such as electrodes 224*a* and 224*b*, for example. Referring to FIG. 4, handle portion 228 can comprise a first portion 231 and a second portion 233, wherein the first portion 231 and the second portion 233 can be moved relative to one another. Electrodes 224*a* and 224*b* can be mounted, or rigidly secured, to the first portion 231 wherein, in at least one embodiment, proximal ends of electrodes 224*a* and 224*b* can be mounted to first portion 231 such that the proximal ends of the electrodes do not move relative to first portion 231. In at least one embodiment, a sheath 226 of shaft portion 222 can be mounted, or rigidly secured, to second portion 233 such that, when second portion 233 is moved relative to first portion 231, sheath 226 can be moved relative to first electrode 224*a* and/or second electrode 224*b*. In various embodiments, second portion 233 can be moved between a first, or distal, position (FIG. 5) in which the distal end 223 of sheath 226 surrounds the distal ends 235*a*, 235*b* of electrodes 224*a*, 224*b* and a second, or proximal, position (FIG. 6) in which the distal end 223 of sheath 226 is retracted relative to the distal ends 235*a*, 235*b* of electrodes 224*a*, 224*b*.

In various embodiments, further to the above, sheath 226 can be moved between a distal position in which the distal ends 235*a*, 235*b* of electrodes 224*a*, 224*b* are positioned within the sheath 226 and a proximal position in which the distal ends 235*a*, 235*b* can extend distally from the distal end 223 of sheath 226. In at least one embodiment, the distal ends 235*a*, 235*b* of electrodes 224*a*, 224*b* can be recessed with respect to the distal end 223 of sheath 226 when sheath 226 is in its distal position. In use, the distal end 223 of sheath 226 can be positioned against tissue within a surgical site, for example, such that the electrodes 224*a*, 224*b* do not contact the tissue. Such embodiments may also allow the surgical instrument 200, or at least the distal end thereof, to be inserted through a trocar without the electrodes 224*a*, 224*b* coming into contact with, snagging on, and/or becoming damaged by the trocar. Once the distal end of the surgical instrument 200 has been suitably positioned relative to the targeted tissue, the sheath 226 can be retracted in order to expose the distal ends 235*a*, 235*b* of the electrodes 224*a*, 224*b* such that the electrodes can be inserted into the tissue. In various alternative embodiments, the distal ends 235*a*, 235*b* of electrodes 224*a*, 224*b* can be positioned in the same plane as the distal end of sheath 226 when the sheath 226 is in its distal-most position.

In various embodiments, as outlined above, the second portion 233 of handle 228 can be moved relative to the first portion 231 of handle 228 in order to move the sheath 226 relative to the electrodes 224*a*, 224*b*. In various circumstances, referring again to FIG. 4, the first portion 231 can be held in a stationary, or at least substantially stationary, position while the second portion 233 can be slid relative to first portion 231 by a surgeon, or other clinician, for example. In at least one embodiment, the first portion 231 can comprise a cylindrical, or at least substantially cylindrical, portion 235 and the second portion 233 can comprise a cylindrical, or at least substantially cylindrical, aperture 237 configured to receive the cylindrical portion 235 of first portion 231. The aperture 237 can be configured to closely receive cylindrical portion 235 such that relative movement therebetween can be limited to relative movement along a predetermined path, such as axis 239, for example. In certain embodiments, first portion 231 and second portion 233 can comprise one or more cooperating keys and/or grooves which can be configured to permit relative sliding movement therebetween along axis 239 while preventing, or at least inhibiting, relative movement therebetween which is transverse to axis 239.

Figure 7:
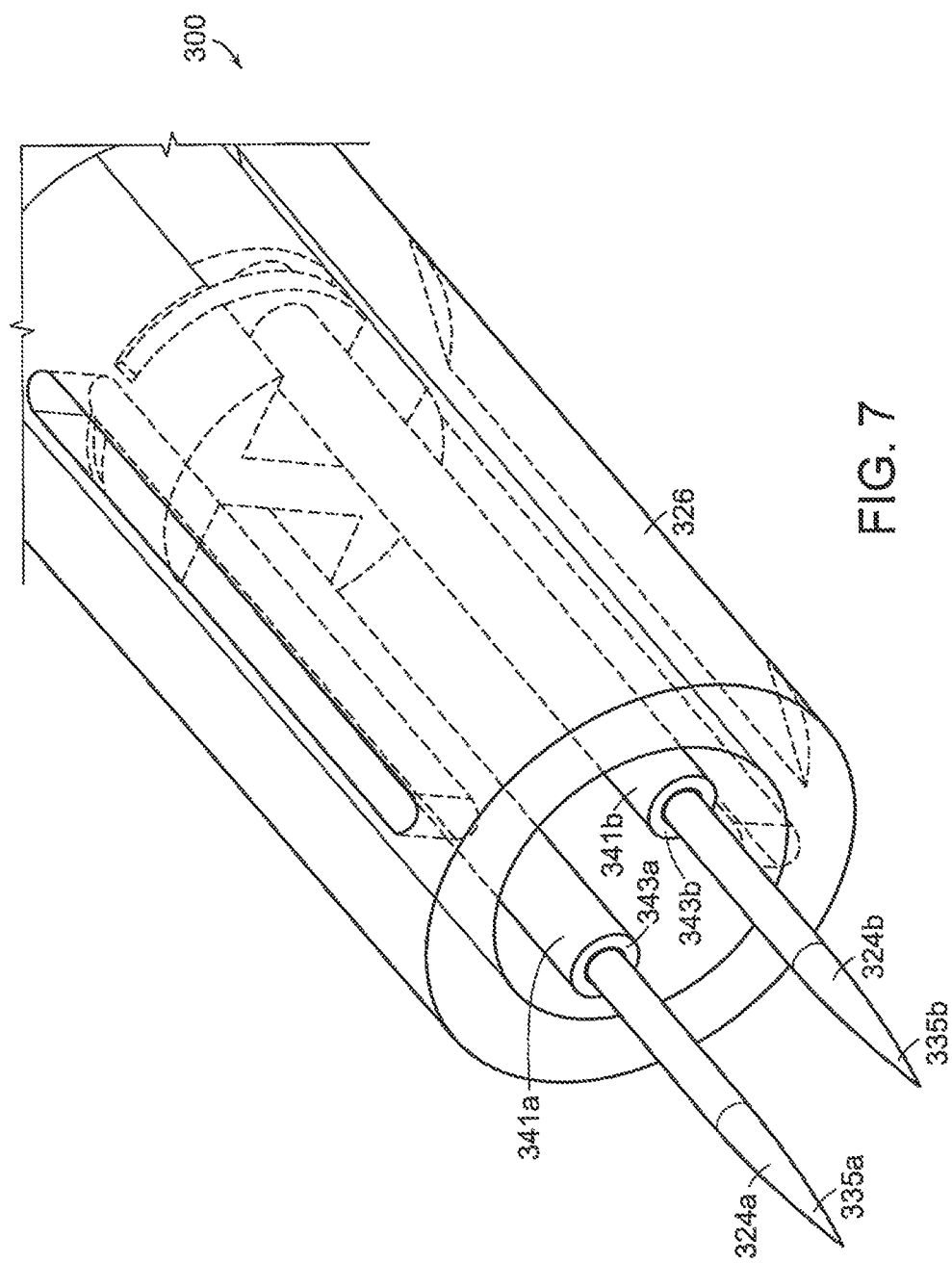
FIG. 7 is a perspective view of a distal end of an alternative embodiment of a surgical instrument illustrating a first electrode, a second electrode, and insulative jackets positioned around the first electrode and the second electrode.

In various embodiments, referring now to FIG. 7, a surgical instrument, such as surgical instrument 300, for example, can comprise a sheath 326 and one or more electrodes, such as electrodes 324*a* and 324*b*, for example. In use, similar to the above, the electrodes 324*a* and 324*b* can be inserted into tissue and a voltage differential can be applied to the electrodes such that current can flow from one electrode to the other and, in addition, flow through the tissue positioned intermediate and/or surrounding the electrodes 324*a* and 324*b*. In various embodiments, at least one electrode can comprise an insulative jacket surrounding at least a portion of the electrode such that current does not arc, or jump, between the electrodes of the surgical instrument without flowing through the tissue. In certain embodiments, such as those having two electrodes, for example, an insulative jacket may surround only one of the electrodes, wherein such an insulative jacket can be sufficient to prevent current from arcing between the electrodes. In at least one embodiment, an insulative jacket 341a can surround at least a portion of electrode 324a and, similarly, an insulative jacket 341b can surround at least a portion of electrode 324b. The insulative jackets can be comprised of any suitable material which can increase the dielectric resistance between the electrodes 324a and 324b, such as ceramic, for example. In various embodiments, as a result of the above, an insulative jacket at least partially surrounding an electrode can interrupt the air gap between the electrodes in order to reduce the possibility of current arcing between the electrodes.

In various embodiments, further to the above, insulative jacket 341a can comprise a tube having an aperture, wherein electrode 324a can extend through the aperture. In at least one embodiment, insulative jacket 341a can be mounted, or rigidly secured, to a handle portion of surgical instrument 300 and can extend along a substantial length of electrode 324a. The insulative jacket 341a can be configured such that the distal end 335a of electrode 324a is not surrounded by insulative jacket 341a and such that the distal end 335a of electrode 324a extends distally from the distal end 343a of insulative jacket 341a. Similar to the above, insulative jacket 341b can comprise a tube having an aperture, wherein electrode 324b can extend through the aperture. In at least one embodiment, insulative jacket 341b can be mounted, or rigidly secured, to a handle portion of surgical instrument 300 and can extend along the length of electrode 324b. The insulative jacket 341b can be configured such that the distal end 335b of electrode 324b is not surrounded by insulative jacket 341b and such that the distal end 335b of electrode 324b extends distally from the distal end 343b of insulative jacket 341b. In at least one such embodiment, the air gap between the electrodes 324a and 324b can be interrupted by the insulative jackets 341a, 341b except for the distance extending between the distal ends of the electrodes 324a, 324b and the distal ends of insulative jackets 341a, 341b.

Figure 8:
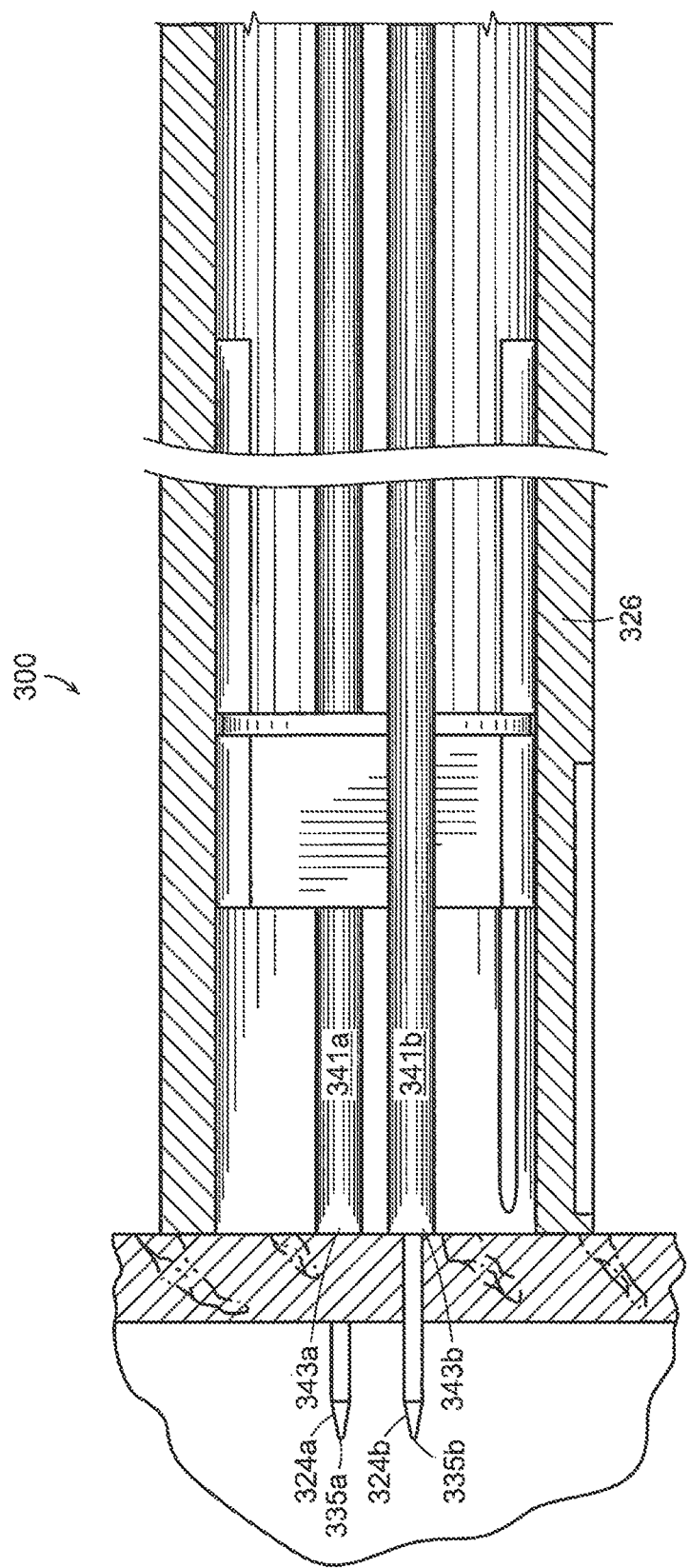
FIG. 8 is a cross-sectional view of the surgical instrument of FIG. 7 illustrating the first and second electrodes positioned within tissue and the insulative jackets positioned against the tissue.

Referring to FIG. 8, the distal ends 343a, 343b of electrodes 324a, 324b can be inserted into tissue such that, if the electrodes 324a and 324b are inserted a certain depth, insulative jacket 341a and/or insulative jacket 341b can contact the tissue. Once the insulative jacket 341a and/or insulative jacket 341b contacts the tissue, the insulative jackets can prevent, or at least inhibit, electrode 324a and/or electrode 324b from being further inserted into the tissue. In at least one embodiment, the distal end 343a and/or distal end 343b can comprise a datum which can define the maximum insertion depth of the electrode 324a and/or electrode 324b into the tissue. When the insulative jackets 341a and 341b are in contact with, or at least nearly in contact with, the tissue, very little, if any, uninterrupted air gap may exist between the electrodes 324a and 324b. In various circumstances, as a result, the possibility of current acting between the electrodes without passing through the tissue can be reduced. In various embodiments, the distal end 343a of insulative jacket 341a and the distal end 343b of insulative jacket 341b can lie along a common plane, or datum. In various other embodiments, although not illustrated, the distal ends 343a and 343b of insulative jackets 341a and 341b can define different datums and/or can provide for different insertion depths into the tissue, for example.

In various embodiments, referring now to FIG. 9, a surgical instrument, such as surgical instrument 400, for example, can comprise a sheath 426 and one or more electrodes, such as electrodes 424a and 424b, for example. In use, similar to the above, the electrodes 424a and 424b can be inserted into tissue and a voltage differential can be applied to the electrodes such that current can flow from one electrode to the other and, in addition, flow through the tissue positioned intermediate and/or surrounding the electrodes. The surgical instrument 400 can further comprise an insulative guard, such as guard 441, for example, which can be movable between a distal, or extended, position in which it is positioned intermediate the distal ends of the first electrode 424a and the second electrode 424b and a proximal, or retracted, position in which the guard 441 is displaced proximally relative to the distal ends of the first and second electrodes 424a and 424b. In various embodiments, the guard 441 can be biased into a distal position (FIG. 9) in which guard 441 is positioned intermediate the distal end 443a of first electrode 424a and the distal end 443b of second electrode 424b. In certain embodiments, the guard 441 can be biased into its distal position by a spring, such as compression spring 445, for example. More particularly, in at least one embodiment, spring 445 can be positioned intermediate a portion of sheath 426, such as support surface 447, for example, and a portion of insulative guard 441, such as surface 449 and/or projections extending therefrom, such that the compression spring 445 can apply a biasing force to guard 441 and hold guard 441 in its distal position. In such a distal position, the guard 441 can prevent, or at least reduce the possibility of, current from arcing between the electrodes.

As outlined above, the insulative guard 441 of surgical instrument 400 can be biased into its distal position by compression spring 445. In at least one embodiment, referring to FIG. 9, guard 441 can comprise a distal end 451 which can be positioned flush with the distal ends 443a and 443b of electrodes 424a and 424b. In at least one embodiment, the distal end 451 can be positioned along a datum defined by distal ends 443a and 443b. In certain other embodiments, although not illustrated, the distal end 451 of guard 441 can extend beyond the distal end 443a and/or the distal end 443b of the electrodes. As also outlined above, the guard 441 can be retracted proximally. In at least one embodiment, referring now to FIG. 10, the insulative guard 441 can be slid proximally within sheath 426 such that the insulative guard 441 is no longer positioned intermediate the distal ends 443a and 443b of the electrodes. In certain embodiments, referring now to FIG. 11, the surgical instrument 400 can be configured such that insulative guard 441 can be retracted as electrodes 424a and 424b are inserted into the tissue. More particularly, in at least one embodiment, the distal ends 443a and 443b of the electrodes and the distal end 451 of guard 441 can be positioned against tissue wherein, as the electrodes 424a and 424b enter into the tissue, the guard 441 may not enter into the tissue and, instead, may be displaced proximally, or relative to the distal ends 443a and 443b. Once the guard has been displaced proximally, in various embodiments, a voltage differential may be applied to the electrodes 424a and 424b and current may flow from one electrode to the other through the tissue.

When insulative guard 441 is displaced proximally, as outlined above, the guard 441 can compress spring 445. When spring 445 is compressed, the spring 445 can store energy therein and apply a biasing force to insulative guard 441 such that, as the electrodes 424a and 424b are extracted from the tissue, the spring 445 can displace the guard 441 distally toward the distal ends 443a and 443b of electrodes 424a and 424b. In at least one such embodiment, the distal end 451 of guard 441 can remain in contact with the tissue as the electrodes 424a and 424b are inserted into and extracted from the tissue. In various embodiments, as a result, the guard 441 can prevent, or at least reduce the possibility of, current arcing between the electrodes without passing through the tissue. Stated another way, the guard 441 can be sufficiently retracted when the electrodes 424a, 424b are inserted into tissue in order to permit current to flow between the portions of electrodes 424a, 424b within the tissue but, at the same time, sufficiently positioned against the tissue to prevent, or at least reduce the possibility of, current from flowing between the electrodes 424a, 424b at a location outside of the tissue. In various embodiments, as a result of the above, the insulative guard 441 and spring 445 arrangement can provide for a self-regulating, or self-retracting, system. In other embodiments, although not illustrated, the surgical instrument 400 can comprise an actuator configured to displace the insulative guard 441. In certain embodiments, other biasing means can be used in addition to or in lieu of a spring. In at least one embodiment, for example, a surgical instrument can comprise a motor mounted within a shaft of the surgical instrument, wherein the motor can apply a biasing force to an insulative guard in order to keep the guard biased against the tissue and yet the permit the guard to move relative to the electrodes.

In various embodiments, further to the above, surgical instrument 400 can further comprise means for controlling or defining the movement of insulative guard 441 as it is moved between its proximal and distal positions. In at least one embodiment, referring to FIGS. 9 and 10, the sheath 426 can comprise at least one elongate slot 453 and the guard 441 can comprise at least one projection 455 extending therefrom, wherein the projection 455 can be configured to slide within the slot 453. The slot 453 can be configured to limit the movement of projection 455 such that the guard 441 can move along a predetermined path relative to sheath 426, for example. In at least one embodiment, the slot 453 and projection 455 can be configured such that guard 441 is guided along an axial, or longitudinal, path between its proximal and distal positions. In at least one such embodiment, the slot 453 can comprise a linear, or at least substantially linear, profile and can be parallel to, substantially parallel to, collinear with, or substantially collinear with a longitudinal axis of sheath 426. Although not illustrated, other embodiments are envisioned in which slot 453 can comprise a curved configuration, a curvilinear configuration, and/or any other suitable configuration in order to provide or define a suitable path for guard 441. In various embodiments, although not illustrated, the sheath 426 can comprise at least one projection extending therefrom which can be configured to slide within at least groove in the insulative guard. In various embodiments, referring again to FIGS. 9 and 10, the insulative guard 441 can comprise one or more recesses or grooves, such as recesses 457a and 457b, for example, which can be configured to receive at least a portion of the electrodes 424a and 424b, respectively. More particularly, in at least one embodiment, the electrode 424a can extend through recess 457a in guard 441 and, in addition, the electrode 424b can extend through the recess 457b, wherein, in at least one embodiment, the electrodes 424a, 424b can be closely received in the recesses 457a, 457b such that guard 441 is guided therebetween.

In various embodiments, a surgical instrument can include an electrode comprising a flexible portion which can be configured to conform to the surface of an organ, such as a patient's liver, for example, and/or any other suitable tissue to be treated. In certain embodiments, referring now to FIG. 12, a surgical instrument, such as surgical instrument 500, for example, can comprise a shaft 526 and an electrode 524, wherein the electrode 524 can be comprised of a flexible, conductive mesh 525. In at least one embodiment, the surgical instrument 500 can further comprise an electrode support 561 which can be mounted to the shaft 526. The electrode support 561 can comprise a wire, or rod, having a first end and a second end mounted to the shaft 526 and an intermediate portion 565 extending between the first end and the second end. The first end and the second end of electrode support 561 can be mounted to shaft 526 in any suitable manner, such as by welding and/or fasteners, for example. In various embodiments, the intermediate portion 565 can define a perimeter configured to support the edge of the flexible mesh 525. The edge of the flexible mesh 525 can be mounted to the electrode support 561 by any suitable means such as an adhesive and/or fasteners, for example. In certain embodiments, the edge of the flexible mesh 525 can be wrapped around the electrode support 561 such that the edge of the flexible mesh 525 can be attached to itself. In any event, the electrode mesh 525 can be configured such that a central portion of the electrode mesh 525 can move relative to its edge. In at least one embodiment, the central portion of the electrode mesh 525 can be configured to deflect relative to the electrode support 561 in order to create a pocket, or pouch. The electrode mesh 525 can comprise a concave or convex configuration which can receive at least a portion of the targeted tissue therein. In various embodiments, the surgical instrument 500 can comprise a liver retractor wherein the flexible mesh 525 can deflect to receive at least a portion of a patient's liver. In at least one such embodiment, the electrode 524 may be sufficiently rigid to allow a surgeon to manipulate the patient's liver with the surgical instrument 500 and hold the electrode 524 in position.

In various embodiments, further to the above, the flexible mesh 525 can be comprised of a conductive material, such as copper and/or stainless steel, for example, wherein the flexible mesh can be operably connected with at least one conductor, such as conductor 518, for example, of the surgical instrument 500. In use, the flexible mesh 525 can be positioned relative to the tissue to be treated wherein, in at least one embodiment, a second electrode, such as electrode 524b, for example, can also be positioned relative to the tissue. Referring now to FIG. 13, the flexible electrode of surgical instrument 500 can be positioned on one side of the tissue to be treated and the second electrode can be inserted into the tissue and/or a tumor within the tissue, for example. In at least one such embodiment, the conductor 518 of surgical instrument 500 and the second electrode 524b can be operably coupled with a power source such that current can flow between the electrodes. In various embodiments, the second electrode 524b can be operably connected with a cathode, or positive pole, of the power source while the conductor 518 can be operably connected to an anode, or negative pole, of the power source and/or a suitable ground. In various other embodiments, the second electrode 524b can be operably connected to the anode of the power source and/or ground while the conductor 518 can be operably connected to the cathode of the power source. In any event, referring to FIGS. 14 and 15, the voltage potential applied to the electrode 524 and the second electrode 524b, and/or the current passing between the electrodes 524, 524b, can cause necrosis in the tissue which is in contact with and/or surrounding the electrodes 524, 524b. Such necrotic tissue can comprise necrotic tissue portion 563a and necrotic tissue portion 563b wherein, referring to FIG. 14, the necrotic tissue portion 563b can be associated with the second electrode 524b and can comprise a volume of substantially ablated and/or necrotic tissue while the necrotic tissue portion 563a can be associated with electrode 524 and can comprise a volume of only partially ablated and/or necrotic tissue, for example.

In various circumstances, further to the above, it may be desirable to control or limit the size of necrotic tissue region 563a and/or the density of the necrotic tissue within region 563a. In certain embodiments, the amount and/or density of the necrotic tissue created around the electrode 524 can depend on the intensity, or density, of the current flowing from and/or to the electrode 524. In various circumstances, the field density of the current can depend on the size of the electrode 524. More particularly, a larger electrode 524 can produce a lower current field density surrounding the electrode 524 and, as a result, generate a smaller amount of necrotic tissue, whereas a smaller electrode 524 can produce a larger current field density and, as a result, generate a larger amount of necrotic tissue. In various embodiments, referring again to FIG. 14, the necrotic tissue region 563a can be largely positioned under and/or around the electrode support 561. In view of the above, the perimeter or diameter of electrode support 561 can be increased such that a smaller amount of, and/or less dense volume of, necrotic tissue is created around electrode 524, whereas the perimeter or diameter of electrode support 561 can be decreased such that a larger amount of, and/or more dense volume of, necrotic tissue is created around electrode 524. Correspondingly, a larger perimeter or diameter of electrode support 561 can generally accommodate a larger electrode mesh 525, wherein the larger electrode mesh 525 can, as a result, contact a larger surface area of tissue. Such a larger surface area can further reduce the amount and/or density of necrotic tissue produced by electrode 524. By comparison, the amount and/or density of necrotic tissue surrounding second electrode 524b, which may comprise a needle electrode, for example, can be larger, and possibly substantially larger, than the amount and/or density of necrotic tissue surrounding electrode 524.

As outlined above, referring again to FIG. 12, the electrode mesh 525 can comprise a conductive material. In at least one embodiment, the electrode mesh 525 can be attached to shaft 526 by a mounting collar 541, wherein the mounting collar 541 can secure an end of mesh 525 in position. In at least one embodiment, the electrode mesh 525 can comprise a bag having an open end which can be slid over electrode support 561 and at least a portion of shaft 526 wherein the mounting collar 541 can be slid over at least a portion of mesh 525 to mount mesh 525 to shaft 526. In certain embodiments, the electrode mesh can comprise at least one substrate material perfused with at least one electrically-conductive material, such as saline, for example, wherein the perfused material and the substrate material can permit current to flow throughout the mesh 525 and/or between conductor 518 and electrode support 561, for example. In various embodiments, the substrate material and the perfused material can both be comprised of one or more electrically-conductive materials. In at least one embodiment, the mesh 525 can be comprised of a non-conductive, or at least substantially non-conductive, substrate material, wherein a conductive material perfused within the substrate material can conduct the current within the mesh 525. In at least one embodiment, the substrate material of mesh 525 can be porous such that the substrate material can absorb the conductive material. In various embodiments, the electrode mesh 525 can comprise at least one substrate material and, in addition, at least one conductive material coated onto the substrate material. In at least one embodiment, the substrate material can be comprised of at least one non-electrically conductive material while, in other embodiments, the substrate material can be comprised of one or more electrically conductive materials. In certain embodiments, the coated material can be comprised of a multi-filament medical polyester yarn available from ATEX Technologies, for example. As discussed above, mesh 525 can be flexible such that it can readily deflect or change shape when it contacts tissue, such as a patient's liver, for example. In certain embodiments, the mesh 525 can comprise a material having a plurality of apertures extending therethrough, wherein the apertures can be arranged in any suitable pattern. In at least one embodiment, mesh 525 can comprise a weaved material. In certain embodiments, the mesh 525 can be rigid, or at least substantially rigid, such that it does not substantially deflect when it contacts tissue.

In various embodiments, referring now to FIG. 16, a surgical instrument, such as surgical instrument 600, for example, can comprise a flexible electrode, such as balloon electrode 624, for example, wherein the electrode 624 can be configured to conform to the contour of the tissue being treated. In certain embodiments, the balloon electrode 624 can be delivered to a surgical site percutaneously and/or laprascopically, wherein the balloon electrode 624 can be positioned under and/or around the targeted tissue, such as a patient's liver, for example. In at least one embodiment, the balloon electrode 624 can be expanded in order to increase the surface area of the electrode in contact with the targeted tissue. Similar to the above, a larger surface area in contact with the tissue can reduce the amount of, and/or the density of, the necrotic tissue created. In various embodiments, also similar to the above, a second electrode can be inserted into the targeted tissue, wherein the second electrode can be operably coupled with the cathode, or positive terminal, of a power source and the balloon electrode 624 can comprise a return electrode which can be operably coupled with the anode, or negative terminal, of the power source and/or any suitable ground, for example. In other embodiments, the electrode 624 can be operably coupled with the cathode, or positive terminal, of the power source and the second electrode can be operably coupled with the anode, or negative terminal, of the power source and/or any other suitable ground. In various alternative embodiments, a surgical instrument can include an electrode comprising a flexible sheet which is positioned against or relative to the targeted tissue.

In various embodiments, referring now to FIGS. 17 and 18, a surgical instrument, such as surgical instrument 700, for example, can comprise a plurality of electrodes, such as electrodes 724a, 724b, 724c, and 724d, for example, which can be configured and arranged to treat tissue in a desired manner. Similar to the above, the electrodes 724a-724d can extend distally from shaft 722 and protective sleeve 726 such that the electrodes can be inserted into tissue. In certain embodiments, also similar to the above, the electrodes 724a and 724b can be operably coupled with a cathode, or positive terminal, of a power source, whereas the electrodes 724c and 724d can be operably coupled with an anode, or negative terminal, of a power source. Referring primarily to FIG. 18, the electrodes 724a-724d can be positioned and arranged with respect to a central axis, such as axis 799, for example, wherein, in certain embodiments, axis 799 can be defined by the center of shaft 722. In various embodiments, the electrodes 724a-724d can each comprise a columnar electrode having a central axis, wherein the central axes of the electrodes 724a-724d can be positioned relative to axis 799. For example, the central axis of electrode 724a can be positioned a distance D1 away from axis 799, the central axis of electrode 724b can be positioned a distance D2 away from axis 799, the central axis of electrode 724c can be positioned a distance D3 away from axis 799, and the central axis of electrode 724d can be positioned a distance D4 away from axis 799. In certain embodiments, distance D1 can be equal to, or at least substantially equal to, distance D2 while, in various embodiments, distance D3 can be equal to, or at least substantially equal to, distance D4. Referring again to FIG. 18, distances D1 and D2 can be larger than distances D3 and D4 such that electrodes 724a and 724b care positioned further away from axis 799 than electrodes 724c and 724d. In various embodiments, distances D1, D2, D3, and/or D4 can range between approximately 0.25 cm and approximately 1.0 cm, for example.

When electrodes 724a-724d are polarized by a power source, referring again to FIG. 18, a voltage field can be created which surrounds the electrodes. In various embodiments, the voltage field can comprise one or more isolines, wherein each isoline can represent portions of the voltage field which have the same magnitude. For example, the voltage field generated by electrodes 724a-724d can be represented by a plurality of isolines, such as isoline 798a, for example, wherein isoline 798a can represent a perimeter surrounding the electrodes having a constant voltage field magnitude. Similarly, the electrodes 724a-724d can produce an isoline 798b which can represent a perimeter surrounding the electrodes having a constant voltage field magnitude which is different than the magnitude of isoline 798a, for example. In various embodiments, the isoline 798b can represent a voltage field magnitude which is greater than the magnitude represented by isoline 798a. In various embodiments, referring now to FIG. 19, the magnitude of the voltage field produced by the electrodes may not be constant at all locations surrounding the electrodes; on the contrary, the magnitude of the voltage field may be different at various locations surrounding the electrodes. For example, the voltage field, or at least a portion of the voltage field produced by the surgical instrument 700 can be represented by graph 797a in FIG. 19. More particularly, the graph 797a can represent the magnitude of the voltage field measured in a plane which includes the center axis of electrode 724c, center axis 799, and electrode 724d. Graph 797a, however, may not necessarily represent the magnitude of the voltage field in other planes. Upon examining the graph 797a, it can be seen that, in at least one embodiment, the voltage field produced by the electrodes 724a-724d can comprise a symmetrical, or at least substantially symmetrical, profile centered about axis 799. Furthermore, it can be seen from graph 797a that the magnitude of the voltage field has two valleys 795c, 795d centered about, or at least positioned adjacent to, the electrodes 724c and 724d, respectively. In various embodiments, the magnitude of the voltage field at valleys 795c and/or 795d may be zero or, alternatively, greater than zero.

In various embodiments, referring again to the graph 797a in FIG. 19, the magnitude of the voltage field surrounding electrodes 724a-724d can be the same, or at least substantially the same, at distances of between about 6 cm to about 10 cm away from axis 799 in the lateral directions, for example. Stated another way, the change in magnitude, or gradient, of the voltage field produced by surgical instrument 700 between about 6 cm and about 10 cm away from the center of surgical instrument 700 may be very small. In at least one embodiment, for example, the gradient, or rate of change of the magnitude of the voltage field, between about 9 cm and about 10 cm may be about 0.04 VDC per millimeter, for example. In other various embodiments, the gradient may be about 0.01 VDC/mm, about 0.02 VDC/mm, about 0.03 VDC/mm, about 0.05 VDC/mm, about 0.06 VDC/mm, about 0.07 VDC/mm, about 0.08 VDC/mm, about 0.09 VDC/mm, about 0.10 VDC/mm, about 0.11 VDC/mm, about 0.12 VDC/mm, and/or about 0.13 VDC/mm, for example. In various circumstances, it may be desirable for surgical instrument 700 to produce a voltage field having a gradient below about 0.14V/mm, wherein a voltage field gradient at or larger than 0.14 V/mm may cause a contraction of muscle, and/or other tissue, surrounding the surgical site. Referring now to the graph 797b in FIG. 19, the graph 797b can represent the magnitude of the voltage field measured in a plane which includes the center axis of electrode 724a, center axis 799, and electrode 724b, although the graph 797b may not necessarily represent the magnitude of the voltage field in other planes. In various circumstances, the planes used to establish graphs 797a and 797b may be orthogonal, or perpendicular, to one another. Upon examining the graph 797b, it can be seen that, in at least one embodiment, the voltage field produced by the electrodes 724a-724d can comprise a symmetrical, or at least substantially symmetrical, profile centered about axis 799. Furthermore, it can be seen from graph 797b that the magnitude of the voltage field has two peaks 795a, 795b centered about, or at least positioned adjacent to, the electrodes 724a and 724b, respectively. Similar to the above, it can be seen from graph 797b that the gradient of the magnitude of the voltage field between about 9 cm and about 10 cm away from axis 799 may be about 0.04 VDC per millimeter, for example. In other various embodiments, the gradient may be about 0.01 VDC/mm, about 0.02 VDC/mm, about 0.03 VDC/mm, about 0.05 VDC/mm, about 0.06 VDC/mm, about 0.07 VDC/mm, about 0.08 VDC/mm, about 0.09 VDC/mm, about 0.10 VDC/mm, about 0.11 VDC/mm, about 0.12 VDC/mm, and/or about 0.13 VDC/mm, for example.

Viewing graphs 797a and 797b together, further to the above, the voltage field produced by surgical instrument 700 between about 6 cm and about 10 cm away from axis 799 in all directions could be represented by a single isoline, or isoplane, which surrounds the electrodes 724a-724d. When electrodes 724a-724d are positioned in tissue, such an isoplane can represent very little, if any, voltage gradient through the tissue which, as a result, can result in little, if any contraction of the tissue within the 6 cm to 10 cm region, for example. As outlined above, referring against to graphs 797a and 797b in FIG. 19, the magnitude of the voltage field produced by the surgical instrument 700 is a function of the voltage potential, or differential, supplied to the electrodes 724a-724d. A lower voltage potential, or differential, supplied to the electrodes can result in a voltage field having a lower average magnitude as compared to when a higher voltage potential, or differential, is supplied to the electrodes 724a-724d. In various embodiments, further to the above, the same voltage potential, or at least substantially the same voltage potential, supplied to electrode 724a can be supplied to electrode 724b. In certain embodiments, the same voltage potential, or at least substantially the same voltage potential, supplied to electrode 724c can be supplied to electrode 724d.

In various embodiments, referring now to FIGS. 20 and 21, a surgical instrument, such as surgical instrument 900, for example, can comprise a first array of electrodes, such as electrodes 924a, 924b, and 924c, for example, which can be operably coupled with a first conductor. In addition, the surgical instrument 900 can further comprise a second array of electrodes, such as electrodes 924d, 924e, and 924f, for example, which can be operably coupled with a second conductor. Further to the above, the first conductor can be operably coupled with a cathode, or positive terminal, of a power source, whereas the second conductor can be operably coupled with an anode, or negative terminal, of the power source, for example. In various embodiments, referring primarily to FIG. 21, the electrodes 924a-924f can be arranged along first and second lines. More particularly, in at least one embodiment, electrodes 924a, 924e, and 924c can be positioned along a first line while electrodes 924d, 924b, and 924f can be positioned along a second line. In certain embodiments, the first line can be parallel to, or at least substantially parallel to, the second line. With regard to the first line of electrodes, in various embodiments, positive electrode 924a can be positioned on one side of negative electrode 924e while positive electrode 924c can be positioned on the opposite side of electrode 924e. Similarly, with regard to the second line of electrodes, negative electrode 924d can be positioned on one side of positive electrode 924b while negative electrode 924f can be positioned on the opposite side of electrode 924b. In certain embodiments, electrodes 924a, 924b, and 924c can have the same, or at least substantially the same, voltage potential while, in at least one embodiment, electrodes 924d, 924e, and 924f can have the same, or at least substantially the same, voltage potential.

In various embodiments, further to the above, the first array of electrodes comprising electrodes 924a, 924b, and 924c can be set to a first polarity while the second array of electrodes comprising electrodes 924d, 924e, and 924f can be set to a second polarity. In certain embodiments, the polarity of the first array of electrodes can be adjusted simultaneously while the polarity of the second array of electrodes can be adjusted simultaneously, and independently, of the first array of electrodes. In various embodiments, the electrode 924a can be operably coupled to a first conductor, the electrode 924b can be operably coupled to a second conductor, the electrode 924c can be operably coupled to a third conductor, the electrode 924d can be operably coupled with a fourth conductor, the electrode 924e can be operably coupled with a fifth conductor, and the electrode 924f can be operably coupled with a sixth conductor. In at least one such embodiment, each of the conductors can be operably coupled with an output of a voltage source, wherein the voltage source can be configured to supply different voltage potentials to one, some, and/or all of the conductors and their corresponding electrodes. In the exemplary embodiment of surgical instrument 900, such a voltage source could supply six different voltage potentials, wherein, in at least one embodiment, each of the voltage potentials could be adjusted before, and/or during, the operation of the surgical instrument.

In certain embodiments, referring again to FIG. 21, the electrodes 924a, 924e, and 924c can be attached to and/or bonded to one another with an insulator positioned intermediate the electrodes 924a, 924e, and 924c. Similarly, electrodes 924d, 924b, and 924f can be attached to and/or bonded to one another within an insulator positioned intermediate the electrodes 924d, 924b, and 924f. In various embodiments, air gaps can be present between the electrodes 924a-924f. In any event, although surgical instrument 900 is described and illustrated as comprising six electrodes, other embodiments are envisioned which can comprise less than six electrodes or more than six electrodes, such as embodiments comprising eight electrodes arranged in two rows of four electrodes, or embodiments comprising ten electrodes arranged in two rows of five electrodes, for example. Furthermore, although surgical instrument 900 is described and illustrated as comprising two rows of electrodes, other embodiments are envisioned which can comprise more than two rows of electrodes, such as embodiments comprising nine electrodes arranged in three rows of three electrodes, for example.

The embodiments of the devices described herein may be introduced inside a patient using minimally invasive or open surgical techniques. In some instances it may be advantageous to introduce the devices inside the patient using a combination of minimally invasive and open surgical techniques. Minimally invasive techniques may provide more accurate and effective access to the treatment region for diagnostic and treatment procedures. To reach internal treatment regions within the patient, the devices described herein may be inserted through natural openings of the body such as the mouth, anus, and/or vagina, for example. Minimally invasive procedures performed by the introduction of various medical devices into the patient through a natural opening of the patient are known in the art as NOTES™ procedures. Some portions of the devices may be introduced to the tissue treatment region percutaneously or through small-keyhole-incisions.

Endoscopic minimally invasive surgical and diagnostic medical procedures are used to evaluate and treat internal organs by inserting a small tube into the body. The endoscope may have a rigid or a flexible tube. A flexible endoscope may be introduced either through a natural body opening (e.g., mouth, anus, and/or vagina) or via a trocar through a relatively small-keyhole-incision incisions (usually 0.5-1.5 cm). The endoscope can be used to observe surface conditions of internal organs, including abnormal or diseased tissue such as lesions and other surface conditions and capture images for visual inspection and photography. The endoscope may be adapted and configured with working channels for introducing medical instruments to the treatment region for taking biopsies, retrieving foreign objects, and/or performing surgical procedures.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Other sterilization techniques can be done by any number of ways known to those skilled in the art including beta or gamma radiation, ethylene oxide, and/or steam.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument configured to deliver electrical energy to the tissue of a patient, comprising:
    a frame;
    a first electrode, comprising:
        an elongate portion defined along a first axis; and
        a distal portion configured to contact the tissue;
    a second electrode, comprising:
        an elongate portion defined along a second axis; and
        a distal portion configured to contact the tissue;
    a guard movable between a first position and a second position, wherein said guard is comprised of an electrically insulative material; and
    a spring positioned intermediate said guard and said frame, wherein said guard is positioned intermediate said distal portion of said first electrode and said distal portion of said second electrode when said guard is in said first position, wherein said spring is configured to bias said guard into said first position, and wherein said guard is retracted proximally with respect to said first electrode and said second electrode and not positioned intermediate said distal portion of said first electrode and said distal portion of said second electrode when said guard is in said second position,
    wherein when said guard is in said first position, a distal end of said guard is positioned at least flush with distal ends of said first electrode and said second electrode, which prevents current from arcing between said first electrode and said second electrode when said guard is in said first position; and
    wherein when said guard is in said second position, said distal end of said guard is in contact with the tissue, which prevents current from arcing between said first electrode and said second electrode without passing through the tissue when said guard is in said second position.

2. The surgical instrument of claim 1, wherein said guard is configured to move from said first position to said second position when said first electrode and said second electrode are inserted into the tissue.

3. The surgical instrument of claim 1, wherein said guard is configured to move from said first position to said second position when said guard contacts the tissue.

4. A surgical instrument configured to deliver electrical energy to the tissue of a patient, comprising:
    a housing;
    a first electrode, comprising:
        a first elongate portion defined along a first axis; and
        a first distal portion;
    a second electrode, comprising:
        a second elongate portion defined along a second axis; and
        a second distal portion;
    a guard comprising a distal end, wherein said guard is positioned intermediate said first electrode and said second electrode; and
    a resilient member positioned intermediate said guard and said housing, wherein said guard is movable between a distal position and a proximal position, wherein said resilient member is configured to bias said guard into said distal position,
    wherein when said guard is in said distal position, said distal end of said guard is positioned at least flush with distal ends of said first electrode and said second electrode, which prevents current from arcing between said first electrode and said second electrode when said guard is in said distal position, and
    wherein when said guard is in said proximal position, said distal end of said guard is in contact with the tissue, which prevents current from arcing between said first electrode and said second electrode without passing through the tissue when said guard is in said proximal position.

5. The surgical instrument of claim 4, wherein said guard is comprised of an electrically insulative material.

6. The surgical instrument of claim 4, wherein said guard is configured to move from said distal position to said proximal position when said first electrode and said second electrode are inserted into the tissue.

7. The surgical instrument of claim 4, wherein said guard is configured to move from said distal position to said proximal position when said guard contacts the tissue.

8. The surgical instrument of claim 4, wherein said distal end of said guard extends beyond said first distal portion and said second distal portion when said guard is in said distal position.

9. A surgical instrument configured to deliver electrical energy to the tissue of a patient, comprising:
    a sheath;
    a first electrode, comprising:
        a first elongate portion defined along a first axis; and
        a first distal end portion configured to contact the tissue;
    a second electrode, comprising:
        a second elongate portion defined along a second axis; and
        a second distal end portion configured to contact the tissue;
    a guard comprising a distal end, wherein said guard is movable between a first position and a second position; and
    a biasing means positioned intermediate said guard and said sheath, wherein said guard is positioned intermediate said first electrode and said second electrode, wherein said biasing means is configured to bias said guard into said first position, and wherein said distal end of said guard extends between said first distal end portion and said second distal end portion when said guard is in said first position,
    wherein said guard is retracted proximally with respect to said first electrode and said second electrode when said guard is in said second position,
    wherein when said guard is in said first position, said distal end of said guard is positioned at least flush with distal ends of said first electrode and said second electrode, which prevents current from arcing between said first electrode and said second electrode when said guard is in said first position; and
    wherein when said guard is in said second position, said distal end of said guard is in contact with the tissue, which prevents current from arcing between said first electrode and said second electrode without passing through the tissue when said guard is in said second position.

10. The surgical instrument of claim 9, wherein said guard is comprised of an electrically insulative material.

11. The surgical instrument of claim 9, wherein said guard is configured to move from said first position to said second position when said first electrode and said second electrode are inserted into the tissue.

12. The surgical instrument of claim 9, wherein said guard is configured to move from said first position to said second position when said guard contacts the tissue.

13. The surgical instrument of claim 9, wherein said distal end of said guard extends beyond said first distal end portion and said second distal end portion when said guard is in said first position.

14. The surgical instrument of claim 9, wherein said distal end of said guard is positioned flush with said first distal end portion and said second distal end portion.

* * * * *